(12) United States Patent
Corn et al.

(10) Patent No.: US 9,139,863 B2
(45) Date of Patent: Sep. 22, 2015

(54) ENGINEERED CONFORMATIONALLY-STABILIZED PROTEINS

(71) Applicant: Genentech, Inc., South San Francisco, CA (US)

(72) Inventors: Jacob E. Corn, Berkeley, CA (US); Yingnan Zhang, South San Francisco, CA (US); Aaron H. Phillips, El Cerrito, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/829,094

(22) Filed: Mar. 14, 2013

(65) Prior Publication Data

US 2013/0281314 A1 Oct. 24, 2013

Related U.S. Application Data

(60) Provisional application No. 61/612,228, filed on Mar. 16, 2012, provisional application No. 61/663,504, filed on Jun. 22, 2012.

(51) Int. Cl.
*C12Q 1/37* (2006.01)
*C07K 14/00* (2006.01)

(52) U.S. Cl.
CPC . *C12Q 1/37* (2013.01); *C07K 14/00* (2013.01); *G01N 2500/04* (2013.01)

(58) Field of Classification Search
CPC ............. B01J 2219/00659; B01J 2219/00585; A61K 38/00; C07K 14/47; C07K 16/40; C12N 9/99; C12N 9/6424
USPC ............................ 506/9; 530/350; 435/184, 7
See application file for complete search history.

(56) References Cited

U.S. PATENT DOCUMENTS

| | | | |
|---|---|---|---|
| 4,522,811 A | 6/1985 | Eppstein et al. | |
| 4,708,871 A | 11/1987 | Geysen | |
| 4,833,092 A | 5/1989 | Geysen | |
| 5,223,409 A | 6/1993 | Ladner et al. | |
| 5,403,484 A | 4/1995 | Ladner et al. | |
| 5,427,908 A | 6/1995 | Dower et al. | |
| 5,432,018 A | 7/1995 | Dower et al. | |
| 5,498,530 A | 3/1996 | Schatz et al. | |
| 5,498,538 A | 3/1996 | Kay et al. | |
| 5,556,762 A | 9/1996 | Pinilla et al. | |
| 5,571,689 A | 11/1996 | Heuckeroth et al. | |
| 5,580,717 A | 12/1996 | Dower et al. | |
| 5,624,821 A | 4/1997 | Winter et al. | |
| 5,627,024 A | 5/1997 | Maruyama et al. | |
| 5,648,260 A | 7/1997 | Winter et al. | |
| 5,663,143 A | 9/1997 | Ley et al. | |
| 5,698,426 A | 12/1997 | Huse | |
| 5,723,286 A | 3/1998 | Dower et al. | |
| 5,723,323 A | 3/1998 | Kauffman et al. | |
| 5,734,018 A | 3/1998 | Rutter et al. | |
| 5,750,373 A | 5/1998 | Garrard et al. | |
| 5,763,192 A | 6/1998 | Kauffman et al. | |
| 5,766,905 A | 6/1998 | Studier et al. | |
| 5,770,434 A | 6/1998 | Huse | |
| 6,270,964 B1 | 8/2001 | Michnick et al. | |
| 6,294,330 B1 | 9/2001 | Michnick et al. | |
| 2005/0260186 A1 | 11/2005 | Bookbinder et al. | |
| 2006/0099686 A1* | 5/2006 | Fiedler et al. | 435/69.1 |
| 2006/0104968 A1 | 5/2006 | Bookbinder et al. | |
| 2009/0032592 A1 | 2/2009 | Christensen | |
| 2013/0225436 A1* | 8/2013 | Sidhu et al. | 506/9 |

FOREIGN PATENT DOCUMENTS

| | | |
|---|---|---|
| WO | WO-84/03506 A1 | 9/1984 |
| WO | WO-84/03564 A1 | 9/1984 |
| WO | WO-94/29351 A2 | 12/1994 |
| WO | WO-94/29351 A3 | 12/1994 |
| WO | WO-95/20672 A1 | 8/1995 |
| WO | WO-95/34683 A1 | 12/1995 |
| WO | WO-96/14422 A1 | 5/1996 |
| WO | WO-97/09446 A1 | 3/1997 |
| WO | WO-97/15390 A1 | 5/1997 |
| WO | WO-97/35196 A1 | 9/1997 |
| WO | WO-97/46251 A1 | 12/1997 |
| WO | WO-97/47314 A1 | 12/1997 |
| WO | WO-98/13410 A1 | 4/1998 |
| WO | WO-98/14277 A1 | 4/1998 |
| WO | WO-98/15833 A1 | 4/1998 |

(Continued)

OTHER PUBLICATIONS

Johnston Sc et al. Structural basis for the specificity of ubiquitin C-terminal hydrolase. 1999. The EMBO Journal. vol. 18 No. 14 pp. 3877-3887.*

Tank Emh et al. Disease-Associated Mutant Ubiquitin Causes Proteasomal Impairment and Enhances Toxicity of Protein Aggregates. 2009. PLoS Genetics. 5(2): e10000382. doi:10.1371/journal.pgen.1000382.*

Ayres et al., "The Complete DNS Sequence of autographa californica nuclear polyhedrosis virus" *Virology* 202:588-605 (1994)

Bahrami et al., "Probabilistic interaction network of evidence algorithm and its application to complete labeling of peak lists from protein NMR spectroscopy" *PLoS Comput Biol* 5(3 Suppl e-2000307): 1-15 (Jun. 2009).

Barrett et al., "Selevtive enrichment and characterization of high affinity ligands from collections of random peptides on filamentous phage" *Analytical Biochemistry* 204:357-364 (1992).

(Continued)

*Primary Examiner* — David J Steadman
*Assistant Examiner* — Paul Holland
(74) *Attorney, Agent, or Firm* — Morrison & Foerster LLP

(57) ABSTRACT

Provided herein are conformationally stabilized ubiquitin proteins and methods for using the same to identify agents that bind to the stabilized ubiquitin protein or that bind to a protein that interacts with or processes the stabilized form of the ubiquitin protein. Also provided herein are methods for screening for conformationally stabilized proteins having increased binding affinity to a binding partner in comparison to the binding affinity of the wildtype form of the protein to the binding partner.

15 Claims, 36 Drawing Sheets

(56) References Cited

FOREIGN PATENT DOCUMENTS

| WO | WO-98/20036 A1 | 5/1998 |
|---|---|---|
| WO | WO-98/20159 A1 | 5/1998 |
| WO | WO-98/20169 A1 | 5/1998 |
| WO | WO-99/51642 A1 | 10/1999 |
| WO | WO-00/00823 A1 | 1/2000 |
| WO | WO-00/06717 A2 | 2/2000 |
| WO | WO-00/06717 A3 | 2/2000 |
| WO | WO-00/06717 A9 | 2/2000 |
| WO | WO-00/39585 A1 | 7/2000 |
| WO | WO-2004/035085 A1 | 4/2004 |

OTHER PUBLICATIONS

Boudreaux et al., "Ubiquitin vinyl methyl ester binding orients the misaligned active site of the ubiquitin hydrolase UCHL1 into productive conformation" *Proc Natl Acad Sci USA* 107:9117-9122 (2010).

Cai et al., "An efficient and cost-effective isotope labeling protocol for proteins expressed in *Escherichia coli*" *J. Biomol NMR* 11(1):97-102 (Jan. 1998).

Carver et al., "A general two-site solution for the chemical exchange produced dependence of T2 upon the carr-purcell pulse separation" *Journal of Magnetic Resonance* 6:89-105 (1972).

Chen et al., "Genonmic and host range studies of *Maruca virata* nucleopolyhedrovirus" *Journal of General Virology* 89:2315-2330 (2008).

Chothia et al. "Canoncial structures for the hypervariable regions of immunogobulins," *J. Mol. Biol.* 196:901-917 (1987).

Chowdhury et al. et al., "Improving antibody affinity by mimicking somatic hypermutation in vitro" *Nat Biotechnol* 17:568-572 (Jun. 1999).

Ciechanover et al., "The ubiquitin system: pathogenesis of human disease and drug targeting" *Biochim. Biophys. Acta* 1695:3-17 (2004).

Clackson et al., "Making antibody fragments using phage display libraries" *Nature* 352(6336):624-628 (Aug. 15, 1991).

Claugue et al., "Ubiquitin: Same Molecule. Different Degradation Pathways" *Cell* 143:682-685 (Nov. 24, 2010).

Cohen et al., "Will the ubiquitin system furnish as many drug targets as protein kinases?" *Cell* 143:686-693 (2010).

Coligan et al., *Current Protocols in Immunology*, vol. 3, John Wiley & Sons, Inc. "Experimental Autoimmune Encephalomyelitis in the Rat," 17 pages (1994).

Cwirla et al., "Peptides on phage: a vast library of peptides for identifying ligands" *P Natl Acad Acad Sci USA* 87:6378-6382 (Aug. 1990).

D'Arcy et al., "Inhibition of proteasome deubiquitinating activity as a new cancer therapy" *Nat. Med.* 17:1636-1640 (2011).

Delaglio et al., "NMRPipe: a multidimensional spectral processing system based on UNIX pipes" *J. Biomol. NMR* 6(3):277-293 (Nov. 1995).

Dong et al. "Preparation of distinct ubiquitin chain reagents of high purity and yield," *Structure* 19:1053-1063 (Aug. 10, 2011).

Dueber et al., "Antagonists induce a conformational change in cIAP1 that promotes autoubiquitination" *Science* 334:376-380 (Oct. 21, 2011).

Duncan and Winter, "The Binding Site for Clq on IgG" *Nature* 332:738-740 (Apr. 21, 1988).

Efimov et al., "Bacteriophage T4 as a Surface Display Vector" *Virus Genes* 10(2):173-177 (1995).

Faesen et al., "Mechanism of USP7/HAUSP activation by its c-terminal ubiquitin-like domain and allosteric regulation by GMP-synthetase" *Molecular Cell* 44:147-159 (Oct. 7, 2011).

Fernandez-Montalvan et al., "Biochemical characterization of USP7 reveals post-translational modification sites and structural requirements for substrate processing and subcellular localization" *Febs J* 274:4256-4270 (2007).

Findeisen et al. "A 1H-NMR Thermometer Suitable for cryoprobes," *Magnetic Resonance in Chemistry* 45:175-178 (2007, e-pub. Dec. 11, 2006).

Fleishman et al., "RosettaScripts: A scripting language interface to the rosetta macromolecular modeling suite" *PLoS One* 6(6 Suppl e20161):1-10 (Jun. 2011).

Friedland et al., "A correspondence between solution-state dynamics of an individual protein" *PLoS Comput Biol* 5(5 Suppl e1000393):1-16 (May 2009).

Ganesan et al., "Unraveling the allosteric mechanism of serine protease inhibition of an antibody" *Structure* 17:1614-1624 (Dec. 9, 2009).

Gao et al., "Two-state selection of conformation-specific antibodies" *Proc. Natl. Acad. Sci. USA* 106(9):3071-3076 (Mar. 2, 2009)

GenBank, Accession No. AY243110, Apr. 9, 2003, Last visited on Dec. 31, 2013, pp. 1-2.

Geysen et al., "Use of peptide synthesis to probe viral antigens for epitopes to a resolution of a single amino acid" *P Natl Acad Sci USA* 81:3998-4002 (1984).

Geysen et al., "Small peptides induce antibodies with a sequence and structural requirement for binding antigen comparable to antibodies raised against the native protein" *P Natl Acad Sci USA* 82:178-182 (1985).

Geysen et al., "The delineation of peptides able to mimic assembled epitopes" *Synthetic peptides as Antigens*, Ciba Found Symp. 119, John Wiley & Sons, pp. 130-149 (1986).

Geysen et al., "Strategies for epitope analysis using peptide synthesis" *J Immunol Methods* 102:259-274 (1987).

Graff et al., "Directed evolution of an anti-carcinoembryonic antigen scFv with a 4-day monovalent dissotion half-time at 37 degrees C" *Protein Eng. Des. Sel.* 17(4):293-304 (Jun. 2004).

Gram et al., "In vitro selection and affinity maturation of antibodies from a naive combinatorial immunoglobulin library" *P Natl Acad Sci USA* 89:3576-3580 (Apr. 1992).

Gray et al., "Protein-protein docking with simultaneous optimization of rigid-body displacement and side-chain conformations" *J. Mol. Biol.* 331(1):281-299 (Aug. 1, 2003).

Grzesiek et al., "The importance of not saturating water in protein NMR. Application to sensitivity enhancement and NOE measurements" *J Am Chem Soc.* 115:12593-12594 (1993).

Hammes et al., "Conformational selection or induced fit: a flux description of reaction mechanism" *Proc. Natl. Acad. Sci. USA* 106(33):13737-13741 (Aug. 2009).

Hammes et al., "Flexibility, diversity, and cooperativity: pillars of enzyme catalysis" *Biochemistry* 50:10422-10430 (2011).

Hanna et al. "Ubiquitin depletion as a key mediator of toxicity by tranlational inhibitors," *Molecular and Cellular Biology* 23(24):9251-9261 (Dec. 2003).

Hansen et al., "An exchange-free measure of 15N transverse relaxation: An NMR spectroscopy application to the study of a folding intermediate with pervasive chemical exchange" *J Am Chem Soc.* 129:11468-11479 (2007).

Hansen et al., "Selective Characterization of Microsecond Motions in Proteins by NMR Relation" *J. Am. Chem. Soc.* 131:16257-16265 (2009).

Havranek et al., "Automated design of specificity in molecular recognition" *Nat. Struct. Biol.* 10(1):45-52 (Feb. 2003).

Hodgson et al., "The synthesis of peptides and proteins containing non-natural amino acids" *Chem Soc Rev.* 33(7):422-430 (2004).

Hu et al., "Crystal structure of a UBP-family deubiquitinating enzyme in isolation and in complex with ubiquitin aldehyde" *Cell* 111:1041-1054 (Dec. 27, 2002).

Humphris et al., "Design of Multi-Specificity in Protein Interfaces" *PLoS Compt Biol.* 3(8 Suppl e164):1591 (Aug. 2007).

Hussain et al., "DUBs and Cancer. The Role of Deubiquitinating Enzymes as Oncogenes, Non-Oncogenes and Tumor Suppressors" *Cell Cycle* 8:1688-1697 (Jun. 1, 2009).

International Search Report mailed on Oct. 2, 2012, for PCT Application No. PCT/US2012/043177, filed on Jun. 19, 2012, five pages.

James et al., "Antibody Multispecificity mediated by conformational diversity" *Science* 299:1362-1367 (Feb. 2003).

Jeong et al., "Lethality and centrality in protein networks" *Nature* 411:41-42 (2001).

(56) References Cited

OTHER PUBLICATIONS

Jespers et al., "Surface Expression and Ligand-Based Selection of cDNAs Fused to Filamentous Phage Gene VI" *Bio-Technol* 13:378-382 (Apr. 1995).
Jiang et al., "Display of a PorA peptide from Neisseria meningitidis on the bacteriophage T4 capsid surface" *Infect Immun* 65(11):4770-4777 (Nov. 1997).
Kang et al., "Antibody redesign by chain shuffling from random combinatorial immunoglobulin libraries" *Proc. Natl. Acad. Sci. USA* 88:11120-11123 (1991).
Kleckner et al., "GUARDD: User-friendly MATLAB software for rigorous analysis of CPMG RD NMR data," *J. Mol. Biol.* 52:11-22 (2012).
Komander et al., "Breaking the chains: Structure and Function of the Deubiquitinases" *Nature Review/Molecular Cell Biology* 10:550-563 (Aug. 2009).
Komander et al., "The emerging complexity of protein ubiquitination" *Biochem. Soc. Trans.* 37:937-953 (2009).
Kuhlman et al., "Design of a novel globular protein fold with atomic-level accuracy" *Science* 302(5649):1364-1368 (Nov. 21, 2003).
Kunkel et al., "Rapid and efficient site-specific mutagenesis without phenotypic selection" *Method Enzymol* 154:367-382 (1987).
Lange et al., "Recognition dynamics up to microseconds revealed from an RDC-derived ubiquitin ensemble in solution" *Science* 320:1471-1475 (Jun. 13, 2008).
Larsen et al., "Substrate binding and catalysis by ubiquitin C-terminal hydrolases: identification of two active site residues" *Biochemistry* 35:6735-6744 (1996).
Leaver-Fay et al., "Rosetta3: An object-oriented software suite for the simulation and design of macromolecules" *Methods in Enzymology* 487:545-574 (2011).
Lee et al., "Enhancement of proteasome activity by a small-molecule inhibitor of USP14" *Nature* 467:179-184 (2010).
Levine et al., "Optimizing the affinity and specificity of proteins with molecular display" *Mol. Biosyst.* 2(1):49-57 (Jan. 2006).
Li et al., "Filamentous bacteriophage display of a bifunctional protein A::scFv fusion" *Mol Biotech* 9:187-193 (1998).
Li et al., "A dynamic role of HAUSP in the p53-Mdm2 pathway" *Molecular Cell* 13:879-886 (Mar. 26, 2004).
Lipovsek et al, "In-vitro protein evolution by ribosome display and mRNA display" *Immunol Methods* 290(1-2):51-67 (Apr. 2004).
Long et al. "In silico elucidation of the recognition dynamics of ubiquitin," *PLoS One* 7(4 Suppl e1002035): pp. 1-9 (Apr. 2011).
Low et al., "Mimicking somatic hypermutation: affinity maturation of antibodies displayed on bacteriophage using a bacterial mutator strain" *J. Mol. Biol.* 260(3):359-368 (Jul. 19, 1996).
Lowman et al., "Selecting high-affinity binding proteins by monovalent phage display" *Biochemistry-US* 30(45):10832-10838 (1991).
Lowman and Wells, "Affinity maturation of human growth hormone by monovalent phage display" *J. Mol. Biol.* 234:564-578 (1993).
Luchansky et al., "Substrate recognition and catalysis by UCH-L1" *Biochemistry* 45:14717-14725 (2006).
Marks et al., "By-passing immunization. Human antibodies from V-gene libraries displayed on phage" *J Mol Biol* 222:581-597 (1991).
Massi et al., "Microsecond timescale backbone conformational dynamics in ubiquitin studied with NMR R1rho relaxation experiments" *Protein Sci.* 14:735-742 (2005).
Matsumoto et al., "K11-linked polyubiquitination in cell cycle control revealed by a K11 linkage-specific antibody" *Mol Cell* 39(3):477-84 (Aug. 2010).
Matsumoto et al., "Engineering and Structural Characterization of a Linear Polyubiquitin-Specific Antibody" *Journal of Molecular Biology* 418:134-144 (2012).
Mulder et al., "Measurement of Slow (μs—ms) Time Scale Dynamics in Protein Side Chains by 15N Relaxation Dispersion NMR Spectroscopy: Application to Asn and Gln Residues in a Cavity Mutant of T4 Lysozyme" *J Am Chem Soc* 123:967-975 (2001).

Murakami et al., "Cell Cycle Regulation, Oncogenes, and Antineoplastic Drugs" The Molecular Basis of Cancer., Mendelsohn and Israel, eds, Philadelphia:WB Saunders, Chapter 1, pp. 3-17 (1995).
Needels et al., "Generation and Screening of an Oligonucleotide-Encoded Synthetic Peptide Library" *Proc. Natl. Acad. Sci. USA* 90:10700-10704 (Nov. 15, 1993).
Newton et al., "Using linkage-specific monoclonal antibodies to analyze cellular ubiquitylation" *Methods Mol Biol* 832:185-196 (2012).
Nicholson et al. "The Multifaceted Roles of USP7: New Therapeutic Opportunities" *Cell Biochem Biophys* 60:61-68 (2011).
Nicolaou et al., "Calicheamicin 0: A rationally designed molecule with extremely potent and selective DNA cleaving properties and apoptosis Inducing activity." *Agnew Chem Intl Ed Engl* 33(2):183-186 (1994).
Nishimiya et al., "Thermodynamic consequences of grafting enhanced affinity toward the mutated antigen onto an antibody. The case of anti-lysozyme antibody, HyHEL-10" *J. Biol. Chem* 275(17):12813-12830 (Apr. 28, 2000).
Ovaa., "Active-site directed probes to report enzymatic action in the ubiquitin proteasome system" *Nat Rev Cancer* 7:613-620 (2007).
Palmer et al., "Nuclear magnetic resonance methods for quantifying microsecond-to-millisecond motions in biological macromolecules" *Meth. Enzymol.* 339:204-238 (2001).
Perkins et al., "Probability-based protein identification by searching sequence databases using mass spectrometry data" *Electrophoresis* 20:3551-3567 (1999).
Pickart., "Mechanisms underlying ubiquitination" *Annu Rev Biochem* 70:503-533 (2001).
Pickart and Fushman., "Polyubiquitin chains: polymeric protein signals" *Curr Opin Chem Biol* (e-pub Oct. 28, 2004), 8(6):610-616 (Dec. 2004).
Ren et al., "Phage display of intact domains at high copy number: A system based on SOC, the small outer capsid protein of bacteriophage T4" *Protein Sci* 5:1833-1843 (1996).
Ren et al. "Cloning of linear DNAs in vivo by overexpressed T4 DNA ligase: construction of a T4 phage hoc gene display vector" *Gene* 195(2):303-311 (Aug. 22, 1997).
Ren et al., "Phage T4 SOC and HOC display of biologically active, full-length proteins on the viral capsid" *Gene* 215:439-444 (1998).
Renatus et al., "Structural basis of ubiquitin recognition by the deubiquitinating protease USP2" *Structure* 14:1293-1302 (2006).
Reyes-Turcu et al., "The ubiquitin binding domain ZnF UBP recongnizes the c-terminal diglycine motif of unanchored ubiquitin" *Cell* 124:1197-1208 (Mar. 24, 2008).
Rizk et al., "Allosteric control of Ligand-Binding Affinity Using Engineered Conformation-Specific Effector Proteins" *Nature Structural & Biology* 18(4):437-444 (Apr. 2011).
Sandberg et al., "New chemical descriptors relevant for the design of biologically active peptides. A multivariate characterization of 87 amino acids" *J Med Chem.* 41(14):2481-91 (1998).
Schlapschy et al., "Functional humanization of an anti-CD30 Fab fragment for the immunotherapy of Hodgkin's lymphoma using an in vitro evolution approach" *Protein Eng. Des. Sel.* 17(12):847-860 (Dec. 2004).
Schoofs et al., "Epitopes of an influenza viral peptide recognized by antibody at single amino antiacid resolution" *J Immunol* 140:611-616 (1988).
Scott et al., "Searching for peptide ligands with an epitope library" *Science* 249:386-390 (1990).
Shen et al., "Consistent blind protein structure generation from NMR chemical shift data" *Proc. Natl. Acad. Sci. USA* 105(12):4685-4690 (Mar. 25, 2005).
Shi et al., "Ubiquitin becomes ubiquitous in cancer: emerging roles of ubiquitin ligases and deubiquitinases in tumorigenesis and as therapeutic targets" *Cancer Biol. Ther.* 10:737-747 (2010).
Siebenlist et al. et al., "E. coli RNA polymerase interacts homologously with two different promoters" *Cell* 20:269-281 (Jun. 1980).
Skelton et al., "Origins of PDZ domain ligand specificity. Structure determination and mutagenesis of the Erbin PDZ domain" *J Biol Chem.* 278(9):7645-7654 (Feb. 28, 2003).

(56) References Cited

OTHER PUBLICATIONS

Smith and Scott et al., "Libraries of peptides and proteins displayed on filamentous phage" *Method Enzymol* 217:228-257 (1993).

Smith, G. P., "Surface presentation of protein epitopes using bacteriophage expression systems" *Curr Opin Biotechnol* 2(5):668-673 (1991).

Smith and Kortemme, "Predicting the tolerated sequences for proteins and protein interfaces using rosettabackrub flexible backbone design," *PLoS One* 6(7)(e20451):1-11 (Jul. 2011).

Spence et al. et al., "A ubiquitin mutant with specific defects in DNA repair and multiubiquitination" *Mol Cell Biol* 15(3):1265-1273 (Mar. 1995).

Stella and Himmelstein., *Directed Drug Delivery* "Prodrugs: A chemical approach to targeted drug delivery," Bochardt et al., Humana Press 247-267 (1985).

Tollinger et al., "Slow dynamics in folded and unfolded states of an SH3 domain" *J. Am. Chem. Soc.* 123(46):11341-11352 (Nov. 21, 2001).

Tonikian et al., "Identifying specificity profiles for peptide recognition modules from phage-displayed peptide libraries" *Nat Protoc.* 2(6):1368-86 (2007).

Vedadi et al., "Chemical screening methods to identify ligands that promote protein stability, protein crystallization, and structure determination" *Proc. Natl. Acad. Sci. USA* 103(43):15835-15840 (Oct. 24, 2006).

Wertz et al., "De-ubiquitination and ubiquitin ligase domains of A20 downregulate NF-kappaB signalling" *Nature* 430:694-699 (Aug. 5, 2004).

Wilman, D. E. V., "Prodrugs in cancer chemotherapy biochemical society transactions," 615th Meeting, Belfast, Ireland, pp. 375-382 (1986).

Wlodarski, et al., "Conformational selection and induced fir mechanism underlie specificity in noncovalent interactions with ubiquitin" *Proc. Natl. Acad. Sci. U.S.A* 106:19346-19351 (2009).

Wu et al., "Stepwise in vitro affinity maturation of Vitaxin, an $\alpha_v \beta_{3\text{-}specific\ humanized\ mAb}$" *P Natl Acad Sci USA* 95(11):6037-6042 (May 26, 1998).

Xie et al., "Adding amino acids to the genetic repertoire" *Curr Opin Chem Biol.* 9(6):548-54 (2005).

Yang et al., "CDR walking mutagenesis for the addinity maturation of a potent human anti-HIV-1 antibody into the picomolar range" *J Mol Biol* 254(3):392-403 (Dec. 1, 1995).

Yuan et al., "USP10 Regulates p53 Localization and Stability by Deubiquitinating p53" *Cell* 140:384-396 (Feb. 5, 2010).

Zhu et al., "Inhibition of vascular endothelial growth factor-induced receptor activation with anti-kinase insert domain-containing receptor single-chain antibodies from a phage display library" *Cancer Res* 58(15):3209-3214 (Aug. 1, 1998).

\* cited by examiner

| No. unique peptides |
|---|
| 0 |
| 1-5 |
| 6-10 |
| 10-15 |
| 16-20 |
| 21-30 |
| 31-40 |
| 41-50 |
| 51-60 |
| 61-70 |

| cell line | HEK293T | | WT HCT116 | | HCT116 U7-/- | |
|---|---|---|---|---|---|---|
| HA-Ub | UbAGG | U7AMAGG | UbAGG | U7AMAGG | UbAGG | U7AMAGG |
| USP DUBs | | | | | | |
| USP3 | 0 (0) | 11 (9) | 0 (0) | 9 (9) | 0 (0) | 0 (0) |
| USP5 | 5 (5) | 0 (0) | 16 (16) | 15 (13) | 0 (0) | 4 (3) |
| USP7 | 4 (4) | 21 (21) | 6 (6) | 23 (22) | 0 (0) | 0 (0) |
| USP8 | 1 (1) | 0 (0) | 3 (3) | 0 (0) | 0 (0) | 0 (0) |
| USP9X | 40 (38) | 29 (28) | 12 (11) | 13 (9) | 0 (0) | 10 (10) |
| USP10 | 6 (6) | 0 (0) | 8 (8) | 6 (6) | 0 (0) | 2 (2) |
| USP11 | 4 (4) | 0 (0) | 10 (10) | 4 (3) | 0 (0) | 6 (6) |
| USP13 | 0 (0) | 2 (2) | 1 (1) | 0 (0) | 0 (0) | 0 (0) |
| USP14 | 4 (3) | 0 (0) | 3 (3) | 3 (3) | 0 (0) | 0 (0) |
| USP15 | 1 (1) | 5 (5) | 7 (7) | 6 (6) | 0 (0) | 4 (4) |
| USP19 | 54 (32) | 0 (0) | 65 (65) | 0 (0) | 0 (0) | 0 (0) |
| USP22 | 0 (0) | 20 (19) | 1 (1) | 2 (2) | 0 (0) | 1 (1) |
| USP24 | 20 (19) | 2 (2) | 34 (32) | 0 (0) | 0 (0) | 0 (0) |
| USP25 | 2 (2) | 0 (0) | 0 (0) | 1 (1) | 0 (0) | 1 (1) |
| USP28 | 0 (0) | 1 (1) | 0 (0) | 1 (1) | 0 (0) | 0 (0) |
| USP32 | 1 (1) | 26 (24) | 0 (0) | 0 (0) | 0 (0) | 1 (1) |
| USP47 | 2 (2) | 1 (1) | 0 (0) | 0 (0) | 0 (0) | 0 (0) |
| USP48 | 0 (0) | 0 (0) | 0 (0) | 0 (0) | 0 (0) | 0 (0) |
| UCH DUBs | | | | | | |
| UCHL1 | 3 (3) | 0 (0) | 0 (0) | 0 (0) | 0 (0) | 0 (0) |
| UCHL3 | 0 (0) | 0 (0) | 0 (0) | 0 (0) | 0 (0) | 1 (1) |
| UCHL5 | 9 (9) | 7 (7) | 6 (6) | 7 (7) | 0 (0) | 0 (0) |
| OTU DUBs | | | | | | |
| OTUB1 | 9 (7) | 13 (8) | 10 (7) | 17 (7) | 0 (0) | 8 (6) |
| VCPIP1 | 0 (0) | 0 (0) | 0 (0) | 0 (0) | 0 (0) | 1 (1) |
| JAMM DUB | | | | | | |
| BRCC36 | 0 (0) | 1 (1) | 1 (1) | 2 (2) | 0 (0) | 0 (0) |

Figure 17

| clone name | 40 | 42 | 46 | 47 | 49 | 62 | 65 | 68 | 70 | 72 | 73 | 74 | 75 | 76 | S/N | signal |
|---|---|---|---|---|---|---|---|---|---|---|---|---|---|---|---|---|
| Ub7.25.206 | Q | R | L | G | Q | G | A | H | V | R | A | S | A | R | 35.5 | 2.80 |
| Ub7.25.207 | Q | R | A | G | Q | G | S | H | V | W | R | R | G | S | 38.4 | 2.88 |
| Ub7.25.216 | Q | M | A | G | V | Q | S | H | R | W | K | V | R | V | 49.6 | 3.25 |
| Ub7.25.268 | Q | R | A | G | L | Q | S | Q | V | W | K | R | P | A | 50.8 | 3.39 |
| Ub7.25.225 | Q | R | A | G | Y | Q | S | H | V | R | K | G | E | R | 54.5 | 3.59 |
| Ub7.25.226 | Q | R | N | G | Y | Q | S | H | V | R | R | Y | V | L | 54.5 | 3.53 |
| Ub7.25.227 | Q | R | A | G | Q | Q | S | H | V | W | R | S | H | G | 51.4 | 3.68 |
| Ub7.25.238 | Q | R | A | G | T | R | S | H | V | H | K | S | Y | A | 50.9 | 3.25 |
| Ub7.25.251 | Q | R | A | G | Q | Q | S | H | V | W | K | W | V | S | 39.7 | 2.90 |

Columns labeled "residue number"

SEQUENCE LISTING

```
<160> NUMBER OF SEQ ID NOS: 20

<210> SEQ ID NO 1
<211> LENGTH: 76
<212> TYPE: PRT
<213> ORGANISM: Unknown
<220> FEATURE:
<223> OTHER INFORMATION: Description of Unknown: Wildtype Ubiquitin
      sequence

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 5
<212> TYPE: PRT
<213> ORGANISM: Unknown
<220> FEATURE:
<223> OTHER INFORMATION: Description of Unknown: Wildtype Ubiquitin
      sequence

<400> SEQUENCE: 3

Arg Leu Arg Gly Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

```
Arg Ala Ser Ala Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Arg Arg Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp Lys Val Arg Val
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Lys Arg Pro Ala
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Lys Gly Glu Arg
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Arg Tyr Val Leu
1               5

<210> SEQ ID NO 10
<211> LENGTH: 5
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 10

Trp Arg Ser His Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Lys Ser Tyr Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Lys Trp Val Ser
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 13

His His His His His
1               5

<210> SEQ ID NO 14
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gctagcgccg ccaccatgga gtacccatac gacgtaccag attacgctta cccatacgac      60
gtaccagatt acgcttaccc atacgacgta ccagattacg ctaagctt                  108

<210> SEQ ID NO 15
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(8)
<223> OTHER INFORMATION: Any amino acid
<220> FEATURE:

<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (69)..(69)
<223> OTHER INFORMATION: Any amino acid
<220> FEATURE:
<221> NAME/KEY: MOD_RES
<222> LOCATION: (71)..(71)
<223> OTHER INFORMATION: Any amino acid

<400> SEQUENCE: 15

Met Gln Ile Phe Val Lys Xaa Xaa Thr Gly Lys Thr Xaa Thr Leu Glu
1               5                   10                  15

Val Glu Pro Ser Asp Thr Ile Glu Asn Val Lys Ala Lys Ile Gln Asp
            20                  25                  30

Lys Xaa Gly Xaa Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Xaa Val Xaa Arg Leu Arg Gly Gly
65                  70                  75

<210> SEQ ID NO 16
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (71)..(71)
<223> OTHER INFORMATION: Any amino acid

<400> SEQUENCE: 16

Met Gln Ile Phe Val Lys Cys Cys Thr Gly Lys Thr Xaa Thr Leu Glu
1               5                   10                  15

Val Glu Pro Ser Asp Thr Ile Glu Asn Val Lys Ala Lys Ile Gln Asp
            20                  25                  30

Lys Xaa Gly Xaa Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Cys Val Xaa Arg Leu Arg Gly Gly
65                  70                  75

```
<210> SEQ ID NO 17
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Asn, Arg, Gly, Lys, Tyr, Ala, Ser, His, Glu,
      Leu, Thr, Val, Ile, Met or Pro
<220> FEATURE:
<221> NAME/KEY: MOD_RES
<222> LOCATION: (34)..(34)
<223> OTHER INFORMATION: Ile, Phe, Leu, Val, Ser, Met or Thr
<220> FEATURE:
<221> NAME/KEY: MOD_RES
<222> LOCATION: (36)..(36)
<223> OTHER INFORMATION: Tyr, Phe, Leu, His, Ala, Val, Trp, Ile, Met or
      Asn
<220> FEATURE:
<221> NAME/KEY: MOD_RES
<222> LOCATION: (71)..(71)
<223> OTHER INFORMATION: Arg, Lys, Ala, Gln, Trp, Gly, His or Ile

<400> SEQUENCE: 17

Met Gln Ile Phe Val Lys Cys Cys Thr Gly Lys Thr Xaa Thr Leu Glu
1               5                   10                  15

Val Glu Pro Ser Asp Thr Ile Glu Asn Val Lys Ala Lys Ile Gln Asp
            20                  25                  30

Lys Xaa Gly Xaa Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Cys Val Xaa Arg Leu Arg Gly Gly
65                  70                  75

<210> SEQ ID NO 18
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Asp, Phe, Arg or Ser
<220> FEATURE:
<221> NAME/KEY: MOD_RES
<222> LOCATION: (8)..(8)
<223> OTHER INFORMATION: Tyr, Ala, Gly, Gln or Arg
<220> FEATURE:
<221> NAME/KEY: MOD_RES
<222> LOCATION: (13)..(13)
<223> OTHER INFORMATION: Arg, Tyr, Glu or Pro
<220> FEATURE:
<221> NAME/KEY: MOD_RES
<222> LOCATION: (34)..(34)
<223> OTHER INFORMATION: Ile, Leu or Thr
<220> FEATURE:
<221> NAME/KEY: MOD_RES
<222> LOCATION: (36)..(36)
<223> OTHER INFORMATION: Leu, Tyr, Ala or Asn
<220> FEATURE:
<221> NAME/KEY: MOD_RES
<222> LOCATION: (69)..(69)
<223> OTHER INFORMATION: Ala, Gly, Trp, Lys, Tyr or Ile
<220> FEATURE:
<221> NAME/KEY: MOD_RES
<222> LOCATION: (71)..(71)
```

<223> OTHER INFORMATION: Ala, Arg, Gln or Gly

<400> SEQUENCE: 18

Met Gln Ile Phe Val Lys Xaa Xaa Thr Gly Lys Thr Xaa Thr Leu Glu
1               5                   10                  15

Val Glu Pro Ser Asp Thr Ile Glu Asn Val Lys Ala Lys Ile Gln Asp
            20                  25                  30

Lys Xaa Gly Xaa Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Xaa Val Xaa Arg Leu Arg Gly Gly
65                  70                  75

<210> SEQ ID NO 19
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (42)..(42)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (49)..(49)
<223> OTHER INFORMATION: Any amino acid
<220> FEATURE:
<221> NAME/KEY: MOD_RES
<222> LOCATION: (62)..(62)
<223> OTHER INFORMATION: Any amino acid
<220> FEATURE:
<221> NAME/KEY: MOD_RES
<222> LOCATION: (65)..(65)
<223> OTHER INFORMATION: Any amino acid
<220> FEATURE:
<221> NAME/KEY: MOD_RES
<222> LOCATION: (68)..(71)
<223> OTHER INFORMATION: Any amino acid

<400> SEQUENCE: 19

Met Gln Ile Phe Val Lys Xaa Xaa Thr Gly Lys Thr Xaa Thr Leu Glu
1               5                   10                  15

Val Glu Pro Ser Asp Thr Ile Glu Asn Val Lys Ala Lys Ile Gln Asp
            20                  25                  30

Lys Xaa Gly Xaa Pro Pro Asp Gln Gln Xaa Leu Ile Phe Xaa Gly Lys
        35                  40                  45

```
Xaa Leu Glu Asp Gly Arg Thr Leu Ser Asp Tyr Asn Ile Xaa Lys Glu
    50                  55                  60

Xaa Thr Leu Xaa Xaa Xaa Xaa Arg Leu Arg Gly Gly
65              70                  75
```

<210> SEQ ID NO 20
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (42)..(42)
<223> OTHER INFORMATION: Any amino acid
<220> FEATURE:
<221> NAME/KEY: MOD_RES
<222> LOCATION: (46)..(47)
<223> OTHER INFORMATION: Any amino acid
<220> FEATURE:
<221> NAME/KEY: MOD_RES
<222> LOCATION: (49)..(49)
<223> OTHER INFORMATION: Any amino acid
<220> FEATURE:
<221> NAME/KEY: MOD_RES
<222> LOCATION: (62)..(62)
<223> OTHER INFORMATION: Any amino acid
<220> FEATURE:
<221> NAME/KEY: MOD_RES
<222> LOCATION: (65)..(65)
<223> OTHER INFORMATION: Any amino acid
<220> FEATURE:
<221> NAME/KEY: MOD_RES
<222> LOCATION: (68)..(76)
<223> OTHER INFORMATION: Any amino acid

<400> SEQUENCE: 20

```
Met Gln Ile Phe Val Lys Xaa Xaa Thr Gly Lys Thr Xaa Thr Leu Glu
1               5                   10                  15

Val Glu Pro Ser Asp Thr Ile Glu Asn Val Lys Ala Lys Ile Gln Asp
                20                  25                  30

Lys Xaa Gly Xaa Pro Pro Asp Xaa Gln Xaa Leu Ile Phe Xaa Xaa Lys
            35                  40                  45

Xaa Leu Glu Asp Gly Arg Thr Leu Ser Asp Tyr Asn Ile Xaa Lys Glu
    50                  55                  60

Xaa Thr Leu Xaa Xaa Xaa Xaa Xaa Xaa Xaa Xaa
65                  70                  75
```

ENGINEERED CONFORMATIONALLY-STABILIZED PROTEINS

RELATED APPLICATIONS

This application claims priority from U.S. Provisional Patent Application No. 61/612,228, filed Mar. 16, 2013, and U.S. Provisional Patent Application No. 61/663,504, filed Jun. 22, 2012, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Jun. 25, 2013, is named P4865R1US_SL.txt and is 11,438 bytes in size.

TECHNICAL FIELD

Provided herein are methods for screening for and using conformationally stabilized forms of a conformationally dynamic protein, such as a conformationally stabilized ubiquitin protein, as well as compositions comprising the same.

BACKGROUND

Proteins are remarkably dynamic macromolecules, with conformational motions that play roles in diverse processes such as generating mechanical work, carrying out enzymatic reactions, and mediating signal transduction. Since the various states of a molecule may potentiate different functions, there is considerable interest in the ability to generate reagents that specifically recognize discrete conformational states.[1,2]

Ubiquitin is a small regulatory protein that is found in almost all tissues (ubiquitously) in eukaryotic organisms. Protein ubiquitination mediates numerous cellular processes, such as cell cycle control, apoptosis, epigenetics, and transcriptional regulation.[4] However, ubiquitin is perhaps best known for the role it plays in the labeling of proteins that are to be destroyed and recycled by a cell's proteolytic machinery. When a protein is covalently "tagged" by ubiquitin, the ubiquitin molecule directs the protein to the proteasome, which is a large multi-component protein complex in the cell that degrades and recycles proteins tagged for destruction. The ubiquitin protein itself consists of 76 amino acids with a molecular mass of about 8.5 kDa. Key features include its C-terminal tail and seven lysine residues.[6] The amino acid sequence of ubiquitin is highly conserved among eukaryotic species, with human and yeast ubiquitin sharing approximately 96% sequence identity. In mammals, ubiquitin is encoded by four separate genes. The genes UBA52 and RPS27A encode a single copy of ubiquitin fused to the ribosomal proteins L40 and S27a, respectively, whereas the UBB and UBC genes encode the polyubiquitin precursor proteins.

Ubiquitination is an enzymatic, post-translational modification process in which the terminal glycine from the ubiquitin C-terminal di-glycine motif in activated ubiquitin forms an amide bond to the epsilon amine of a lysine residue in a modified protein. Ubiquitin is activated in a two-step reaction by an E1 ubiquitin-activating enzyme in a process requiring ATP as an energy source. This involves production of an ubiquitin-adenylate intermediate followed by the transference of ubiquitin to the E1 active site cysteine residue, resulting in a thioester linkage between the C-terminal carboxyl group of ubiquitin and the E1 cysteine sulfhydryl group. Next, ubiquitin is transferred from the E1 enzyme to the active site cysteine of an E2 ubiquitin-conjugating enzyme via a trans(thio)esterification reaction. The final step of the ubiquitination enzyme cascade creates an isopeptide bond between a lysine in the target protein and the C-terminal glycine of ubiquitin. In general, this step requires the activity of one of the hundreds of known E3 ubiquitin-protein ligases (often termed simply "ubiquitin ligase").[5] E3 enzymes function as the substrate recognition modules of the system and are capable of interaction with both E2 and the modified protein substrate.

Following the addition of a single ubiquitin to a protein (monoubiquitination), further ubiquitin proteins can be added to the first ubiquitin molecule on one or more of its seven lysine residues, yielding a polyubiquitin chain. In addition, some substrates are modified by the addition of ubiquitin molecules to multiple lysine residues in a process termed multiubiquitination. The most studied polyubiquitin chains—lysine-48-linked—target proteins for proteolysis in the proteosome. The condemned protein must be modified by at least four ubiquitin molecules in order for it to be recognized by the cell's proteolytic machinery. Ubiquitin molecules are cleaved off the protein immediately prior to destruction and are recycled for further use by enzymes belonging to the ubiquitin C-terminal hydrolase (UCH) family of deubiquitinases.

Deubiquitinases (DUBs) are a class of specialized proteases that regulate ubiquitin-mediated signaling by disassembling ubiquitin chains or removing monoubiquitination from substrates.[7] DUBs are also commonly referred to as deubiquitinating peptidases, deubiquitinating isopeptidases, deubiquitinases, ubiquitin proteases, ubiquitin hydrolyases, ubiquitin isopeptidases, or DUbs. The human genome encodes nearly 100 DUBs with specificity for ubiquitin in five gene families. DUBs may act as negative and positive regulators of the ubiquitin system. In addition to ubiquitin recycling, they are involved in the initial processing of ubiquitin precursors, in the proofreading of protein ubiquitination, and in disassembly of inhibitory ubiquitin chains. Additionally, DUBs such as the ubiquitin specific protease (USP) family of DUBs reverse the ubiquitination or ubiquitin-like modification of target proteins while DUBs such as members of the UCH family of DUBs are responsible for the regeneration of monoubiquitin from unanchored polyubiquitin, i.e., free polyubiquitin that is synthesized de novo by the conjugating machinery or that has been released from target proteins by other DUBs.

The majority of DUBs have yet to be extensively characterized. One exception is USP7 (HAUSP), which has a well-established role in tumorigenesis. A critical function of USP7 is to regulate cell survival by deubiquitinating and stabilizing the oncoprotein Mdm2, thereby downregulating the p53 tumor suppressor.[8,9] Since USP7 indirectly destabilizes p53 and regulates additional tumor suppressors, including FOXO4 and PTEN, inhibition of USP7 is an attractive therapeutic strategy.[8,9] Another example is USP14, which is thought to play a role in degradation of proteins involved in amyloidogenic neurodegeneration.[32]

All patents, patent applications, publications, documents, nucleotide and protein sequence database accession numbers, the sequences to which they refer, and articles cited herein are all incorporated herein by reference in their entireties.

SUMMARY

The invention provided herein discloses, inter alia, compositions comprising conformationally stabilized ubiquitin proteins and methods for using the same to inhibit the action of one or more enzymes which bind to the stabilized form of these proteins as well as methods for identifying agents which bind to these stabilized proteins. Also provided herein are methods for screening for a conformationally stabilized form of a protein.

The present application in one aspect provides a conformationally stabilized ubiquitin protein comprising one or more amino acid substitutions relative to a wild-type ubiquitin protein. In some embodiments, said one or more amino acid substitutions stabilize(s) the β1/β2 loop of the conformationally stabilized ubiquitin protein such that the β1/β2 loop is confined to a region within about 1.6 Å root mean square deviation of Protein Data Bank code 3NHE chain B. In some embodiments, the β1/β2 loop region of the conformationally stabilized ubiquitin protein exhibits slower conformational dynamics in comparison to wildtype ubiquitin protein as measured by NMR $R_2$ dispersion. In some embodiments of any of the embodiments described above, the microsecond $R_{ex}$ values in the region around the β1/β2 loop of the conformationally stabilized ubiquitin protein are up to 40 fold greater in comparison to wildtype ubiquitin protein as measured by NMR $R_2$ dispersion. In some embodiments of any of the embodiments described above, said conformationally stabilized ubiquitin protein comprises one or more amino acid substitutions at a position selected from the group consisting of A7, A8, A13, A34, A36, A69, and A71, wherein the position is relative to A1-A76 (SEQ ID NO:1). In some embodiments, the conformationally stabilized ubiquitin protein comprises (a) substitution A7 (C) or a substitution A8 (C); and (b) substitution A69 (C). In some embodiments, the conformationally stabilized ubiquitin protein further comprises one or more substitutions selected from the group consisting of A13 (N, R, G, K, Y, A, S, H, E, L, T, V, I, M, or P), A34 (I, F, L, V, S, M, or T), A36 (Y, F, L, H, A, V, W, I, M or N), and A71 (R, K, A, Q, W, G, H, I, R or G). In some embodiments, the conformationally stabilized ubiquitin protein comprises one or more substitutions selected from the group consisting of A7(D, F, R, or S), A8 (Y, A, G, Q, R, or Y), A13 (R, Y, E, or P), A34 (I, L, or T), A36 (L, Y, A, or N), A69 (A, G, W. K. Y, or I), and A71 (A, R, Q, R, or G). In some embodiments of any of the embodiments described above, the conformationally stabilized ubiquitin protein further comprises one or more amino acid substitutions located at A42, A46, A49, A62, A65, A68, or A70, wherein the amino acid residue positions correspond to the positions in SEQ ID NO:1. In some embodiments of any of the embodiments described above, the conformationally stabilized ubiquitin protein further comprises one or more amino acid substitutions located at A40, A42, A46, A47, A49, A62, A65, A68, A70, A71, A72, A73, A74, A75, or A76, wherein the amino acid residue positions correspond to the positions in SEQ ID NO:1. In some embodiments of any of the embodiments described above, the conformationally stabilized ubiquitin protein exhibits increased binding to a deubiquitinase of the Ubiquitin Specific Protease (USP) family compared to the wild-type ubiquitin protein. In some embodiments of any of the embodiments described above the conformationally stabilized ubiquitin protein binds to the deubiquitinase with a Kd in the nanomolar range. In some embodiments of any of the embodiments described above, the conformationally stabilized ubiquitin protein binds to the deubiquitinase with an affinity that is at least 1000 fold higher than that of the wild-type protein. In some embodiments of any of the embodiments described above, the conformationally stabilized ubiquitin protein inhibits the activity of the deubiquitinase. In some embodiments of any of the embodiments described above, the conformationally stabilized ubiquitin protein exhibits no or decreased binding to a deubiquitinase of the Ubiquitin C-terminal Hydrolase (UCH) family compared to wildtype ubiquitin protein.

In one aspect, there is provided a nucleic acid encoding the conformationally stabilized ubiquitin protein of any of the embodiments described above.

In one aspect, there is provided a vector comprising the nucleic acid of any of the embodiments described above. In some embodiments, the vector is an expression vector.

In one aspect, there is provided a cell comprising the nucleic acid or the vector of any of the embodiments described above. In some embodiments, the cell is selected from the group consisting of an animal cell, a bacterial cell, an insect cell, a nematode cell, and a yeast cell. In some embodiments, the animal cell is a human cell or a non-human cell.

In one aspect, there is provided a protein complex comprising the conformationally stabilized ubiquitin protein of any of the embodiments described above and a deubiquitinase of a member of the USP family. In some embodiments, the deubiquitinase is USP7, USP5, or USP14. In some embodiments, the deubiquitinase is USP7.

In one aspect, there is provided a protein covalently linked to one or more of the conformationally stabilized ubiquitin proteins of any one of the embodiments described above.

In one aspect, there is provided a solid support comprising the conformationally stabilized ubiquitin protein of any one of the embodiments described above immobilized thereon. In some embodiments, the solid support is a surface suitable for surface plasmon resonance. In some embodiments, the solid support is a nanoparticle, a bead, or glass.

In one aspect, there is provided a population of cells comprising the conformationally stabilized ubiquitin protein of any one of the embodiments described above expressed on the surface thereof.

In one aspect, there is provided a method of inhibiting a deubiquitinase of the USP family, comprising contacting the deubiquitinase with a conformationally stabilized ubiquitin protein of any one of the embodiments described above. In some embodiments, the inhibition is in vivo or in vitro.

In one aspect, there is provided a method of identifying an agent that binds to a conformational form of the ubiquitin protein that is favorable for binding to a deubiquitinase of the USP family, comprising: a) contacting the agent with a conformationally stabilized ubiquitin protein of any of the embodiments described above; and b) determining whether the agent binds to said conformationally stabilized ubiquitin protein. In some embodiments, the agent is a small molecule chemical compound, an antibody, a protein, an inhibitory nucleic acid, or any combination thereof.

In one aspect, there is provided a method of identifying an agent that binds to a protein complex comprising a deubiquitinase of the USP family and ubiquitin, the method comprising: a) contacting the agent with the protein complex of any of claims 21-23; and b) determining whether the agent is capable of binding to said protein complex. In some embodiments, the agent is a small molecule chemical compound, an antibody, a protein, an inhibitory nucleic acid, or any combination thereof. In some embodiments, the agent disrupts the interaction between the deubiquitinase and the ubiquitin protein.

In one aspect, there is provided an agent identified by the methods of any one of the embodiments described above.

In one aspect, there is provided a method of screening for a conformationally stabilized form of a protein, wherein the conformationally stabilized form has an increased binding affinity to a binding partner or has an increased ability to modulate the activity of the binding partner as compared to the wildtype protein, the method comprising: a) contacting the binding partner with a library of mutant forms of the protein, wherein said library of mutant forms is produced by substituting an amino acid residue in a conformationally dynamic protein with another amino acid residue at one or more preselected locations, wherein said preselected locations are located at the interior of the protein; and b) identifying the conformationally stabilized form based on an binding to the binding partner or an increased ability to modulate the activity of the binding partner as compared to the wildtype protein. In some embodiments, the preselected locations are selected based on the contribution of the amino acid residues at each location to the conformational dynamics within the protein or within a region of the protein. In some embodiments of any of the embodiments described above, said library is a library of nucleic acids encoding said mutant forms of proteins. In some embodiments, said library is phage display library. In some embodiments, a vector for the phage display library is selected from the group consisting of M13 bacteriophage, f1 phage, fd phage, Ike phage, N1 phage, Enterobacteria phage T4, bacteriophage T7, and enterobacteria phage λ. In some embodiments of any of the embodiments described above, the method further comprises mutating one or more amino acid residues at the surface of the identified conformationally stabilized protein by substituting the one or more surface amino acid residues with other amino acid residues and screening for proteins having increased binding affinity or modulating capability in comparison to conformationally stabilized proteins without one or more substituted surface amino acid residues. In some embodiments of any of the embodiments described above, the protein is selected from the group consisting of a G-protein coupled receptor (GPCR), a nuclear hormone receptor, a tyrosine kinase receptor, and a ligand-gated ion channel. In some embodiments, the protein is ubiquitin. In some embodiments, the binding partner is selected from the group consisting of a deubiquitinase, an E1 ubiquitin-activating enzyme, an E2 ubiquitin-conjugating enzyme, an E3 ubiquitin-protein ligase, and one or more members of the cellular proteasome complex. In some embodiments, the binding partner is a deubiquitinase. In some embodiments, the deubiquitinase is a member of the Ubiquitin Specific Protease (USP) family of deubiquitinases. In some embodiments, the deubiquitinase is selected from the group consisting of USP7, USP5, and USP14. In some embodiments, the deubiquitinase is USP7.

DESCRIPTION OF FIGURES

FIG. 17 depicts U7Ub25.2540ΔGG enriches for endogenous USP7 in cellular lysates. The anti-HA immunoprecipitates corresponding to FIG. 14B were analyzed by mass spectrometry. The number of total peptides detected for the indicated DUBs are indicated, with the number of unique peptides shown in parentheses.

FIG. 33 depicts high affinity clones derived from $2^{nd}$ generation of affinity maturation of U7Ub25. The term "s/n ratio" refers to signal:noise ratio, wherein "signal" is the spot phage ELISA signal detected against biotinylated USP7catC223A captured by NeutrAvidin coated on the 384-well Maxisorp plate; "noise" is the ELISA signal against NeutrAvidin alone. The position number in Ubiquitin is indicated. FIG. 33 discloses the sequences encompassing positions 72-76 as SEQ ID NOS 4-12, respectively, in order of appearance.

DETAILED DESCRIPTION

Figure 1:
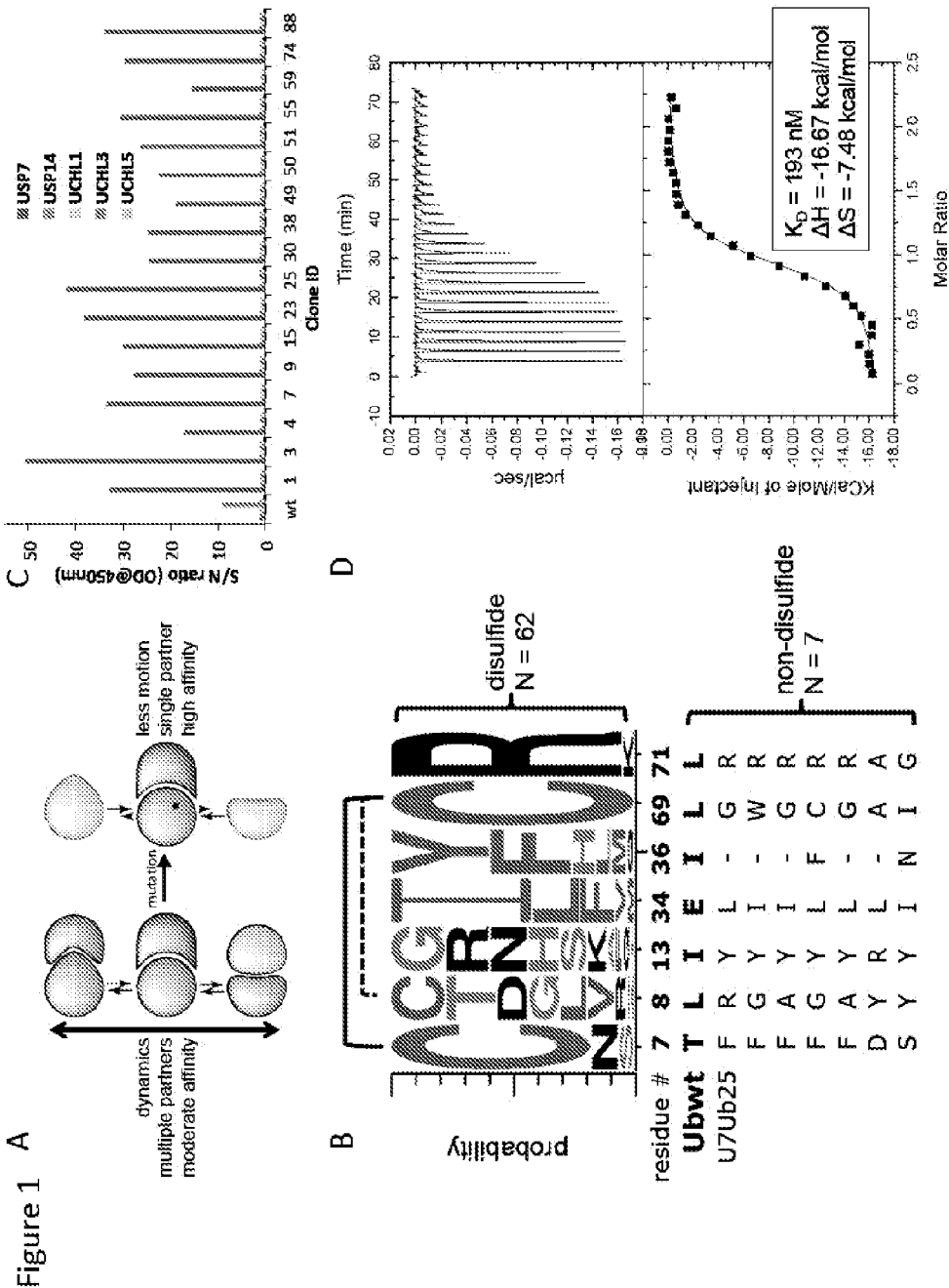
FIG. 1 depicts identification of two types of ubiquitin variants with high affinity for USP7 (U7Ubs) by Conformational Display. A) Conformational Display screens for core mutations that collapse a conformational equilibrium into a single state. In the case of ubiquitin, the pre-existing conformational equilibrium mediates several protein interactions, and selecting for a single conformation is predicted to both reduce the entropic cost of binding and provide specificity. B) Top: Most U7Ubs contain a disulfide bond between positions 7 or 8 and position 69, highlighting how conformational stabilization can be mediated through a covalent intramolecular crosslink. Bottom: a minority of U7Ubs contain no disulfide bonds, achieving the same endpoint through non-covalent repacking. Ubwt (SEQ ID NO: 1) and mutant (SEQ ID NO: 20) sequences with specific residues as shown. C) Both disulfide bond-based (e.g. —clone 7) and non-disulfide bond based (e.g. —clone 25) U7Ubs bind specifically to USP7 by phage spot ELISA. D) The non-disulfide bond U7Ub25 variant binds the catalytic core of USP7 with an affinity of 193±17.3 nM (ΔH=−16.67±0.1562 kcal/mol, ΔS=−7.48 kcal/mol, N=0.92±0.0062).

The present invention provides a method (termed "Conformational Display" (CD)) which can be used to identify and/or screen for conformationally stabilized proteins capable of binding with high affinity to one or more binding partners. In contrast to traditional phage display, which typically mutates surface amino acid positions to find new enthalpic contacts, CD provides a method of altering amino acid residues which are buried within the tertiary structure of a protein to identify new packing arrangements that result in optimal conformations for binding. The methods of the present application differ from what has previously been practiced in the art in that the methods disclosed herein provide the ability to modulate the energetics of a protein's conformational dynamics and thereby represents a means to modulate both the affinity and selectivity of a protein-protein interaction by modulating interface dynamics, rather than only enthalpic contacts.

CD is used to identify conformationally stabilized ubiquitin proteins having amino acid substitutions located in the interior of the ubiquitin protein, thereby altering ubiquitin's β1-β2 loop region into a "down" conformation relative to the predominant conformational state of the wildtype protein. These conformationally stabilized forms of ubiquitin are able to bind to a deubiquitinase of the ubiquitin specific protease (USP) family of deubiquitinases with much higher affinity compared to wildtype ubiquitin. Additionally, the conformationally stabilized ubiquitin proteins produced by CD can be used as novel tools for identifying and screening for one or more agents 1) capable of binding to a specific conformational form of ubiquitin; 2) that binds to an ubiquitin processing enzyme that preferentially binds to a specific conformational form of ubiquitin; or 3) that is capable of disrupting a USP-deubiquitinase/ubiquitin protein complex.

I. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988).

Oligonucleotides, polynucleotides, peptides, polypeptides and small molecules employed or described in the present invention can be generated using standard techniques known in the art.

II. Definitions

"Isolated," when referred to a molecule, refers to a molecule that has been identified and separated and/or recovered from a component of its natural environment. Contaminant components of its natural environment are materials that interfere with diagnostic or therapeutic uses.

As used herein, the term "polypeptides" includes proteins, fragments of polypeptides, and fusion polypeptides.

An "active" polypeptide, or fragments thereof, retains a biological activity of native or naturally-occurring counterpart of the active polypeptide. Biological activity refers to a function mediated by the native or naturally-occurring counterpart of the active polypeptide. For example, binding or protein-protein interaction constitutes a biological activity.

"Affinity" refers to the strength of the sum total of noncovalent interactions between a single binding site of a molecule (e.g., ubiquitin, such as a conformationally stabilized form of ubiquitin) and its binding partner. Unless indicated otherwise, as used herein, "binding affinity" refers to intrinsic binding affinity which reflects a 1:1 interaction between members of a binding pair. The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. In some embodiments, an antibody can be chimeric, human, humanized and/or affinity matured.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The light chains of antibodies from any vertebrate species can be assigned to one of two clearly distinct types, called kappa (κ) and lambda (λ), based on the amino acid sequences of their constant domains.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

An "affinity matured" antibody refers to an antibody with one or more alterations in one or more HVRs, compared to a parent antibody which does not possess such alterations, such alterations resulting in an improvement in the affinity of the antibody for antigen.

An "epitope tagged" polypeptide refers to a chimeric polypeptide fused to a "tag polypeptide". Such tags provide epitopes against which Abs can be made or are available, but do not substantially interfere with polypeptide activity. To reduce anti-tag antibody reactivity with endogenous epitopes, the tag polypeptide is usually unique. Suitable tag polypeptides generally have at least six amino acid residues, usually between about 8 and 50 amino acid residues, preferably between 8 and 20 amino acid residues. Examples of epitope tag sequences include HA from Influenza A virus, GD, and c-myc, poly-His and FLAG.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

As used herein, "motion," or "dynamics" in the context of a protein or a region of a protein, refers to conformational changes in the structure of a protein or a region of a protein.

A "conformationally dynamic protein," as used herein refers to a protein or a region of a protein that is capable of undergoing one or more motions.

"Conformationally stabilized" when used herein refers to and includes any protein or region of a protein that is altered with respect to the wildtype protein such that it undergoes less motion in comparison to the wildtype protein or region of a protein. For example, the extent of conformational stability of a protein backbone can be measured by R$_2$ dispersion experiments (sensitive to motion on millisecond timescales) and/or H$_Z$N$_Z$ R$_{1\rho}$R$_{ex}$ measurements (sensitive to motion on microsecond timscales).

"Conformationally stabilized ubiquitin" when used herein refers to and includes any ubiquitin that exists in one or more conformational states with respect to the motion of the β1/β2 loop region in comparison to the motion of this region in wildtype ubiquitin.

The term "wildtype ubiquitin" refers herein to a native sequence ubiquitin polypeptide. The ubiquitin polypeptide described herein may be that which is isolated from a variety of sources, such as from human tissue types or from another source, or prepared by recombinant or synthetic methods. A "native sequence ubiquitin polypeptide" comprises a polypeptide having the same amino acid sequence as the corresponding ubiquitin polypeptide derived from nature.

An amino acid residue located in the "interior" of a protein, as used herein, means an amino acid residue that is not on the protein's surface. Whether or not an amino acid residue is located on the protein's surface can be determined by, for example, solvent accessibility studies, X-ray crystallography structures, NMR structures, or prediction based on primary amino acid sequence.

A "mutation" includes an amino acid deletion, an amino acid insertion, and an amino acid substitution of at least one amino acid into a defined primary amino acid sequence. In some aspects, mutation of one or more amino acids in a primary amino acid sequence can result in the protein encoded by that amino acid sequence having altered activity or expression levels within a cell. In other aspects, mutation of one or more amino acids (such as a conservative mutation) in a primary amino acid sequence may not result in the protein encoded by that amino acid sequence having substantial changes in activity or expression levels within a cell.

An amino acid "substitution" means that at least one amino acid component of a defined primary amino acid sequence is replaced with another amino acid. As used herein, "a protein comprising a substitution of $A_n$ (x, y, or z)" means a protein comprising an amino acid residue substitution located at position n with respect to a defined amino acid sequence, the wild-type amino acid residue is substituted with x, y, or z.

A "small molecule" refers to a composition that has a molecular weight of for example less than about 5 kD, less than about 4 kD, and less than 0.6 kD.

The term "peptide" generally refers to a contiguous and relatively short sequence of amino acids linked by peptidyl bonds. Typically, but not necessarily, a peptide has a length of about 2 to about 50 amino acids, about 4-40 amino acids, or about 10-30 amino acids. Although the term "polypeptide" generally refers to longer forms of a peptide, the two terms can be and are used interchangeably in some contexts herein.

The terms "amino acid" and "residue" are used interchangeably herein.

A "region" of a polypeptide is a contiguous sequence of 2 or more amino acids. In some embodiments, a region is at least about any of 3, 5, 10, 15 contiguous amino acids. The "C-terminal region" or variants thereof refers to a region of a polypeptide that includes the 1-5 residues located closest to the C-terminus of the polypeptide. The "N-terminal region" or variants thereof refers to a region of a polypeptide that includes the 1-5 residues located closest to the N-terminus of the polypeptide. An "internal" region of a polypeptide refers to a region of a polypeptide that is located neither at the N-terminus of the polypeptide nor at the C-terminus of the polypeptide.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

A "fusion protein" refers to a polypeptide having two portions covalently linked together, where each of the portions is derived from different proteins. The two portions may be linked directly by a single peptide bond or through a peptide linker containing one or more amino acid residues. Generally, the two portions and the linker will be in reading frame with each other and are produced using recombinant techniques.

A "disorder" or "pathological condition" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; lymphoid malignancies; neuronal, glial, astrocytal, hypothalamic, and other glandular, macrophagal, epithelial, stromal, and blastocoelic disorders; and inflammatory, immunologic, and other angiogenesis-related disorders.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenesis agents, apoptotic agents, anti-tubulin agents, and other agents to treat cancer, anti-CD20 antibodies, platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets PDGFR-beta, BlyS, APRIL, BCMA receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery,* Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "growth inhibitory agent" when used herein refers to a compound or composition which inhibits growth of a cell. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer,* Mendelsohn and Israel, eds., Chapter 1, entitled "Cell cycle regulation, oncogenes, and antineoplastic drugs" by Murakami et al., (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

An "effective amount" of an agent, e.g., a pharmaceutical formulation, refers to an amount effective, at dosages and for periods of time necessary, to achieve the desired therapeutic or prophylactic result. A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "package insert" is used to refer to instructions customarily included in commercial packages of therapeutic products, that contain information about the indications, usage, dosage, administration, combination therapy, contraindications and/or warnings concerning the use of such therapeutic products.

As is understood by one skilled in the art, reference to "about" a value or parameter herein includes (and describes)

embodiments that are directed to that value or parameter per se. For example, description referring to "about X" includes description of "X".

It is understood that aspect and embodiments of the invention described herein include "consisting" and/or "consisting essentially of" aspects and embodiments. As used herein, the singular form "a", "an", and "the" includes plural references unless indicated otherwise.

III. Compositions of the Invention

Provided herein are conformationally stabilized ubiquitin proteins having one or more amino acid substitutions relative to the amino acid sequence of wild-type ubiquitin. In some aspects, the conformationally stabilized ubiquitin protein exhibits increased binding affinity to one or more ubiquitin processing enzymes (such as, but not limited to, one or more members of the ubiquitin specific protease (USP) family of deubiquitinases) compared to the binding affinity of wildtype ubiquitin to the ubiquitin processing enzymes. In some aspects, the β1/β2 loop region of the conformationally stabilized ubiquitin protein exhibits slower conformational dynamics in comparison to the dynamics of this region in wildtype ubiquitin as measured by NMR $R_2$ dispersion. Also provided herein are nucleic acids encoding the conformationally stabilized ubiquitin proteins, vectors and cells for expressing and isolating the same, as well as protein complexes comprising conformationally stabilized ubiquitin proteins and binding partners which bind with high affinity to a specific conformational form of ubiquitin.

A. Conformationally Stabilized Ubiquitin Proteins

In some aspects, the conformationally stabilized ubiquitin proteins described herein bind to a binding partner (e.g., a USP family deubiquitinase) with a Kd in the nanomolar range. In some aspects, the conformationally stabilized ubiquitin proteins bind to a binding partner (e.g., a USP family deubiquitinase, such as USP7) with an affinity that is at least 1000 fold higher than that of the wildtype protein. In some aspects, the conformationally stabilized ubiquitin proteins inhibit the activity of one or more ubiquitin processing enzymes or deubiquitinases. In some aspects, the conformationally stabilized ubiquitin proteins exhibit no or decreased binding to a binding partner (e.g., a member of the UCH family of deubiquitinases) as compared to the binding of the wildtype protein.

In some embodiments, the conformationally stabilized ubiquitin proteins disclosed herein have a binding affinity as determined by a Kd to a binding partner (e.g., a USP family deubiquitinase) of less than about any of about 1.0 mM, 500 µM, 100 µM, 50 µM, 25 µM, 10 µM, 5 µM, 1 µM, 900 nM, 800 nM, 700 nM, 600 nM, 500 nM, 400 nM, 300 nM, 200 nM, 150 nM, 100 nM, 90 nM, 80 nM, 70 nM, 60 nM, 50 nM, 45 nM, 40 nM, 35 nM, 30 nM, 25 nM, 20 nM, 15 nM, 10 nM, 5 nM, or 1 nM, inclusive, including any values in between these numbers. In some embodiments the binding partner is an ubiquitin processing enzyme, such as, but not limited to, any E1, E2 or E3 ubiquitin processing enzymes or a deubiquitinase. In some embodiments, the binding partner is a member of the USP family of deubiquitinases (such as, but not limited to, USP7, USP5, and/or USP14). In some embodiments, the binding affinity is determined by any method known in the art, in particular the methods described herein.

In some aspects, the conformationally stabilized ubiquitin proteins described herein bind to a binding partner with a higher affinity compared to the binding of the binding partner to wildtype ubiquitin. In some aspects, the conformationally stabilized ubiquitin binds to a binding partner with at least any of 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 6000, 7000, 8000, 9000, or 10,000, inclusive, including any value in between these numbers, higher fold affinity compared to the binding of the binding partner to wildtype ubiquitin. In some embodiments the binding partner is an ubiquitin processing enzyme, such as, but not limited to, any E1, E2 or E3 ubiquitin processing enzymes or a deubiquitinase. In some embodiments, the binding partner is a member of the USP family of deubiquitinases (such as, but not limited to, USP7, USP5, and/or USP14). In one embodiment, the binding partner is USP7. In some embodiments, the binding fold affinity is determined by any method known in the art, in particular the methods described herein.

In some aspects, the conformationally stabilized ubiquitin proteins provided herein exhibit no or decreased binding to a binding partner as compared to the binding of the wildtype protein. In some embodiments, the conformationally stabilized ubiquitin proteins binds to a binding partner with at least any of 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 6000, 7000, 8000, 9000, or 10,000, inclusive, including any value in between these numbers, decreased fold affinity compared to the binding of the binding partner to wildtype ubiquitin. In some embodiments, the conformationally stabilized ubiquitin proteins binds to a binding partner with at least any of 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, less affinity as compared to the binding of the binding partner to wildtype ubiquitin. In some embodiments, the conformationally stabilized ubiquitin proteins do not bind to the binding partner. In some embodiments the binding partner is an ubiquitin processing enzyme, such as, but not limited to, any E1, E2 or E3 ubiquitin processing enzymes or a deubiquitinase. In some embodiments, the binding partner is a member of the UCH family of deubiquitinases. In some embodiments, the conformationally stabilized ubiquitin proteins provided herein exhibit no or decreased binding to a member of the UCH family of deubiquitinases while at the same time exhibit increased binding to a member of the USP family of deubiquitinases in comparison to wildtype ubiquitin. In some embodiments, the binding affinity as determined by a Kd is determined by any method known in the art, in particular the methods described herein.

In another aspect, the conformationally stabilized ubiquitin proteins described herein inhibit (for example, completely inhibit) the activity of one or more ubiquitin processing enzymes or one or more deubiquitinases. In some embodiments, the conformationally stabilized ubiquitin proteins inhibit the activity of one or more ubiquitin processing enzymes (such as, but not limited to, an E1, an E2, or an E3 ubiquitin processing enzyme) or one or more deubiquitinases by any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, compared to the inhibition of these enzymes caused by wildtype ubiquitin. In some embodiments, the conformationally stabilized ubiquitin proteins are unable to be incorporated into polyubiquitin chains or to monoubiquitinate a target protein. In some embodiments, the conformationally stabilized ubiquitin proteins are able to be incorporated into polyubiquitin chains or to monoubiquitinate a target protein. In some embodiments, the conformationally stabilized ubiquitin proteins are able to be incorporated into polyubiquitin chains, but are incorporated by any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, less efficiently in comparison to the incorporation of wildtype ubiquitin into polyubiquitin chains.

In some aspects of any of the conformationally stabilized ubiquitin proteins disclosed herein, the one or more amino acid substitutions stabilize the β1/β2 loop of the protein such that the conformational dynamics of the β1/β2 loop is slowed relative to the motion of this region in the wildtype ubiquitin protein. In some embodiments, the β1/β2 loop region in the conformationally stabilized ubiquitin proteins exhibits any of about 10%, 20%, 30%, 40%, 50%, 60%, 70%, 80%, 90%, or 100%, inclusive, including any percentages in between these values, slower conformational dynamics in comparison to the conformational dynamics exhibited by this region in the wildtype ubiquitin protein. In some embodiments, the β1/β2 loop region in the conformationally stabilized ubiquitin proteins is confined to a region within about 0.5 to 3 Å, including any of about 0.7 to 2.7 Å, 1.0 to 2.4 Å, 1.3 to 2.1 Å, 1.6 to 1.8 Å root mean square deviation (RMSD) of Protein Data Bank code 3NHE chain B. In one embodiment, the β1/β2 loop region in the conformationally stabilized ubiquitin proteins is confined to a region within about 1.6 Å RMSD of Protein Data Bank code 3NHE chain B. In some embodiments, the microsecond $R_{ex}$ values in the region around the β1/β2 loop of any of the conformationally stabilized ubiquitin proteins disclosed herein are up to any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin. In a particular embodiment, the microsecond $R_{ex}$ values in the region around the β1/β2 loop of any of the conformationally stabilized ubiquitin proteins disclosed herein are up to about 40 fold greater in comparison to wildtype ubiquitin. In some embodiments, the degree of slower conformational dynamics of the β1/β2 loop region of the ubiquitin variants disclosed herein is determined by any method known in the art, in particular the methods described herein. In one embodiment, the method is NMR $R_2$ dispersion.

Provided herein are conformationally stabilized ubiquitin proteins. In some aspects, the conformationally stabilized ubiquitin proteins disclosed herein have one or more amino acid substitutions within the interior of the ubiquitin protein's tertiary structure that stabilizes the protein into a particular conformational state.

In some embodiments, the conformationally stabilized ubiquitin protein comprises one or more substitutions at amino acid residues selected from the group consisting of A7, A8, A13, A34, A36, A69, and A71, wherein the amino acid residue position is relative to SEQ ID NO:1. In some embodiments, the conformationally stabilized ubiquitin protein has a binding affinity as determined by a Kd to a binding partner of less than about any of about 1.0 mM, 500 μM, 100 μM, 50 μM, 25 μM, 10 μM, 5 μM, 1 μM, 900 nM, 800 nM, 700 nM, 600 nM, 500 nM, 400 nM, 300 nM, 200 nM, 150 nM, 100 nM, 90 nM, 80 nM, 70 nM, 60 nM, 50 nM, 45 nM, 40 nM, 35 nM, 30 nM, 25 nM, 20 nM, 15 nM, 10 nM, 5 nM, or 1 nM, inclusive, including any values in between these numbers. In some embodiments, the conformationally stabilized ubiquitin proteins inhibit the activity of one or more enzymatic ubiquitin binding partners by any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, compared to the inhibition of these enzymes caused by wildtype ubiquitin. In some embodiments the binding partner is an ubiquitin processing enzyme, such as, but not limited to, any E1, E2 or E3 ubiquitin processing enzymes or a deubiquitinase. In some embodiments, the binding partner is a member of the USP family of deubiquitinases (such as, but not limited to, USP7, USP5, and/or USP14). In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin. In another embodiment, the conformationally stabilized ubiquitin binds to USP14 but is unable to bind to USP7. In one embodiment, the binding partner is USP7. In one embodiment, the microsecond $R_{ex}$ values in the region around the β1/β2 loop of the conformationally stabilized ubiquitin proteins are up to any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin as measured by NMR $R_2$ dispersion. In a particular embodiment, the microsecond $R_{ex}$ values in the region around the β1/β2 loop of the conformationally stabilized ubiquitin proteins are up to about 40 fold greater in comparison to wildtype ubiquitin as measured by NMR $R_2$ dispersion. In some embodiments, the β1/β2 loop region in the conformationally stabilized ubiquitin proteins is confined to a region within about 0.5 to 3 Å, including any of about 0.7 to 2.7 Å, 1.0 to 2.4 Å, 1.3 to 2.1 Å, 1.6 to 1.8 Å RMSD of Protein Data Bank code 3NHE chain B. In one embodiment, the β1/β2 loop region in the conformationally stabilized ubiquitin proteins is confined to a region within about 1.6 Å RMSD of Protein Data Bank code 3NHE chain B. In some embodiments, the substitutions result in the formation of one or more disulfide bonds in the ubiquitin protein. In another embodiment, the substitutions do not result in the formation of one or more disulfide bonds in the ubiquitin protein.

In some aspects, the conformationally stabilized ubiquitin protein comprises one or more substitutions at amino acid residues selected from the group consisting of A7 (C), A8 (C), and A69 (C), wherein the amino acid residue position is relative to SEQ ID NO:1. In a particular embodiment, the protein comprises A7 (C) or A8 (C) and A69 (C). In some embodiments, the conformationally stabilized ubiquitin protein has a further substitution at A13. In one embodiment, the substitution at A13 is to a polar amino acid residue. In another embodiment, the protein comprises A13 (R, N, D, C, E, Q, H, K, S, T, or Y). In some embodiments, the protein comprises A13 (N, R, G, K, Y, A, S, or H). In yet another embodiment, the conformationally stabilized ubiquitin protein has a further substitution at A71. In one embodiment, the substitution at A71 is to a basic amino acid. In another embodiment, the protein comprises A71 (R, K, or H). In some embodiments, the protein comprises A13 (R or K). In a further embodiment, the conformationally stabilized ubiquitin protein has further substitutions at both A13 and at A71, wherein the substitution at A13 is to a polar amino acid residue and the substation at A71 is to a basic amino acid. In some embodiments, the protein comprises A13 (R, N, D, C, E, Q, H, K, S, T, or Y) and A71 (R, K, or H). In another embodiment, the protein comprises A13 (N, R, G, K, Y, A, S, or H) and A71 (R or K). In a further embodiment, the protein comprises A7 (C), A8 (C), or A69 (C) and can have additional substitutions at one or more of A36 (Y, F, L, or H), A34 (I, F, L, or V), A13 (N, R, G, K, Y, A, S, or H), or A71 (R or K). In some embodiments, the conformationally stabilized ubiquitin protein has a binding affinity as determined by a Kd to a binding partner of less than about any of about 1.0 mM, 500 μM, 100 μM, 50 μM, 25 μM, 10 µM, 5 µM, 1 µM, 900 nM, 800 nM, 700 nM, 600 nM, 500 nM, 400 nM, 300 nM, 200 nM, 150 nM, 100 nM, 90 nM, 80 nM, 70 nM, 60 nM, 50 nM, 45 nM, 40 nM, 35 nM, 30 nM, 25 nM, 20 nM, 15 nM, 10 nM, 5 nM, or 1 nM, inclusive, including any values in between these numbers. In some embodiments, the conformationally stabilized ubiquitin proteins inhibit the activity of one or more enzymatic ubiquitin binding partners by any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, compared to the inhibition of these enzymes caused by wildtype ubiquitin. In some embodiments the binding partner is an ubiquitin processing enzyme, such as, but not limited to, any E1, E2 or E3 ubiquitin processing enzymes or a deubiquitinase. In some embodiments, the binding partner is a member of the USP family of deubiquitinases (such as, but not limited to, USP7, USP5, and/or USP14). In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin. In another embodiment, the conformationally stabilized ubiquitin binds to USP14 but is unable to bind to USP7. In one embodiment, the binding partner is USP7. In one embodiment, the microsecond $R_{ex}$ values in the region around the β1/β2 loop of the conformationally stabilized ubiquitin proteins are up to any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin as measured by NMR $R_2$ dispersion. In a particular embodiment, the microsecond $R_{ex}$ values in the region around the β1/β2 loop of the conformationally stabilized ubiquitin proteins are up to about 40 fold greater in comparison to wildtype ubiquitin as measured by NMR $R_2$ dispersion. In some embodiments, the β1/β2 loop region in the conformationally stabilized ubiquitin proteins is confined to a region within about 0.5 to 3 Å, including any of about 0.7 to 2.7 Å, 1.0 to 2.4 Å, 1.3 to 2.1 Å, 1.6 to 1.8 Å RMSD of Protein Data Bank code 3NHE chain B. In one embodiment, the β1/β2 loop region in the conformationally stabilized ubiquitin proteins is confined to a region within about 1.6 Å RMSD of Protein Data Bank code 3NHE chain B. In some embodiments, the substitutions result in the formation of one or more disulfide bonds in the ubiquitin protein.

In some aspects, the conformationally stabilized ubiquitin protein comprises a substitution at amino acid residue A71, wherein the amino acid residue position is relative to SEQ ID NO:1. In some embodiments, the protein comprises A71(R, K, A, Q, G, W, H, I, or R). In some embodiments, the protein comprises A71(R). In some embodiments, the protein comprises A71 (K). In some embodiments, the protein comprises A71 (W). In some embodiments, the protein comprises A71 (G). In some embodiments, the protein with a substitution at A71 can have additional substitutions at one or more of A69 (C, G, A, W, K, Y, V, F, or I), A36 (Y, F, L, H, A, V, W, I, M or N), A34 (I, F, L, V, S, M, or T), A13 (N, R, G, K, Y, A, S, H, E, L, T, V, I, M, or P), A8 (T, C, D, R, G, C, T, A, Q, F, L, or Y) and/or A7 (C, N, F, S, R, G, V, or D). In some embodiments, the conformationally stabilized ubiquitin protein has a binding affinity as determined by a Kd to a binding partner of less than about any of about 1.0 mM, 500 µM, 100 µM, 50 µM, 25 µM, 10 µM, 5 µM, 1 µM, 900 nM, 800 nM, 700 nM, 600 nM, 500 nM, 400 nM, 300 nM, 200 nM, 150 nM, 100 nM, 90 nM, 80 nM, 70 nM, 60 nM, 50 nM, 45 nM, 40 nM, 35 nM, 30 nM, 25 nM, 20 nM, 15 nM, 10 nM, 5 nM, or 1 nM, inclusive, including any values in between these numbers. In some embodiments, the conformationally stabilized ubiquitin proteins inhibit the activity of one or more enzymatic ubiquitin binding partners by any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, compared to the inhibition of these enzymes caused by wildtype ubiquitin. In some embodiments the binding partner is an ubiquitin processing enzyme, such as, but not limited to, any E1, E2 or E3 ubiquitin processing enzymes or a deubiquitinase. In some embodiments, the binding partner is a member of the USP family of deubiquitinases (such as, but not limited to, USP7, USP5, and/or USP14). In one embodiment, the binding partner is USP7. In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin. In another embodiment, the conformationally stabilized ubiquitin binds to USP14 but is unable to bind to USP7. In some embodiments, the microsecond $R_{ex}$ values in the region around the β1/β2 loop of the conformationally stabilized ubiquitin proteins are up to any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin as measured by NMR $R_2$ dispersion. In a particular embodiment, the microsecond $R_{ex}$ values in the region around the β1/β2 loop of the conformationally stabilized ubiquitin proteins are up to about 40 fold greater in comparison to wildtype ubiquitin as measured by NMR $R_2$ dispersion. In some embodiments, the β1/β2 loop region in the conformationally stabilized ubiquitin proteins is confined to a region within about 0.5 to 3 Å, including any of about 0.7 to 2.7 Å, 1.0 to 2.4 Å, 1.3 to 2.1 Å, 1.6 to 1.8 Å RMSD of Protein Data Bank code 3NHE chain B. In one embodiment, the β1/β2 loop region in the conformationally stabilized ubiquitin proteins is confined to a region within about 1.6 Å RMSD of Protein Data Bank code 3NHE chain B.

In some aspects, the conformationally stabilized ubiquitin protein comprises a substitution at amino acid residue A34, wherein the amino acid residue position is relative to SEQ ID NO:1. In some embodiments, the substitution at A34 is to a hydrophobic amino acid. In some embodiments, the protein comprises A34 (A, V, I, L, M, F, Y, or W). In some embodiments, the protein comprises A34 (I, F, L, V, T, S, M or T). In some embodiments, the protein with a substitution at A34 can have additional substitutions at one or more of A71 (R, K, A, Q, W, G, H, I, R or G), A69 (C, G, A, W, K, Y, V, F, or I), A36 (Y, F, L, H, A, W, I, M, or N), A13 (N, R, G, K, Y, A, S, H, E, L, T, V, I, M, or P), A8 (T, C, D, R, G, C, T, A, Q, F, L, or Y) and/or A7 (C, N, F, S, R, G, V, or D). In some embodiments, the conformationally stabilized ubiquitin protein has a binding affinity as determined by a Kd to a binding partner of less than about any of about 1.0 mM, 500 µM, 100 µM, 50 µM, 25 µM, 10 µM, 5 µM, 1 µM, 900 nM, 800 nM, 700 nM, 600 nM, 500 nM, 400 nM, 300 nM, 200 nM, 150 nM, 100 nM, 90 nM, 80 nM, 70 nM, 60 nM, 50 nM, 45 nM, 40 nM, 35 nM, 30 nM, 25 nM, 20 nM, 15 nM, 10 nM, 5 nM, or 1 nM, inclusive, including any values in between these numbers. In some embodiments, the conformationally stabilized ubiquitin proteins inhibit the activity of one or more enzymatic ubiquitin binding partners by any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, compared to the inhibition of these enzymes caused by wildtype ubiquitin. In some embodiments the binding partner is an ubiquitin processing enzyme, such as, but not limited to, any E1, E2 or E3 ubiquitin processing enzymes or a deubiquitinase. In some embodiments, the binding partner is a member of the USP family of deubiquitinases (such as, but not limited to, USP7, USP5, and/or USP14). In one embodiment, the binding partner is USP7. In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin. In another embodiment, the conformationally stabilized ubiquitin binds to USP14 but is unable to bind to USP7. In some embodiments, the microsecond $R_{ex}$ values in the region around the β1/β2 loop of the conformationally stabilized ubiquitin proteins are up to any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin as measured by NMR $R_2$ dispersion. In a particular embodiment, the microsecond $R_{ex}$ values in the region around the β1/β2 loop of the conformationally stabilized ubiquitin proteins are up to about 40 fold greater in comparison to wildtype ubiquitin as measured by NMR $R_2$ dispersion. In some embodiments, the β1432 loop region in the conformationally stabilized ubiquitin proteins is confined to a region within about 0.5 to 3 Å, including any of about 0.7 to 2.7 Å, 1.0 to 2.4 Å, 1.3 to 2.1 Å, 1.6 to 1.8 Å RMSD of Protein Data Bank code 3NHE chain B. In one embodiment, the β1/β2 loop region in the conformationally stabilized ubiquitin proteins is confined to a region within about 1.6 Å RMSD of Protein Data Bank code 3NHE chain B.

In some aspects, the conformationally stabilized ubiquitin protein comprises a substitution at amino acid residue A7, wherein the amino acid residue position is relative to SEQ ID NO:1. In one embodiment, the protein comprises A7 (C, N, F, S, D, F, R, G, or V). In some embodiments, the protein comprises A7 (G). In some embodiments, the protein with a substitution at A7 can have additional substitutions at one or more of A71 (R, K, A, Q, W, G, H, I, R or G), A69 (C, G, A, W, K, Y, V, F, or I), A34 (I, F, L, V, S, M, or T), A13 (N, R, G, K, Y, A, S, H, E, L, T, V, I, M, or P), A8 (T, C, D, R, G, C, T, A, Q, F, L, or Y) and/or A36 (Y, F, L, H, I, A, or N). In some embodiments, the conformationally stabilized ubiquitin protein has a binding affinity as determined by a Kd to a binding partner of less than about any of about 1.0 mM, 500 µM, 100 µM, 50 µM, 25 µM, 10 µM, 5 µM, 1 µM, 900 nM, 800 nM, 700 nM, 600 nM, 500 nM, 400 nM, 300 nM, 200 nM, 150 nM, 100 nM, 90 nM, 80 nM, 70 nM, 60 nM, 50 nM, 45 nM, 40 nM, 35 nM, 30 nM, 25 nM, 20 nM, 15 nM, 10 nM, 5 nM, or 1 nM, inclusive, including any values in between these numbers. In some embodiments, the conformationally stabilized ubiquitin proteins inhibit the activity of one or more enzymatic ubiquitin binding partners by any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, compared to the inhibition of these enzymes caused by wildtype ubiquitin. In some embodiments the binding partner is an ubiquitin processing enzyme, such as, but not limited to, any E1, E2 or E3 ubiquitin processing enzymes or a deubiquitinase. In some embodiments, the binding partner is a member of the USP family of deubiquitinases (such as, but not limited to, USP7, USP5, and/or USP14). In one embodiment, the binding partner is USP7. In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin. In another embodiment, the conformationally stabilized ubiquitin binds to USP14 but is unable to bind to USP7. In some embodiments, the microsecond $R_{ex}$ values in the region around the β1/β2 loop of the conformationally stabilized ubiquitin proteins are up to any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin as measured by NMR $R_2$ dispersion. In a particular embodiment, the microsecond $R_{ex}$ values in the region around the β1/β2 loop of the conformationally stabilized ubiquitin proteins are up to about 40 fold greater in comparison to wildtype ubiquitin as measured by NMR $R_2$ dispersion. In some embodiments, the β1432 loop region in the conformationally stabilized ubiquitin proteins is confined to a region within about 0.5 to 3 Å, including any of about 0.7 to 2.7 Å, 1.0 to 2.4 Å, 1.3 to 2.1 Å, 1.6 to 1.8 Å RMSD of Protein Data Bank code 3NHE chain B. In one embodiment, the β1/β2 loop region in the conformationally stabilized ubiquitin proteins is confined to a region within about 1.6 Å RMSD of Protein Data Bank code 3NHE chain B.

In some aspects, the conformationally stabilized ubiquitin protein comprises a substitution at amino acid residue A36, wherein the amino acid residue position is relative to SEQ ID NO:1. In some embodiments, the substitution at A36 is to an aromatic amino acid. In one embodiment, the protein comprises A36 (W or Y). In another embodiment, the protein comprises A36 (L, F, W, M, Y, H, I, A, or N). In some embodiments, the protein with a substitution at A36 can have additional substitutions at one or more of A71 (R, K, A, Q, W, G, H, I, R or G), A69 (C, G, A, W, K, Y, V, F, or I), A34 (I, F, L, V, S, M, or T), A13 (N, R, G, K, Y, A, S, H, E, L, T, V, I, M, or P), A8 (T, C, D, R, G, C, T, A, Q, F, L, or Y) and/or A7 (C, N, F, S, R, G, V, or D). In some embodiments, the conformationally stabilized ubiquitin protein has a binding affinity as determined by a Kd to a binding partner of less than about any of about 1.0 mM, 500 µM, 100 µM, 50 µM, 25 µM, 10 µM, 5 µM, 1 µM, 900 nM, 800 nM, 700 nM, 600 nM, 500 nM, 400 nM, 300 nM, 200 nM, 150 nM, 100 nM, 90 nM, 80 nM, 70 nM, 60 nM, 50 nM, 45 nM, 40 nM, 35 nM, 30 nM, 25 nM, 20 nM, 15 nM, 10 nM, 5 nM, or 1 nM, inclusive, including any values in between these numbers. In some embodiments, the conformationally stabilized ubiquitin proteins inhibit the activity of one or more enzymatic ubiquitin binding partners by any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, compared to the inhibition of these enzymes caused by wildtype ubiquitin. In some embodiments the binding partner is an ubiquitin processing enzyme, such as, but not limited to, any E1, E2 or E3 ubiquitin processing enzymes or a deubiquitinase. In some embodiments, the binding partner is a member of the USP family of deubiquitinases (such as, but not limited to, USP7, USP5, and/or USP14). In one embodiment, the binding partner is USP7. In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin. In another embodiment, the conformationally stabilized ubiquitin binds to USP14 but is unable to bind to USP7. In another embodiment, the microsecond $R_{ex}$ values in the region around the β1/β2 loop of the conformationally stabilized ubiquitin proteins are up to any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin as measured by NMR $R_2$ dispersion. In a particular embodiment, the microsecond $R_{ex}$ values in the region around the β1/β2 loop of the conformationally stabilized ubiquitin proteins are up to about 40 fold greater in comparison to wildtype ubiquitin as measured by NMR $R_2$ dispersion. In some embodiments, the β1/β2 loop region in the conformationally stabilized ubiquitin proteins is confined to a region within about 0.5 to 3 Å, including any of about 0.7 to 2.7 Å, 1.0 to 2.4 Å, 1.3 to 2.1 Å, 1.6 to 1.8 Å RMSD of Protein Data Bank code 3NHE chain B. In one embodiment, the β1/β2 loop region in the conformationally stabilized ubiquitin proteins is confined to a region within about 1.6 Å RMSD of Protein Data Bank code 3NHE chain B.

In some aspects, the conformationally stabilized ubiquitin protein comprises a substitution at amino acid residues A7 or A8 and at A69 and A71, wherein the amino acid residue position is relative to SEQ ID NO:1. In some embodiments, the protein comprises A7 (C) or A8 (C) and A69 (C) and the substitution at A71 is to a basic amino acid. In one embodiment, the protein comprises A7(C), A71(R or K), and A8 (T, D, R, G, C, T, A, Q, F, L, or Y). In another embodiment, the protein comprises A8(C), A71(R or K), and A7 (N, F, S, R, G, V, or D). In some embodiments the conformationally stabilized ubiquitin protein further comprises one or more substitutions at any of A34 (I, F, L, V, S, M, or T), A13 (N, R, G, K, Y, A, S, H, E, L, T, V, I, M, or P), and/or A36 (Y, F, L, H, I, A, or N).

In some aspects, the conformationally stabilized ubiquitin protein comprises a substitution at amino acid residues A7 or A8 as well as at A69 and A34, wherein the amino acid residue position is relative to SEQ ID NO:1. In some embodiments, the protein comprises A7 (C) or A8(C), A69(C), and A34(I). In one embodiment, the protein comprises A7 (C) and A8 (T, D, R, G, C, T, A, Q, F, L, or Y). In another embodiment, the protein comprises A8 (C) and A7 (N, F, S, R, G, V, or D). In some embodiments the conformationally stabilized ubiquitin protein further comprises one or more substitutions at any of A13 (N, R, G, K, Y, A, S, H, E, L, T, V, I, M, or P), A71 (R, K, A, Q, W, G, H, I, R or G), and/or A36 (Y, F, L, H, I, A, or N). In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin.

In some aspects, the conformationally stabilized ubiquitin protein comprises a substitution at amino acid residues A7 or A8 as well as at A69, A34, and A36, wherein the amino acid residue position is relative to SEQ ID NO:1. In some embodiments, the protein comprises A7 (C) or A8(C), A69(C), A34 (I), and the substitution at A36 is to an aromatic amino acid. In one embodiment, the protein comprises A7(C), A36 (F or Y), and A8 (T, D, R, G, C, T, A, Q, F, L, or Y). In one embodiment, the protein comprises A8(C), A36 (F or Y), and A7(N, F, S, R, G, V, or D). In still another embodiment, the conformationally stabilized ubiquitin protein further comprises one or more substitutions at A13 (N, R, G, K, Y, A, S, H, E, L, T, V, I, M, or P) and/or A71 (R, K, A, Q, W, G, H, I, R or G). In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin.

In some aspects, the conformationally stabilized ubiquitin protein comprises a substitution at amino acid residues A7, A13, and A71, wherein the amino acid residue position is relative to SEQ ID NO:1. In some embodiments, the protein comprises A7 (F), A13(Y), and A71(R). In some embodiments, the conformationally stabilized ubiquitin protein further comprises one or more substitutions at A34 (I, F, L, V, S, M, or T), A69 (C, G, A, W, K, Y, V, F, or I), A8 (T, C, D, R, G, C, T, A, Q, F, L, or Y) and/or A36 (Y, F, L, H, I, A, or N). In some embodiments, the conformationally stabilized ubiquitin binds to USP7 but is unable to bind to USP14. In another embodiment, the conformationally stabilized ubiquitin binds to USP14 but is unable to bind to USP7.

In some aspects, the conformationally stabilized ubiquitin protein comprises a substitution at amino acid residues A7, A13, A34, A36, and A71, wherein the amino acid residue position is relative to SEQ ID NO:1. In some embodiments, the protein comprises A7(F), A13(Y), A71 (R), A34 (I or L), and A36 (I or L). In some embodiments, the protein comprises A34 (L) and A36 (I). In some embodiments, the protein comprises A34 (I) and A36 (L). In some embodiments, the conformationally stabilized ubiquitin protein further comprises one or more substitutions at A69 (C, G, A, W, K, Y, V, F, or I), and/or A8 (T, C, D, R, G, C, T, A, Q, F, L, or Y). In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin. In another embodiment, the conformationally stabilized ubiquitin binds to USP14 but is unable to bind to USP7.

In some aspects, the conformationally stabilized ubiquitin protein comprises a substitution at amino acid residues A7, A13, A34, A36, A69, and A71, wherein the amino acid residue position is relative to SEQ ID NO:1. In some embodiments, the protein comprises A7 (F), A13(Y), A71(R), A34 (I or L), A36 (I or L), and A69 (G or W). In one embodiment, the protein comprises A69 G), A34 (L), and A36 (I). In some embodiments, the protein comprises A69 (G), A34 (I), and A36 (L). In one embodiment, the protein comprises A69 (W), A34 (L), and A36 (I). In another embodiment, the protein comprises A69 (W), A34 (I), and A36 (L). In some embodiments, the conformationally stabilized ubiquitin protein further comprises a substitution at A8 (T, C, D, R, G, C, T, A, Q, F, L, or Y). In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin. In another embodiment, the conformationally stabilized ubiquitin binds to USP14 but is unable to bind to USP7.

In some aspects, the conformationally stabilized ubiquitin protein comprises substitutions at amino acid residues A7 and A71, wherein the amino acid residue position is relative to SEQ ID NO:1. In some embodiments, the protein comprises A7 (G) and A71 (W). In one embodiment, the protein has a further substitution at A8 to either to an F or to an L. In some embodiments the protein comprises A8 (F). In another embodiment, the protein comprises A8 (L). In some embodiments, the conformationally stabilized ubiquitin protein further comprises one or more substitutions at A34 (I, F, L, V, S, M, or T), A69 (C, G, A, W, K, Y, V, F, or I), A13 (N, R, G, K, Y, A, S, H, E, L, T, V, I, M, or P), and/or A36 (Y, F, L, H, I, A, or N). In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin. In another embodiment, the conformationally stabilized ubiquitin binds to USP14 but is unable to bind to USP7.

In some aspects, the conformationally stabilized ubiquitin protein comprises one or more substitutions selected from the group consisting of amino acid residues A7, A8, A13, A34, A36, A69, and A71, wherein the amino acid residue position is relative to SEQ ID NO:1, and wherein the substitutions result in the formation of at least one disulfide bond. In some aspects, the protein comprises A7 (C), A8 (L), A13 (N), A34 (I), A36 (Y), A69 (C), and A71 (R). In some aspects, the protein comprises A7 (C), A8 (T), A13 (R), A34 (I), A36 (F), A69 (C), and A71 (R). In some aspects, the protein comprises A7 (N), A8 (C), A13 (G), A34 (F), A36 (Y), A69 (C), and A71 (R). In some aspects, the protein comprises A7 (C), A8 (L), A13 (N), A34 (I), A36 (Y), A69 (C), and A71 (R). In some aspects, the protein comprises A7 (C), A8 (D), A13 (K), A34 (I), A36 (L), A69 (C), and A71 (R). In some aspects, the protein comprises A7 (C), A8 (D), A13 (K), A34 (I), A36 (F), A69 (C), and A71 (K). In some aspects, the protein comprises A7 (C), A8 (T), A13 (R), A34 (I), A36 (F), A69 (C), and A71 (R). In some aspects, the protein comprises A7 (F), A8 (R), A13 (Y), A34 (L), A36 (I), A69 (G), and A71 (R). In some aspects, the protein comprises A7 (C), A8 (T), A13 (R), A34 (L), A36 (F), A69 (C), and A71 (R). In some aspects, the protein comprises A7 (C), A8 (G), A13 (A), A34 (V), A36 (H), A69 (C), and A71 (R). In some aspects, the protein comprises A7 (C), A8 (T), A13 (R), A34 (L), A36 (F), A69 (C), and A71 (R). In some aspects, the protein comprises A7 (C), A8 (R), A13 (S), A34 (L), A36 (Y), A69 (C), and A71 (R). In some aspects, the protein comprises A7 (C), A8 (L), A13 (N), A34 (I), A36 (Y), A69 (C), and A71 (R). In some aspects, the protein comprises A7 (C), A8 (D), A13 (K), A34 (I), A36 (F), A69 (C), and A71 (K). In some aspects, the protein comprises A7 (C), A8 (R), A13 (S), A34 (L), A36 (Y), A69 (C), and A71 (R). In some aspects, the protein comprises A7 (C), A8 (D), A13 (K), A34 (I), A36 (L), A69 (C), and A71 (R). In some aspects, the protein comprises A7 (S), A8 (C), A13 (H), A34 (I), A36 (Y), A69 (C), and A71 (R). In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin. In some aspects, the protein comprises the substitutions of any of the clones shown in Table 1.

TABLE 1

U7Ub Disulfide clones
U7Ub Disulfide clones

| Clone ID | A7 | A8 | A13 | A34 | A36 | A69 | A71 |
|---|---|---|---|---|---|---|---|
| wt | T | L | I | E | I | L | L |
| U7Ub1 | C | L | N | I | Y | C | R |
| U7Ub3 | C | T | R | I | F | C | R |
| U7Ub4 | N | C | G | F | Y | C | R |
| U7Ub7 | C | L | N | I | Y | C | R |
| U7Ub9 | C | D | K | I | L | C | R |
| U7Ub15 | C | D | K | I | F | C | K |
| U7Ub23 | C | T | R | I | F | C | R |
| U7Ub25 | F | R | Y | L | I | G | R |
| U7Ub30 | C | T | R | L | F | C | R |
| U7Ub38 | C | G | A | V | H | C | R |
| U7Ub49 | C | T | R | L | F | C | R |
| U7Ub50 | C | R | S | L | Y | C | R |
| U7Ub51 | C | L | N | I | Y | C | R |
| U7Ub55 | C | D | K | I | F | C | K |
| U7Ub59 | C | R | S | L | Y | C | R |
| U7Ub74 | C | D | K | I | L | C | R |
| U7Ub88 | S | C | H | I | Y | C | R |

In some aspects, the conformationally stabilized ubiquitin protein comprises one or more substitutions selected from the group consisting of amino acid residues A7, A8, A13, A34, A36, A69, and A71, wherein the amino acid residue position is relative to SEQ ID NO:1, and wherein the substitutions do not result in the formation of at least one disulfide bond. In some aspects, the protein comprises A7 (D), A8 (Y), A13 (R), A34 (L), A36 (I), A69 (A), and A71 (A). In some aspects, the protein comprises A7 (F), A8 (A), A13 (Y), A34 (L), A36 (I), A69 (G), and A71 (R). In some aspects, the protein comprises A7 (F), A8 (G), A13 (Y), A34 (I), A36 (L), A69 (W), and A71 (R). In some aspects, the protein comprises A7 (F), A8 (Q), A13 (Y), A34 (L), A36 (I), A69 (G), and A71 (R). In some aspects, the protein comprises A7 (F), A8 (R), A13 (Y), A34 (L), A36 (I), A69 (G), and A71 (R). In some aspects, the protein comprises A7 (R), A8 (Q), A13 (E), A34 (L), A36 (Y), A69 (K), and A71 (Q). In some aspects, the protein comprises A7 (R), A8 (R), A13 (P), A34 (T), A36 (A), A69 (Y), and A71 (R). In some aspects, the protein comprises A7 (S), A8 (Y), A13 (Y), A34 (I), A36 (N), A69 (I), and A71 (G). In some embodiments, the conformationally stabilized ubiquitin binds to USP7 but is unable to bind to USP14. In some embodiments, the conformationally stabilized ubiquitin protein binds to USP7 with an affinity that is any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin. In some aspects, the protein comprises the substitutions of any of the clones shown in Table 2.

TABLE 2

U7Ub Non-Disulfide clones
U7Ub Non-disulfide clones

| Clone ID | A7 | A8 | A13 | A34 | A36 | A69 | A71 |
|---|---|---|---|---|---|---|---|
| wt | T | L | I | E | I | L | L |
| U7Ub551 | D | Y | R | L | I | A | A |
| U7Ub490 | F | A | Y | L | I | G | R |
| U7Ub511 | F | G | Y | I | L | W | R |
| U7Ub432 | F | Q | Y | L | I | G | R |
| U7Ub523(U7Ub25) | F | R | Y | L | I | G | R |
| U7Ub526 | R | Q | E | L | Y | K | Q |
| U7Ub402 | R | R | P | T | A | Y | R |
| U7Ub455 | S | Y | Y | I | N | I | G |

In some aspects, the conformationally stabilized ubiquitin protein comprises one or more substitutions selected from the group consisting of amino acid residues A7, A8, A13, A34, A36, A69, and A71, wherein the amino acid residue position is relative to SEQ ID NO:1. In some aspects, the protein comprises A7 (G), A8 (L), A13 (T), A34 (T), A36 (L), A69 (I), and A71 (W). In some aspects, the protein comprises A7 (G), A8 (F), A13 (L), A34 (T), A36 (L), A69 (S), and A71 (W). In some aspects, the protein comprises A7 (G), A8 (L), A13 (V), A34 (V), A36 (L), A69 (I), and A71 (W). In some aspects, the protein comprises A7 (G), A8 (L), A13 (L), A34 (S), A36 (L), A69 (V), and A71 (W). In some aspects, the protein comprises A7 (G), A8 (F), A13 (L), A34 (T), A36 (W), A69 (Y), and A71 (H). In some embodiments, the conformationally stabilized ubiquitin binds to USP14 but is unable to bind to USP7. In some aspects, the protein comprises the substitutions of any of the clones shown in Table 3.

TABLE 3

U14Ub clones
U14Ub clones

| Clone ID | A7 | A8 | A13 | A34 | A36 | A69 | A71 |
|---|---|---|---|---|---|---|---|
| wt | T | L | I | E | I | L | L |
| U14Ub1 | G | L | T | T | L | I | W |
| U14Ub14 | G | F | L | T | L | S | W |
| U14Ub2 | G | L | V | V | L | I | W |
| U14Ub22 | G | L | L | S | L | V | W |
| U14Ub24 | G | F | L | T | W | Y | H |

In some aspects, the conformationally stabilized proteins comprise the substitutions of any of clones U7Ub25, U7Ub7, or U14Ub2.

In a further aspect, any of the conformationally stabilized ubiquitin proteins described herein may further have one or more amino acid substitutions on the surface of the protein which increases its affinity to one or more binding partners. In some embodiments, the conformationally stabilized protein has one or more surface amino acid substitutions at A42, A46, A49, A62, A65, A68, or A70 where the amino acid residue positions correspond to A1-A76 of SEQ ID NO:1. In one embodiment, the conformationally stabilized ubiquitin protein has surface amino acid substitutions at one or more of A42 (K, T, or W), A46 (G or S), A49 (T, N, L, or R), A62 (E), A65 (T or A), A68 (R), or A70 (I). In another embodiment, the conformationally stabilized ubiquitin protein has surface amino acid substitutions at A42 (W), A49 (R), and A68 (R). In some aspects, the conformationally stabilized protein comprises the substitutions of clone U7Ub25.2540. In some embodiments, the conformationally stabilized ubiquitin protein has a binding affinity as determined by a Kd to a binding partner of less than about any of about 1.0 mM, 500 µM, 100 µM, 50 µM, 25 µM, 10 µM, 5 µM, 1 µM, 900 nM, 800 nM, 700 nM, 600 nM, 500 nM, 400 nM, 300 nM, 200 nM, 150 nM, 100 nM, 90 nM, 80 nM, 70 nM, 60 nM, 50 nM, 45 nM, 40 nM, 35 nM, 30 nM, 25 nM, 20 nM, 15 nM, 10 nM, 5 nM, or 1 nM, inclusive, including any values in between these numbers. In some embodiments, the conformationally stabilized ubiquitin proteins selectively inhibits the activity of one or more enzymatic ubiquitin binding partners by any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, compared to the inhibition of these enzymes caused by wildtype ubiquitin. In some embodiments the binding partner is an ubiquitin processing enzyme, such as, but not limited to, any E1, E2 or E3 ubiquitin processing enzymes or a deubiquitinase. In some embodiments, the binding partner is a member of the USP family of deubiquitinases (such as, but not limited to, USP7, USP5, and/or USP14). In one embodiment, the binding partner is USP7. In some embodiments, the microsecond $R_{ex}$ values in the region around the β1/β2 loop of the conformationally stabilized ubiquitin proteins are up to any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin as measured by NMR $R_2$ dispersion. In a particular embodiment, the microsecond $R_{ex}$ values in the region around the β1/β2 loop of the conformationally stabilized ubiquitin proteins are up to about 40 fold greater in comparison to wildtype ubiquitin as measured by NMR $R_2$ dispersion. In some embodiments, the β1/β2 loop region in the conformationally stabilized ubiquitin proteins is confined to a region within about 0.5 to 3 Å, including any of about 0.7 to 2.7 Å, 1.0 to 2.4 Å, 1.3 to 2.1 Å, 1.6 to 1.8 Å RMSD of Protein Data Bank code 3NHE chain B. In one embodiment, the β1/β2 loop region in the conformationally stabilized ubiquitin proteins is confined to a region within about 1.6 Å RMSD of Protein Data Bank code 3NHE chain B. In some aspects, the protein comprises the substitutions of any of the clones shown in Table 4.

TABLE 4

Surface residue substitutions

| Clone ID | A2 | A4 | A14 | A40 | A42 | A46 | A47 | A49 | A62 | A64 | A65 | A66 | A68 | A70 |
|---|---|---|---|---|---|---|---|---|---|---|---|---|---|---|
| Wt | Q | F | T | Q | R | A | G | Q | Q | E | S | T | H | V |
| Ub7.25/wt | Q | F | T | Q | R | A | G | T | Q | E | T | T | H | V |
| ub7v25R151 | Q | F | T | Q | R | G | G | N | Q | E | S | T | H | V |
| ub7v25R154 | Q | F | T | Q | R | A | G | Q | Q | E | S | T | H | V |

TABLE 4-continued

Surface residue substitutions

| | Clone ID | | | | | | | | | | | | | |
|---|---|---|---|---|---|---|---|---|---|---|---|---|---|---|
| | A2 | A4 | A14 | A40 | A42 | A46 | A47 | A49 | A62 | A64 | A65 | A66 | A68 | A70 |
| Ub7.25 | Q | F | T | Q | T | S | G | L | E | E | A | T | H | I |
| ub7v25R1558 | Q | F | T | Q | R | G | G | L | E | E | S | T | H | V |
| ub7v25R1554 | Q | F | T | Q | K | A | G | Q | Q | E | S | T | H | V |
| ub7v25R152 | Q | F | T | Q | W | A | G | R | Q | E | S | T | R | V |

In yet other aspects, any of the conformationally stabilized ubiquitin proteins described herein may further have one or more amino acid substitutions on the surface of the protein's C-terminal region which increases its affinity to one or more binding partners. In some embodiments, the conformationally stabilized protein has one or more surface amino acid substitutions at A40, A42, A46, A47, A49, A62, A65, A68, A70, A71, A72, A73, A74, A75, or A76 where the amino acid residue positions correspond to A1-A76 of SEQ ID NO:1. In one embodiment, the conformationally stabilized ubiquitin protein has surface amino acid substitutions at one or more of A42 (M), A46 (L or N), A49 (V, Y, L, or T), A62 (G or R), A65 (A), A68 (Q), A70 (R), A72 (W or H), A73 (A, R, or K), A74 (S, V, G, Y, or W), A75 (A, R, P, E, V, H, or Y), or A76 (R, S, V, A, or L). In another embodiment, the conformationally stabilized ubiquitin protein has surface amino acid substitutions at A42 (M), A49 (V), A70 (R), A72 (W), A73 (K), A74 (K), A75 (R), and A76 (V). In some aspects, the conformationally stabilized protein comprises the substitutions of clone Ub7.25.216. In some embodiments, the conformationally stabilized ubiquitin protein has a binding affinity as determined by a Kd to a binding partner of less than about any of about 1.0 mM, 500 µM, 100 µM, 50 µM, 25 µM, 10 µM, 5 µM, 1 µM, 900 nM, 800 nM, 700 nM, 600 nM, 500 nM, 400 nM, 300 nM, 200 nM, 150 nM, 100 nM, 90 nM, 80 nM, 70 nM, 60 nM, 50 nM, 45 nM, 40 nM, 35 nM, 30 nM, 25 nM, 20 nM, 15 nM, 10 nM, 5 nM, or 1 nM, inclusive, including any values in between these numbers. In some embodiments, the conformationally stabilized ubiquitin proteins selectively inhibits the activity of one or more enzymatic ubiquitin binding partners by any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, compared to the inhibition of these enzymes caused by wildtype ubiquitin. In some embodiments the binding partner is an ubiquitin processing enzyme, such as, but not limited to, any E1, E2 or E3 ubiquitin processing enzymes or a deubiquitinase. In some embodiments, the binding partner is a member of the USP family of deubiquitinases (such as, but not limited to, USP7, USP5, and/or USP14). In one embodiment, the binding partner is USP7. In some embodiments, the microsecond $R_{ex}$ values in the region around the β1/β2 loop of the conformationally stabilized ubiquitin proteins are up to any of about 10, 20, 30, 40, 50, 60, 70, 80, 90, 100, 200, 300, 400, 500, 600, 700, 800, 900, or 1000, inclusive, including any numbers in between these values, fold greater in comparison to wildtype ubiquitin as measured by NMR $R_2$ dispersion. In a particular embodiment, the microsecond $R_{ex}$ values in the region around the β1/β2 loop of the conformationally stabilized ubiquitin proteins are up to about 40 fold greater in comparison to wildtype ubiquitin as measured by NMR $R_2$ dispersion. In some embodiments, the β1/β2 loop region in the conformationally stabilized ubiquitin proteins is confined to a region within about 0.5 to 3 Å, including any of about 0.7 to 2.7 Å, 1.0 to 2.4 Å, 1.3 to 2.1 Å, 1.6 to 1.8 Å RMSD of Protein Data Bank code 3NHE chain B. In one embodiment, the β1/β2 loop region in the conformationally stabilized ubiquitin proteins is confined to a region within about 1.6 Å RMSD of Protein Data Bank code 3NHE chain B. In some aspects, the protein comprises the substitutions of any of the clones shown in Table 5.

TABLE 5

C-terminal region surface residue substitutions
(positions A72-A76 disclose SEQ ID NO 3-12, respectively, in order of apperance)

| | Clone ID | | | | | | | | | | | | |
|---|---|---|---|---|---|---|---|---|---|---|---|---|---|
| | A40 | A42 | A46 | A47 | A49 | A62 | A65 | A68 | A70 | A72 | A73 | A74 | A75 | A76 |
| Wt | Q | R | A | G | Q | Q | S | H | V | R | L | R | G | G |
| Ub7.25.206 | Q | R | L | G | Q | G | A | H | V | R | A | S | A | R |
| Ub7.25.207 | Q | R | A | G | Q | G | S | H | V | W | R | R | G | S |
| Ub7.25.216 | Q | M | A | G | V | Q | S | H | R | W | K | V | R | V |
| Ub7.25.268 | Q | R | A | G | L | Q | S | Q | V | W | K | R | P | A |
| Ub7.25.225 | Q | R | A | G | Y | Q | S | H | V | R | K | G | E | R |
| Ub7.25.226 | Q | R | N | G | Y | Q | S | H | V | R | R | Y | V | L |
| Ub7.25.227 | Q | R | A | G | Q | Q | S | H | V | W | R | S | H | G |
| Ub7.25.238 | Q | R | A | G | T | R | S | H | V | H | K | S | Y | A |
| Ub7.25.251 | Q | R | A | G | Q | Q | S | H | V | W | K | W | V | S |

In addition to the specific amino acid residue substitutions disclosed herein to conformationally stabilize an ubiquitin protein, the ubiquitin proteins may also comprise additional mutations that do not specifically impact conformational stability. These mutations result in an ubiquitin polypeptide as defined herein having at least about 80% amino acid sequence identity with any of the native sequence ubiquitin polypeptide sequences as disclosed herein. Such ubiquitin polypeptide variants include, for instance, ubiquitin polypeptides wherein one or more amino acid residues are added, or deleted, at the N- or C-terminus (such as the ubiquitin C-terminal di-glycine motif) of a native amino acid sequence. Ordinarily, a ubiquitin polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence ubiquitin polypeptide sequence as disclosed herein. Optionally, ubiquitin variant polypeptides will have no more than one conservative amino acid substitution as compared to a native ubiquitin polypeptide sequence, alternatively no more than 2, 3, 4, 5, 6, 7, 8, 9, or 10 conservative amino acid substitution as compared to the native ubiquitin polypeptide sequence.

In general, conformationally stabilized ubiquitin variants described herein include variants in which residues at a particular position in the sequence have been substituted by other amino acids, and further includes the possibility of inserting an additional residue or residues between two residues of the parent protein/peptide as well as the possibility of deleting one or more residues from the parent sequence or adding one or more residues to the parent sequence. Any amino acid substitution, insertion, or deletion can be encompassed by the invention. In some embodiments, the substitution is a conservative substitution as described herein, preferably when part or all of the conformation of the protein is preserved and stabilized.

In some aspects, the conformationally stabilized ubiquitin proteins described herein comprise a deletion of one or more amino acid residues. In some embodiments, the protein comprises deletions of A75 and A76, wherein the amino acid residue position is relative to SEQ ID NO:1. In some embodiments, the conformationally stabilized ubiquitin protein binds to USP7 but is unable to bind to USP5. In another embodiment, the conformationally stabilized ubiquitin protein inhibits the enzymatic activity of USP7 by any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, but does not inhibit the enzymatic activity of USP5. In some aspects, the conformationally stabilized ubiquitin protein comprises the substitutions and deletions of clone U7Ub25ΔΔGG.

Conservative substitutions of peptides/polypeptides are shown in Table 6 under the heading of "preferred substitutions." If such substitutions result in a change in biological activity, then more substantial changes, denominated "exemplary substitutions" in Table 6, or as further described below in reference to amino acid classes, may be introduced and the products screened.

TABLE 6

Potential amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |

TABLE 6-continued

Potential amino acid substitutions

| Original Residue | Exemplary Substitutions | Preferred Substitutions |
|---|---|---|
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the peptide/polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Non-conservative substitutions will entail exchanging a member of one of these classes for another class Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe;
(7) large hydrophobic: Norleucine, Met, Val, Leu, Ile;

In further embodiments, peptides or polypeptides of the invention may comprise one or more non-naturally occurring or modified amino acids. A "non-naturally occurring amino acid residue" refers to a residue, other than those naturally occurring amino acid residues listed above, which is able to covalently bind adjacent amino acid residues(s) in a polypeptide chain. Non-natural amino acids include, but are not limited to homo-lysine, homo-arginine, homo-serine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, citrulline, pentylglycine, pipecolic acid and thioproline. Modified amino acids include natural and non-natural amino acids which are chemically blocked, reversibly or irreversibly, or modified on their N-terminal amino group or their side chain groups, as for example, N-methylated D and L amino acids, side chain functional groups that are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide and a modified amino acid of alanine. Additional non-natural and modified amino acids, and methods of incorporating them into proteins and peptides, are known in the art (see, e.g., Sandberg et al., (1998) *J. Med. Chem.* 41: 2481-91; Xie and Schultz (2005) *Curr. Opin. Chem. Biol.* 9: 548-554; Hodgson and Sanderson (2004) *Chem. Soc. Rev.* 33: 422-430.

In some embodiments of any of the conformationally stabilized ubiquitin proteins described herein, the protein may be isolated. In some embodiments of any of the conformationally stabilized ubiquitin proteins described herein, the protein is a synthetic protein or a polypeptide chain created through chemical synthesis.

In some embodiments, the conformationally stabilized ubiquitin proteins described herein can be isolated from cells by an appropriate purification scheme using standard protein purification techniques. In another embodiment, the conformationally stabilized ubiquitin proteins described herein are produced by recombinant DNA techniques. Alternative to recombinant expression, conformationally stabilized ubiquitin proteins described herein can be synthesized chemically using standard peptide synthesis techniques.

In some embodiments, the conformationally stabilized ubiquitin proteins described herein are substantially isolated (such as isolated) polypeptides. Contaminant components include materials that would typically interfere with diagnostic or therapeutic uses for the polypeptide, and may include enzymes, hormones, and other proteinaceous or non-proteinaceous materials. Preparations having preferably less than about 30% by dry weight of non-desired contaminating material (contaminants), preferably less than about 20%, about 10%, and preferably less than about 5% contaminants are considered to be substantially isolated. An isolated, recombinantly-produced peptide/polypeptide or biologically active portion thereof is preferably substantially free of culture medium, i.e., culture medium represents preferably less than about 20%, preferably less than about 10%, and preferably less than about 5% of the volume of a peptide/polypeptide preparation. Examples of contaminants include cell debris, culture media, and substances used and produced during in vitro synthesis of the peptide/polypeptide B. Conformationally Stabilized Ubiquitin Fusions Further provided herein are conformationally stabilized ubiquitin fusions comprising any of the conformationally stabilized ubiquitin proteins described herein conjugated to a carrier. In some embodiments of any of the conformationally stabilized ubiquitin protein fusions, the carrier to which the conformationally stabilized ubiquitin protein is conjugated is a biodegradable polymer. Biodegradable or biocompatible polymers can be used, such as ethylene vinyl acetate, polyanhydrides, polyglycolic acid, polyorthoesters, polylactic acid, PEG, polylactide, polyglycolide, polycaprolactone, carbohydrates, polypeptides, collagen, starches, cellulose, chitins, lignins, and co-polymers thereof. Such materials can be obtained commercially from ALZA Corporation (Mountain View, Calif.) and NOVA Pharmaceuticals, Inc. (Lake Elsinore, Calif.), or prepared by one of skill in the art. Liposomal suspensions can also be used as pharmaceutically acceptable carriers. These can be prepared according to methods known to those skilled in the art, such as in (Eppstein et al., U.S. Pat. No. 4,522,811, 1985). In some embodiments, the carrier is a polypeptide. In some embodiment, the polypeptide is albumin. In some embodiments, the polypeptide is an Fc. In some embodiments, the carrier is PEG.

In some embodiments of any of the conformationally stabilized ubiquitin protein fusions, the carrier is conjugated to the C-terminus of the conformationally stabilized ubiquitin protein. In some embodiments of any of the conformationally stabilized ubiquitin protein fusions, the carrier is not conjugated to the N-terminus of the conformationally stabilized ubiquitin protein.

In some embodiments of any of the conformationally stabilized ubiquitin protein fusions, the carrier is covalently conjugated to the conformationally stabilized ubiquitin protein. In some embodiments of any of the conformationally stabilized ubiquitin protein fusions, the carrier is directly conjugated to the conformationally stabilized ubiquitin protein. In some embodiments of any of the conformationally stabilized ubiquitin protein fusions, the carrier is covalently conjugated to the conformationally stabilized ubiquitin protein via a linker sequence. In some embodiments, the carrier is conjugated as a fusion protein with the conformationally stabilized ubiquitin protein.

In some embodiments of any of the conformationally stabilized ubiquitin protein fusions, the conjugation of the conformationally stabilized ubiquitin protein to the carrier increases the half-life and/or bioavailability of the conformationally stabilized ubiquitin protein compared to the conformationally stabilized ubiquitin protein unconjugated to the carrier.

C. Protein Complexes

Also provided herein are protein complexes comprising any of the conformationally stabilized ubiquitin proteins disclosed herein and a binding partner. In some embodiments the binding partner is an ubiquitin processing enzyme, such as, but not limited to, any E1, E2 or E3 ubiquitin processing enzymes or a deubiquitinase. In some embodiments, the binding partner is a member of the USP family of deubiquitinases (such as, but not limited to, USP7, USP5, and/or USP14). In some embodiments, the proteins within the protein complex bind to each other with an affinity as determined by a Kd of less than about any of about 1.0 mM, 500 µM, 100 µM, 50 µM, 25 µM, 10 µM, 5 µM, 1 µM, 900 nM, 800 nM, 700 nM, 600 nM, 500 nM, 400 nM, 300 nM, 200 nM, 150 nM, 100 nM, 90 nM, 80 nM, 70 nM, 60 nM, 50 nM, 45 nM, 40 nM, 35 nM, 30 nM, 25 nM, 20 nM, 15 nM, 10 nM, 5 nM, or 1 nM, inclusive, including any values in between these numbers. In some embodiments, when the binding partner in an enzyme, the binding of the conformationally stabilized ubiquitin protein and the enzyme to form a protein complex selectively inhibits (such as completely inhibits) the enzymatic activity of the enzyme. In another embodiment, the conformationally stabilized ubiquitin decreases the enzymatic activity of the enzyme by any of about 10%, 20%, 30%, 40%, 50%, 60%, 70%, 80%, 90%, or 100%, inclusive, including any percentages in between these values, when the enzyme and the conformationally stabilized ubiquitin form a protein complex.

Also provided herein are ubiquitinated protein complexes comprising a protein linked directly (e.g., directly (for example, by a covalent lingage) or indirectly) to any of the conformationally stabilized ubiquitin proteins disclosed herein. In some embodiments, the protein is monoubiquitinated. In another embodiment, the protein is multiubiquitinated on multiple (such as 2, 3, 4, 5, 6, 7, 8, 9, or 10 or more) lysine residues. In another embodiment, the conformationally stabilized ubiquitin proteins covalently attached to the protein form polyubiquitin chains on any (such as any of 1, 2, 3, 4, 5, 6, or 7) of the ubiquitin protein's lysine residues. In some embodiments, the polyubiquitin chain can include one or more wildtype ubiquitin proteins, in addition to the conformationally stabilized ubiquitin proteins disclosed herein.

In some aspects, any of the conformationally stabilized ubiquitin proteins or protein complexes can be immobilized on a solid support using any method known in the art. In another aspect, a cell or a population of cells that express any of the conformationally stabilized ubiquitin proteins disclosed herein can also be immobilized on a solid support. The present application thus also provides 1) a solid support coupled with any of the conformationally stabilized ubiquitin proteins disclosed herein and 2) a solid support coupled to a cell or population of cells expressing any of the conformationally stabilized ubiquitin proteins disclosed herein.

Also provided herein are solid supports having a protein complex comprising a conformationally stabilized ubiquitin protein (such as any described herein) in complex with a USP family deubiquitinase (such as, but not limited to, USP7). Examples of suitable solid supports include, but are not limited to, glass, plastic, metal, latex, rubber, ceramic, polymers such as polypropylene, polyvinylidene difluoride, polyethylene, polystyrene, and polyacrylamide, dextran, cellulose, nitrocellulose, pvdf, nylon, amylose, and the like. A solid support can be flat, concave, or convex, spherical, cylindrical, and the like, and can be particles (such as a nanoparticle), beads (such as a magnetic bead), membranes, strands, precipitates, gels, sheets, containers, wells, capillaries, films, plates, slides, and the like. The solid support can be magnetic, or a column. In some embodiments, the solid support is suitable for conducting surface plasmon resonance. In one particular embodiment, a protein microarray may be prepared in which any of the conformationally stabilized ubiquitin proteins or protein complexes described herein can be immobilized onto a surface of a solid support. In one embodiment, the conformationally stabilized ubiquitin proteins or protein complexes are modified to include one or more functional groups which bind a single protein, a functional or structural class of proteins, or proteins in general, for protein immobilization to a solid support. For example, fusion protein systems such as a thioredoxin patch, intein based approaches or other methods can be employed to immobilize a conformationally stabilized ubiquitin protein or protein complex. The conformationally stabilized ubiquitin proteins or protein complexes may be modified with succinimidyl ester/aldehyde (for general immobilization of proteins), glutathione (for immobilizing GST fusion proteins), NTA or metal (for immobilizing His-tagged proteins), or specific ligands (such as a deubiquitinase from the USP family of deubiquitinases) for immobilizing specific classes of proteins. Similarly, to study protein-protein interactions including isolating protein complexes, a conformationally stabilized ubiquitin protein, protein complexe or modified protein, such as any of those disclosed herein, can be immobilized on magnetic or non-magnetic particles, e.g., MagneSil particles.

D. Nucleic Acids

Provided herein are isolated nucleic acids that encode any of the conformationally stabilized ubiquitin proteins disclosed herein. The disclosure provides an isolated nucleic acid molecule, wherein the nucleic acid molecule encodes a protein comprising an amino acid sequence with at least 85%, 86%, 87%, 88%, 89%, 90%, 91%, 92%, 93%, 94%, 95%, 96%, 97%, 98%, 99%, or 100% sequence identity to the amino acid sequence of SEQ ID NO:1.

E. Vectors

Polynucleotide sequences encoding any of the conformationally stabilized ubiquitin proteins described herein can be obtained using standard synthetic and/or recombinant techniques. Desired polynucleotide sequences may be isolated and sequenced from appropriate source cells. Source cells for antibodies, peptides, and/or polypeptides would include antibody, peptide, and/or polypeptide producing cells such as hybridoma cells. Alternatively, polynucleotides can be synthesized using nucleotide synthesizer or PCR techniques. Once obtained, sequences encoding the antibody, peptide, and/or polypeptide are inserted into a recombinant vector capable of replicating and expressing heterologous polynucleotides in a host cell. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication (in particular when the vector is inserted into a prokaryotic cell), a selection marker gene, a promoter, a ribosome binding site (RBS), a signal sequence, the heterologous nucleic acid insert and a transcription termination sequence. In some embodiments, the vector is an expression vector.

In general, plasmid vectors containing replicon and control sequences which are derived from a species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as λBEM.TM.-11 may be utilized in making a recombinant vector which can be used to transform susceptible host cells such as E. coli LE392.

Either constitutive or inducible promoters can be used in the present invention, in accordance with the needs of a particular situation, which can be ascertained by one skilled in the art. A large number of promoters recognized by a variety of potential host cells are well known. The selected promoter can be operably linked to cistron DNA encoding a polypeptide described herein by removing the promoter from the source DNA via restriction enzyme digestion and inserting the isolated promoter sequence into the vector of choice. Both the native promoter sequence and many heterologous promoters may be used to direct amplification and/or expression of the target genes. However, heterologous promoters are preferred, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In some embodiments, each cistron within a recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP.

F. Host Cells

Prokaryotic host cells suitable for expressing polypeptides include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. Preferably, gram-negative cells are used. Preferably the host cell should secrete minimal amounts of proteolytic enzymes, and additional protease inhibitors may desirably be incorporated in the cell culture.

In one embodiment, the host cell is a yeast cell selected from the group consisting of a *Saccharomyces*, a *Pichia*, and a *Candida*. In another embodiment, the cell is a *Caenorhabdus elegans* nematode cell. In another embodiment, the cell is an insect cell, such as a *Drosophila* cell. In still another embodiment, the cell is a zebrafish cell.

Examples of mammalian cells capable of expressing any of the conformationally stabilized ubiquitin proteins disclosed herein can be selected from the group consisting of a hamster cell, a mouse cell, a rat cell, a rabbit cell, a cat cell, a dog cell, a bovine cell, a goat cell, a porcine cell, an equine cell, a sheep cell, a monkey cell, a chimpanzee cell, and a human cell. In another embodiment, the animal cell is a neural cell (such as, but not limited to, a peripheral nervous system cell or a central nervous system cell), a muscle cell (such as a cardiac, skeletal, or smooth muscle cell), a gamete (such as a sperm cell or an oocyte), a cancer cell, an immune cell (such as, but not limited to, a macrophage, a T-cell, or a B-cell), a stem cell (such as, but not limited to, an embryonic stem cell or an adult stem cell), or an endocrine cell (such as, but not limited to, a thyroid cell, a hypothalamic cell, a pituitary cell, an adrenal cell, a testicular cell, an ovarian cell, a pancreatic cell (such as a $\beta$ cell), a stomach cell, or an intestinal cell). In some embodiments, the cell is a human cell in cell culture. In some embodiments, the cell is a non-human cell in cell culture. In some embodiments, the cell is a cancer cell.

G. Production of Conformationally Stabilized Ubiquitin Proteins

Host cells are transformed or transfected with the above-described expression vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector, protein expression is induced under conditions suitable for the activation of the promoter. For example, if a PhoA promoter is used for controlling transcription, the transformed host cells may be cultured in a phosphate-limiting medium for induction. A variety of other inducers may be used, according to the vector construct employed, as is known in the art.

Polypeptides described herein expressed in a microorganism may be secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therefrom. Cells may be removed from the culture and the culture supernatant being filtered and concentrated for further purification of the proteins produced. The expressed polypeptides can be further isolated and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable antigen immobilized on a matrix and Western blot assay.

Besides prokaryotic host cells, eukaryotic host cell systems are also well established in the art. Suitable hosts include mammalian cell lines such as CHO, and insect cells such as those described below.

H. Polypeptide/Peptide Purification

Polypeptides/peptides that are produced may be purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

IV. Methods of the Invention

Provided herein are methods for selectively inhibiting a deubiquitinase of the USP family. Also provided herein are methods for identifying an agent that 1) binds to a conformational form of a ubiquitin protein (for example, a conformational form of ubiquitin that favorably binds to a deubiquitinase of the USP family of deubiquitinases); 2) binds to a USP-deubiquitinase/ubiquitin protein complex; 3) binds to a deubiquitinase of the USP family; and/or 4) is capable of disrupting a USP-deubiquitinase/ubiquitin protein complex. Further provided herein is a method for screening for a conformationally stabilized form of a protein, wherein the conformationally stabilized form of the protein has an increased binding affinity to a binding partner as compared to the wild-type form of the protein. Also provided herein are agents identified by the methods of any of the claims disclosed herein.

A. Methods for Selectively Inhibiting a Deubiquitinase of the USP Family

Provided herein are methods for selectively inhibiting the enzymatic activity of a deubiquitinase of the USP family of deubiquitinases. In some aspects, the method comprises contacting the deubiquitinase with any of the conformationally stabilized ubiquitin proteins disclosed herein. In some embodiments, the USP deubiquitinase is any of USP1, USP2, USP3, USP4, USP5, USP6, USP7, USP5, USP9X, USP9Y, USP10, USP11, USP12, USP13, USP14, USP15, USP16, USP17, USP17L2, USP17L3, USP17L4, USP17L5, USP17L7, USP17L8, USP18, USP19, USP20, USP21, USP22, USP23, USP24, USP25, USP26, USP27X, USP28, USP29, USP30, USP31, USP32, USP33, USP34, USP35, USP36, USP37, USP38, USP39, USP40, USP41, USP42, USP43, USP44, USP45, or USP46. In another embodiment, the USP deubiquitinase is USP7, USP5, or USP14. In one embodiment, the USP deubiquitinase is USP7. In some embodiments, the USP deubiquitinase is contacted with the conformationally stabilized ubiquitin protein, wherein the conformationally stabilized ubiquitin protein comprises any of the amino acid substitutions described herein. In one embodiment, the USP deubiquitinase is contacted with the conformationally stabilized ubiquitin protein in vitro. In another embodiment, the USP deubiquitinase is contacted with the conformationally stabilized ubiquitin protein in vivo (such as, for example, by co-expression of the USP deubiquitinase with any of the conformationally stabilized ubiquitin proteins disclosed herein by any means known in the art or by administration of the conformationally stabilized ubiquitin protein in a lipid-soluble carrier). In another embodiment, the inhibition is in vivo. In some embodiments, the conformationally stabilized ubiquitin protein is a USP deubiquitinase antagonist. In some embodiments, contacting the USP deubiquitinase with any of the conformationally stabilized ubiquitin proteins disclosed herein selectively inhibits (such as completely inhibits) the enzymatic activity of the USP deubiquitinase. In some embodiments, contacting the USP deubiquitinase with any of the conformationally stabilized ubiquitin proteins disclosed herein selectively inhibits the deubiquitinase enzymatic activity of the USP deubiquitinase by any of about 5%, 10%, 15%, 20%, 25%, 30%, 35%, 40%, 45%, 50%, 55%, 60%, 65%, 70%, 75%, 80%, 85%, 90%, 95%, or 100%, inclusive, including any percentage in between these values, compared to the inhibition of these enzymes caused by wildtype ubiquitin.

B. Methods for Identifying Agents that Bind to a Conformational Form of Ubiquitin The present invention also provides methods for identifying (or screening for) one or more agents that bind (such as preferentially bind) to a particular conformational form of ubiquitin (for example, a conformational form of ubiquitin wherein one or more amino acid substitutions stabilize(s) the β1/β2 loop region of the ubiquitin protein such that the β1/(β2 loop region is confined to a region within about 1.6 Å RMSD of Protein Data Bank Code 3NHE chain B). Such assays can include assays amenable to high throughput screening of libraries (such as peptide or chemical libraries).

In some embodiments, there is provided a method of identifying an agent that binds (such as preferentially binds) to a conformational form of the ubiquitin protein that is favorable for binding to a binding partner, comprising contacting the agent with a conformationally stabilized ubiquitin protein (such as any of the conformationally stabilized ubiquitin proteins disclosed herein) and determining whether the agent is capable of binding to said conformationally stabilized form of ubiquitin.

Conformationally stabilized ubiquitin proteins useful for the binding assay can be stabilized ubiquitin proteins or a fragment thereof, so long as the fragment is capable of maintaining the same conformational stability with respect to the β1/β2 loop region as the full length stabilized protein. Alternatively, the conformationally stabilized ubiquitin protein or fragment thereof can be contained within a polypeptide, that is, the polypeptide used for the binding assay can comprise additional amino acid residues not present in the monomeric conformationally stabilized ubiquitin protein.

The binding assays described herein generally require contacting the two components to be tested for binding (for example a conformationally stabilized ubiquitin protein, such as a stabilized ubiquitin protein favorable for binding to a deubiquitinase of the USP family of deubiquitinases and an agent) under conditions and for a time sufficient to allow these components to interact. The complex formed can be isolated or detected in the reaction mixture. In one exemplary embodiment, one component (e.g., a conformationally stabilized ubiquitin protein, such as any disclosed herein) is immobilized on a solid phase, e.g., on a microtiter place, by covalent or non-covalent attachments. Non-covalent attachment generally is accomplished by coating the solid surface with a solution of the agent and drying. Alternatively, an immobilized affinity molecule, such as an antibody, e.g., a monoclonal antibody, specific for the agent to be immobilized can be used to anchor it to a solid surface. The assay is performed by adding the non-immobilized component (e.g., an agent), which may be labeled by a detectable label, to the immobilized component, e.g., the coated surface containing the anchored component. When the reaction is complete, the non-reactive components are removed, e.g., by washing, and complexes anchored on the solid surface is detected. Where the originally non-mobilized component carries a detectable label, the detection of label immobilized on the surface indicates that binding occurred. Where the originally non-immobilized component does not carry a label, binding can be detected, for example, by using a labeled antibody specifically binding the immobilized complex.

In some embodiments, an agent that inhibits the binding of a conformationally stabilized ubiquitin protein and binding partner (such as a member of the USP family of deubiquitinases) is tested as follows: a reaction mixture is prepared containing the conformationally stabilized ubiquitin protein or fragment thereof and binding partner or fragment thereof under conditions and for a time allowing for the interaction and binding of the two components. To test the ability of a candidate agent to inhibit binding, the reaction is run in the absence and presence of the candidate agent. In addition, a placebo may be added to a separate reaction mixture to serve as a positive control. The binding (complex formation) between the candidate agent, conformationally stabilized ubiquitin protein and binding partner (or equivalent thereof) is monitored as described above. The formation of a complex in the control reaction but not in the reaction mixture containing the candidate compound indicates that the candidate compound inhibits the binding of the conformationally stabilized ubiquitin protein to the binding partner. Furthermore, different amounts of the candidate agent can be tested to determine whether the inhibition of binding is competitive.

In an alternative method, a reaction can be conducted in a liquid phase, the reaction products separated from unreactive components, and complexes detected; e.g., using an immobilized antibody specific for the conformationally stabilized ubiquitin protein, the binding partner or fragment thereof (such as a member of the USP family of deubiquitinases or fragment thereof), or the candidate agent to anchor any complexes formed in solution, and a labeled antibody specific for the other component of the possible complex can be used to detect the anchored complexes. Alternatively, cell-based assays can be used for binding assays. Specifically, cell lines (e.g., COS cells, CHO 3J cells, fibroblasts, etc.) that have been engineered to express a conformationally stabilized ubiquitin protein (e.g., by transfection or transduction with a ubiquitin variant DNA, etc.) can be used.

The agent identified by methods described above can further be assayed for its binding specificity as further described below. Methods of identifying an agent that binds to a specific binding site can be carried out independently of the screening methods described above, or in conjunction with the inhibition screening assays. In other words, a method of identifying an agent that inhibits (such as partial or complete inhibition) the enzymatic activity of a binding partner (such as a member of the USP family of deubiquitinases) as described herein can be carried out by first screening for agents that inhibit (for example competitively inhibit) the binding of a conformationally stabilized ubiquitin protein to a binding partner (also referred to as "inhibition-based screening") followed by identifying an agent from said screening results that bind to a specific binding site on the conformationally stabilized ubiquitin (also referred to as "binding-based screening"). Alternatively, one can screen for agents that bind to a specific binding site on the conformationally stabilized ubiquitin without first conducting an inhibition-based screening (or is followed by an inhibition-based assay).

In some embodiments, the inhibition-based screening and/or binding-based screening can be carried out in conjunction with a screening/identification method based on a functional readout of the agent. Functional readout of an agent that inhibits the activity of an enzyme known to interact with ubiquitin can be devised based on knowledge of biological activities associated with the ubiquitin/proteasome processing machinery, including, but not limited to, ubiquitin cleavage from target proteins, removal or incorporation of ubiquitin monomers into polyubiquitin chains, target protein degradation via the proteasome complex, or the functioning of the ubiquitin processing enzymes. The functional screening/identification method can be carried out either before or after the inhibition-based screening and/or the binding-based screening.

Thus, in some aspects, provided herein are methods for identifying an agent that binds (such as preferentially binds) to a conformationally stabilized form of ubiquitin, such as any of the conformationally stabilized forms of ubiquitin disclosed herein. The agent can be a small molecule chemical compound, an inhibitory nucleic acid, a protein (such as a non-antibody inhibitory peptide or an antibody), or any combination thereof. In some embodiments, the methods comprise contacting the agent with any of the conformationally stabilized ubiquitin proteins disclosed herein and determining whether the agent is capable of binding to the conformationally stabilized ubiquitin protein.

In some embodiments, the conformationally stabilized form of ubiquitin is a conformational form that is favorable for binding to one or more specific binding partner(s). In some embodiments, the binding of the agent can inhibit the binding of (for example, can disrupt the interaction between) one or more of the binding partners that bind (such as preferentially bind) to the conformational form of ubiquitin. In one embodiment, the binding partner is a ubiquitin processing enzyme such as, but not limited to, any E1, E2 or E3 ubiquitin processing enzyme or a deubiquitinase. In some embodiments, the binding partner is a member of the USP family of deubiquitinases (such as, but not limited to, USP7, USP5, and/or USP14). In some embodiments, the agent competitively inhibits the binding of a binding partner to a specific conformational form of ubiquitin (for example, a conformational form of ubiquitin wherein one or more amino acid substitutions stabilize(s) the β1/β2 loop region of the ubiquitin protein such that the β1/β2 loop region is confined to a region within about 1.6 Å RMSD of Protein Data Bank Code 3NHE chain B) but does not affect the binding of the binding partner to other conformational forms of ubiquitin. In additional embodiments, the agent competes with the binding of a binding partner to a specific conformational form of ubiquitin at an $IC_{50}$ of less than about 40 nM (for example, less than about 35 nM, 30 nM, 25 nM, 20 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM) under competitive ELISA assay. In some embodiments, the agent bound to ubiquitin suppresses the enzymatic activities of one or more binding partners, such as the enzymatic activity of a deubiquitinase of the USP family of deubiquitinases.

Also provided herein are agents identified by the methods of any of the claims disclosed herein.

C. Methods for Identifying an Agent that Disrupts or Binds to a Ubiquitin/USP-Deubiquitinase Protein Complex The present invention also provides methods for identifying (or screening for) one or more agents that binds to a protein complex comprising a deubiquitinase of the USP family (such as, but not limited to, USP7) and ubiquitin. In one aspect, there is provided a method for identifying (or screening for) one or more agents that can disrupt an ubiquitin/USP-deubiquitinase protein complex. Such assays can include assays amenable to high throughput screening of libraries (such as peptide or chemical libraries).

In some aspects, there is provided a method of identifying an agent that binds (such as preferentially binds) to a deubiquitinase of the USP family, comprising contacting the agent with a protein complex comprising a deubiquitinase of the USP family and any of the conformationally stabilized ubiquitin proteins disclosed herein and determining whether the agent is capable of binding to said deubiquitinase. In some aspects, there is provided a method of identifying an agent that binds (such as preferentially binds) to ubiquitin comprising contacting the agent with a protein complex comprising a deubiquitinase of the USP family and any of the conformationally stabilized ubiquitin proteins disclosed herein and determining whether the agent is capable of binding to ubiquitin.

Protein complexes comprising a deubiquitinase of the USP family and a conformationally stabilized ubiquitin protein can be any of the protein complexes disclosed herein containing any of the conformationally stabilized ubiquitin proteins disclosed herein as a component. The USP deubiquitinase component of the protein complex can be any member of the USP family, such as, but not limited to, any of USP1, USP2, USP3, USP4, USP5, USP6, USP7, USP8, USP9X, USP9Y, USP10, USP11, USP12, USP13, USP14, USP15, USP16, USP17, USP17L2, USP17L3, USP17L4, USP17L5, USP17L7, USP17L8, USP18, USP19, USP20, USP21, USP22, USP23, USP24, USP25, USP26, USP27X, USP28, USP29, USP30, USP31, USP32, USP33, USP34, USP35, USP36, USP37, USP38, USP39, USP40, USP41, USP42, USP43, USP44, USP45, or USP46. In another embodiment, the USP deubiquitinase is USP7, USP5, or USP14. Alternatively, the conformationally stabilized ubiquitin protein or fragment thereof or the USP deubiquitinase can be contained within a polypeptide, that is, either of the polypeptides comprising the protein complex used for the binding assay can comprise additional amino acid residues not present in the monomeric conformationally stabilized ubiquitin protein.

The binding assays described herein generally require contacting the two components to be tested for binding (for example, a protein complex comprising a conformationally stabilized ubiquitin protein and a USP deubiquitinase and an agent) under conditions and for a time sufficient to allow these components to interact. The complex formed can be isolated or detected in the reaction mixture. In one exemplary embodiment, one component (e.g., a protein complex, such as any described herein) is immobilized on a solid phase, e.g., on a microtiter place, by covalent or non-covalent attachments. Non-covalent attachment generally is accomplished by coating the solid surface with a solution of the agent and drying. Alternatively, an immobilized affinity molecule, such as an antibody, e.g., a monoclonal antibody, specific for the agent to be immobilized can be used to anchor it to a solid surface. The assay is performed by adding the non-immobilized component (e.g., an agent), which may be labeled by a detectable label, to the immobilized component, e.g., the coated surface containing the anchored component. When the reaction is complete, the non-reactive components are removed, e.g., by washing, and complexes anchored on the solid surface is detected. Where the originally non-mobilized component carries a detectable label, the detection of label immobilized on the surface indicates that binding occurred. Where the originally non-immobilized component does not carry a label, binding can be detected, for example, by using a labeled antibody specifically binding the immobilized complex.

In some embodiments, an agent that disrupts a protein complex formed between a conformationally stabilized ubiquitin protein and a member of the USP family of deubiquitinases is tested as follows: a reaction mixture is prepared containing the conformationally stabilized ubiquitin protein or fragment thereof and a member of the USP family of deubiquitinases under conditions and for a time allowing for the interaction and binding of the two components to form a protein complex. To test the ability of a candidate agent to disrupt the interaction between the protein complex comprising the deubiquitinase and the conformationally stabilized ubiquitin protein, the reaction is run in the absence and presence of a candidate agent. In addition, a placebo may be added to a separate reaction mixture to serve as a positive control. The binding between the candidate agent and the USP deubiquitinase is monitored as described above. The formation of a complex in the control reaction but not in the reaction mixture containing the candidate compound indicates that the candidate compound inhibits the binding of the conformationally stabilized ubiquitin protein to the binding partner. Furthermore, different amounts of the candidate agent can be tested to determine whether the inhibition of binding is competitive.

In an alternative method, a reaction can be conducted in a liquid phase, the reaction products separated from unreactive components, and complexes detected; e.g., using an immobilized antibody specific for the conformationally stabilized ubiquitin protein, the USP deubiquitinase, or the candidate agent to anchor any complexes formed in solution, and a labeled antibody specific for the other component of the possible complex can be used to detect the anchored complexes. Alternatively, cell-based assays can be used for binding assays. Specifically, cell lines (e.g., COS cells, CHO 3J cells, fibroblasts, etc.) that have been engineered to express a conformationally stabilized ubiquitin protein (e.g., by transfection or transduction with a ubiquitin variant DNA, etc.) as well as cells that naturally express or that have been engineered to express a USP deubiquitinase can be used.

The agent identified by methods described above can further be assayed for its binding specificity as further described below. Methods of identifying an agent that binds to a specific binding site can be carried out independently of the screening methods described above, or in conjunction with the inhibition screening assays. In other words, a method of identifying an agent that inhibits (such as partial or complete inhibition) the enzymatic activity of a member of the USP family of deubiquitinases can be carried out by first screening for agents that disrupt a protein complex comprising the deubiquitinase and a conformationally stabilized ubiquitin protein followed by identifying an agent from said screening results that bind to a specific binding site on the deubiquitinase (also referred to as "binding-based screening"). Alternatively, one can screen for agents that bind to a specific binding site on the deubiquitinase without first conducting an inhibition-based screening (or is followed by an inhibition-based assay).

In some embodiments, the inhibition-based screening and/or binding-based screening can be carried out in conjunction with a screening/identification method based on a functional readout of the agent. Functional readout of an agent that inhibits the activity of an enzyme known to interact with ubiquitin can be devised based on knowledge of biological activities associated with the ubiquitin/proteasome processing machinery, including, but not limited to, ubiquitin cleavage from target proteins, removal or incorporation of ubiquitin monomers into polyubiquitin chains, or protein degradation via the proteasome complex. The functional screening/identification method can be carried out either before or after the inhibition-based screening and/or the binding-based screening.

Thus, in some aspects, provided herein are methods for identifying an agent that binds (such as preferentially binds) to a protein complex comprising a deubiquitinase of the USP family and ubiquitin. The agent can be a small molecule chemical compound, an inhibitory nucleic acid, a protein (such as an inhibitory peptide or an antibody), or any combination thereof. In some embodiments, the methods comprise contacting the agent with any of the protein complexes comprising a conformationally stabilized ubiquitin protein and a USP deubiquitinase disclosed herein and determining whether the agent is capable of binding to the deubiquitinase or to the conformationally stabilized ubiquitin. In some embodiments, the agent disrupts the interaction between the conformationally stabilized ubiquitin and the deubiquitinase, thereby disrupting the protein complex. In some embodiments, the USP deubiquitinase component of the protein complex can be any member of the USP family, such as, but not limited to, any of USP1, USP2, USP3, USP4, USP5, USP6, USP7, USP8, USP9X, USP9Y, USP10, USP11, USP12, USP13, USP14, USP15, USP16, USP17, USP17L2, USP17L3, USP17L4, USP17L5, USP17L7, USP17L8, USP18, USP19, USP20, USP21, USP22, USP23, USP24, USP25, USP26, USP27X, USP28, USP29, USP30, USP31, USP32, USP33, USP34, USP35, USP36, USP37, USP38, USP39, USP40, USP41, USP42, USP43, USP44, USP45, or USP46. In some embodiments, the USP deubiquitinase is USP7, USP5, or USP14. In one embodiment, the USP deubiquitinase is USP7. In some embodiments, the agent competes with the binding of the deubiquitinase to the conformationally stabilized ubiquitin protein at an $IC_{50}$ of less than about 40 nM (for example, less than about 35 nM, 30 nM, 25 nM, 20 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM) under competitive ELISA assay. In some embodiments, the agent bound to ubiquitin suppresses the enzymatic activities of one or more binding partners, such as the enzymatic activity of a deubiquitinase of the USP family of deubiquitinases.

In some aspects, the agent that binds to a USP family deubiquitinase is an antibody. Antibodies are polypeptides that bind (such as preferentially bind) to any of USP family deubiquitinases disclosed herein. In some embodiments, the antibodies are USP family deubiquitinase (for example USP7, USP5, or USP14) antagonists.

In some aspects, the agent that binds to a USP family deubiquitinase is a non-antibody binding polypeptide. Binding polypeptides are polypeptides that bind (such as preferentially bind) to any of the USP family deubiquitinases disclosed herein. In some embodiments, the binding polypeptides are USP family deubiquitinase (for example USP7, USP5, or USP14) antagonists.

In some aspects, the agent that binds (such as preferentially binds) to a USP family deubiquitinase is a small molecule chemical compound. Small molecule chemical compounds are compounds that bind (such as preferentially bind) to any of the USP family deubiquitinases disclosed herein. In some embodiments, the small molecule chemical compounds are USP family deubiquitinase (for example USP7, USP5, or USP14) antagonists.

Also provided herein are agents identified by the methods of any of the claims disclosed herein.

D. Agents that Bind Conformationally Stabilized Ubiquitin Proteins, USP Deubiquitinases, or Protein Complexes Thereof.

In some aspects of any of the methods provided herein, an agent that binds (such as preferentially binds) to a stabilized conformational form of the ubiquitin protein (such as any of the conformationally stabilized forms of ubiquitin provided herein), that binds (such as preferentially binds) to a deubiquitinase of the USP family, or that binds to and/or disrupts a USP-deubiquitinase/conformationally stabilized ubiquitin protein complex can be an antibody, a non-antibody binding polypeptide, or a small molecule chemical compound.

1. Antibodies

In some aspects, the agent that binds (such as preferentially binds) to a specific conformational form of the ubiquitin protein (such as any of the conformationally stabilized forms of ubiquitin provided herein) is an antibody. Antibodies are polypeptides that bind to any of the conformationally stabilized ubiquitin proteins disclosed herein. In some embodiments, the antibodies are ubiquitin processing enzyme (such as any member of the E1, E2, or E3 family of ubiquitin processing enzymes) antagonists. In some embodiments, the antibodies are deubiquitinase (such as a member of the USP family of deubiquitinases, for example USP7, USP5, or USP14) antagonists.

Variants of antibodies can also be made based on information known in the art, without substantially affecting the activity of antibody. For example, antibody variants can have at least one amino acid residue in the antibody molecule replaced by a different residue. For antibodies, the sites of greatest interest for substitutional mutagenesis generally include the hypervariable regions, but framework region (FR) alterations are also contemplated.

For antibodies, one type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In one embodiment, the Fc region variant may display altered neonatal Fc receptor (FcRn) binding affinity. Such variant Fc regions may comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Fc region variants with reduced binding to an FcRn may comprise an amino acid modification at any one or more of amino acid positions 252, 253, 254, 255, 288, 309, 386, 388, 400, 415, 433, 435, 436, 439 or 447 of the Fc region, wherein the numbering of the residues in the Fc region is that of the EU index as in Kabat. The above-mentioned Fc region variants may, alternatively, display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat.

The Fc region variant with reduced binding to an Fc (R may comprise an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat.

For example, the Fc region variant may display reduced binding to an Fc (RI and comprise an amino acid modification at any one or more of amino acid positions 238, 265, 269, 270, 327 or 329 of the Fc region, wherein the numbering of the residues in the Fc region is that of the EU index as in Kabat.

The Fc region variant may display reduced binding to an Fc (RII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

The Fc region variant of interest may display reduced binding to an Fc (RIII and comprise an amino acid modification at one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

Fc region variants with altered (i.e. improved or diminished) C1q binding and/or Complement Dependent Cytotoxicity (CDC) are described in International Patent Application No.: WO99/51642. Such variants may comprise an amino acid substitution at one or more of amino acid positions 270, 322, 326, 327, 329, 331, 333 or 334 of the Fc region. See, also, Duncan & Winter Nature 322:738-40 (1988); U.S. Pat. No. 5,648,260; U.S. Pat. No. 5,624,821; and International Patent Application No.: WO94/29351 concerning Fc region variants.

2. Non-Antibody Binding Polypeptides

In some aspects, the agent that binds (such as preferentially binds) to a specific conformational form of the ubiquitin protein (such as any of the conformationally stabilized forms of ubiquitin provided herein) is a non-antibody binding polypeptide. Binding polypeptides are polypeptides that bind to any of the conformationally stabilized ubiquitin proteins disclosed herein. In some embodiments, the binding polypeptides are ubiquitin processing enzyme (such as any member of the E1, E2, or E3 family of ubiquitin processing enzymes) antagonists. In some embodiments, the binding polypeptides are deubiquitinase (such as a member of the USP family of deubiquitinases, for example USP7, USP5, or USP14) antagonists.

Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding to a target, such as any of the conformationally stabilized ubiquitin proteins disclosed herein. Binding polypeptides may be identified without undue experimentation using well known techniques. In this regard, it is noted that techniques for screening polypeptide libraries for binding polypeptides that are capable of binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth.*, 102:259-274 (1987); Schoofs et al., *J. Immunol.*, 140:611-616 (1988), Cwirla, S. E. et al., (1990) *Proc. Natl. Acad. Sci. USA*, 87:6378; Lowman, H. B. et al., (1991) *Biochemistry*, 30:10832; Clackson, T. et al., (1991) *Nature*, 352: 624; Marks, J. D. et al., (1991), *J. Mol. Biol.*, 222:581; Kang, A. S. et al., (1991) *Proc. Natl. Acad. Sci. USA*, 88:8363, and Smith, G. P. (1991) *Current Opin. Biotechnol.*, 2:668).

In this regard, bacteriophage (phage) display is one well known technique which allows one to screen large polypeptide libraries to identify member(s) of those libraries which are capable of binding to a target polypeptide, such as a c-met polypeptide. Phage display is a technique by which variant polypeptides are displayed as fusion proteins to the coat protein on the surface of bacteriophage particles (Scott, J. K. and Smith, G. P. (1990) *Science*, 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al., (1990) *Proc. Natl. Acad. Sci. USA*, 87:6378) or protein (Lowman, H. B. et al., (1991) *Biochemistry*, 30:10832; Clackson, T. et al., (1991) *Nature*, 352: 624; Marks, J. D. et al., (1991), *J. Mol. Biol.*, 222:581; Kang, A. S. et al., (1991) *Proc. Natl. Acad. Sci. USA*, 88:8363) libraries on phage have been used for screening millions of polypeptides or oligopeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., *Gene*, 215: 439 (1998); Zhu et al., *Cancer Research*, 58(15): 3209-3214 (1998); Jiang et al., *Infection & Immunity*, 65(11): 4770-4777 (1997); Ren et al., *Gene*, 195(2):303-311 (1997); Ren, *Protein Sci.*, 5: 1833 (1996); Efimov et al., *Virus Genes*, 10: 173 (1995)) and T7 phage display systems (Smith & Scott, *Methods in Enzymology*, 217: 228-257 (1993); U.S. Pat. No. 5,766,905) are also known.

Additional improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al., (1998) *Mol. Biotech.*, 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

The binding polypeptides can be modified to enhance their inhibitory and/or therapeutic effect (including, for example, enhanced affinity, improved pharmacokinetic properties such as half-life, stability, and clearance rate, reduced toxicity, etc.). Such modifications include, for example, glycosylation, pegylation, substitution with non-naturally occurring but functionally equivalent amino acid, linking groups, etc.

3. Small Molecules

In some aspects, the agent that binds (such as preferentially binds) to a specific conformational form of the ubiquitin protein (such as any of the conformationally stabilized forms of ubiquitin provided herein) is a small molecule chemical compound. Small molecule chemical compounds are compounds that bind to any of the conformationally stabilized ubiquitin proteins disclosed herein. In some embodiments, the small molecule chemical compounds are ubiquitin processing enzyme (such as any member of the E1, E2, or E3 family of ubiquitin processing enzymes) antagonists. In some embodiments, the small molecule chemical compounds are deubiquitinase (such as a member of the USP family of deubiquitinases, for example USP7, USP5, or USP14) antagonists.

Small molecules are preferably organic molecules other than binding polypeptides or antibodies as defined herein that bind (such as preferentially bind) to any of the conformationally stabilized ubiquitin proteins described herein. Organic small molecules may be identified and chemically synthesized using known methodology (see, e.g., PCT Publication Nos. WO00/00823 and WO00/39585). Organic small molecules are usually less than about 2000 Daltons in size, alternatively less than about 1500, 750, 500, 250 or 200 Daltons in size, wherein such organic small molecules that are capable of binding to a polypeptide as described herein may be identified without undue experimentation using well known techniques. In this regard, it is noted that techniques for screening organic small molecule libraries for molecules that are capable of binding to a polypeptide target are well known in the art (see, e.g., PCT Publication Nos. WO00/00823 and WO00/39585). Organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

In some aspects, the small molecule chemical compound is a component of a combinatorial chemical library. Combinatorial chemical libraries are a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of binding an acceptor molecule (such as a c-met protein) or mediating a biological activity of interest (such as, but not limited to, inhibition of cellular proliferation).

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. In some embodiments, the small molecules are less than about 2000 Daltons in size, alternatively less than about 1500, 750, 500, 250 or 200 Daltons in size.

The small molecule agents described in any of the aspects herein can be derived from any type of chemical reaction that can be carried out on a solid support. Such chemical reactions include, but are not limited to, 2+2 cycloadditions including trapping of butadiene; [2+3] cycloadditions including synthesis of isoxazolines, furans and modified peptides; acetal formation including immobilization of diols, aldehydes and ketones; aldol condensation including derivatization of aldehydes, synthesis of propanediols; benzoin condensation including derivatization of aldehydes; cyclocondensations including benzodiazepines and hydantoins, thiazolidines, turn mimetics, porphyrins, phthalocyanines; Dieckmann cyclization including cyclization of diesters; Diels-Alder reaction including derivatization of acrylic acid; Electrophilic addition including addition of alcohols to alkenes; Grignard reaction including derivatization of aldehydes; Heck reaction including synthesis of disubstituted alkenes; Henry reaction including synthesis of nitrile oxides in situ (see 2+3 cycloaddition); catalytic hydrogenation including synthesis of pheromones and peptides (hydrogenation of alkenes); Michael reaction including synthesis of sulfanyl ketones, bicyclo[2.2.2]octanes; Mitsunobu reaction including synthesis of aryl ethers, peptidyl phosphonates and thioethers; nucleophilic aromatic substitutions including synthesis of quinolones; oxidation including synthesis of aldehydes and ketones; Pausen-Khand cycloaddition including cyclization of norbornadiene with pentynol; photochemical cyclization including synthesis of helicenes; reactions with organometallic compounds including derivatization of aldehydes and acyl chlorides; reduction with complex hydrides and tin compounds including reduction of carbonyl, carboxylic acids, esters and nitro groups; Soai reaction including reduction of carboxyl groups; Stille reactions including synthesis of biphenyl derivatives; Stork reaction including synthesis of substituted cyclohexanones; reductive amination including synthesis of quinolones; Suzuki reaction including synthesis of phenylacetic acid derivatives; and Wittig-Horner reactions including reactions of aldehydes, pheromones, and sulfanyl ketones.

References disclosing the synthesis of chemical libraries as well as the deconvolution of the individual compounds of those libraries onto individual solid phase supports, can be found in U.S. Patent Application No. 2009/0032592; Needels et al., (1993), *Proc. Natl. Acad. Sci. USA* 90: 10700-10704; and WO 97/15390.

E. Methods for Using Conformationally Stabilized Ubiquitin Proteins to Determine Ubiquitin-Associated Protein Complex Components In some aspects, provided herein are methods for using any of the conformationally stabilized ubiquitin proteins disclosed herein to determine ubiquitin-associated protein complex components in animal cells. Given the transient nature of wildtype ubiquitin associations with ubiquitin binding proteins and processing enzymes, the stabilized ubiquitin proteins described above can be useful for ascertaining one or more components of ubiquitin-associated protein complexes in cells. As essentially all animal cells express ubiquitin, the methods are applicable for use in all animal cells, whether the methods are conducted in vitro, in vivo, or ex vivo. In some embodiments, a nucleic acid encoding any of the conformationally stabilized ubiquitin proteins disclosed herein can be transfected into an animal cell. In some embodiments, the nucleic acid is integrated into the genome of an animal cell under the control of either an inducible or constitutive promoter. In some embodiments, the nucleic acid is under the control of either an inducible or constitutive promoter and is transiently transfected into the animal cell. In yet another embodiment, a transgenic non-human animal comprising the nucleic acid can be produced according to methods well known in the art. In any of the above embodiments, the nucleic acid encoding the conformationally stabilized ubiquitin protein can further comprise an affinity tag. In some embodiments, the affinity can be, without limitation, a His tag (for example, a tag comprising at least 6 histadine residues (SEQ ID NO: 2)), a maltose binding protein tag, an HA tag, or a GST tag. In some embodiments, animal cells comprising any of the conformationally stabilized ubiquitin proteins disclosed herein can be lysed and ubiquitin-associated protein complexes obtained through any number of methods known in the art. These include, without limitation, immunoprecipitation, affinity purification, chromatographic methods, such as, but not limited to, size exclusion chromatography. The identity of proteins associated with any of the conformationally stabilized ubiquitin proteins disclosed herein can then be ascertained through well-known methods such as, but not limited to, 2D gel electrophoresis and mass spectrometry.

In some aspects, any of the conformationally stabilized ubiquitin proteins described herein can be used as a gain-of-function genetic tool to screen for downstream components of the ubiquitin processing/proteolysis pathway. For example, any of the proteins described herein can be expressed in yeast to search for proteins that interact with, for example, enzymes of the ubiquitin conjugation machinery, ubiquitin specific proteases, and components of the proteosome, according to methods known in the art.

As such, provided herein is a method for using a conformationally stabilized ubiquitin protein (such as any of the conformationally stabilized ubiquitin proteins disclosed herein) to determine the components of a ubiquitin-associated protein complex. In some embodiments, the method comprises 1) expressing a conformationally stabilized ubiquitin protein in an animal cell; 2) isolating an ubiquitin-associated protein complex; and 3) ascertaining the identity of one or more proteins associated with the conformationally stabilized ubiquitin protein in the animal cell. In some embodiments, the animal cell is a human cell, a non-human primate cell, a rodent cell, a yeast cell, a *Drosophila* cell, or a zebrafish cell. In some embodiments, the animal cell is a cancer cell. In some embodiments, the ubiquitin-associated protein complex is isolated by immunoprecipitation, affinity tag chromatography, or some other chromatographic method (such as, but not limited to, size exclusion chromatography, ion exchange chromatography, or hydrophobic chromotography).

F. Methods for Screening for a Conformationally Stabilized Form of a Protein

The present invention also provides for methods for screening for a conformationally stabilized form of a protein, wherein the conformationally stabilized protein has increased binding affinity to a binding partner or an increased ability to modulate the activity of the binding partner (such as an enzymatic activity) as compared to the wildtype protein. In some aspects, the method comprises contacting the binding partner with a library of mutant forms of the protein, wherein the library of mutant forms is produced by substituting one or more amino acid residues of the conformationally dynamic protein with other amino acid residues at one or more preselected locations, wherein said preselected locations are located in the interior of the protein and identifying the conformationally stabilized protein based on a binding to the binding partner or an increased ability to modulate (such as to increase or to decrease) the activity (such as an enzymatic activity) of the binding partner as compared to the wildtype protein. In one embodiment, the substitution is a random substitution. The protein may be any protein that naturally exhibits multiple conformational states. In some embodiments, multiple conformational states in a protein can be evaluated by structural assays such as NMR or X-ray crystallography or functional assays such as binding assays. In some embodiments, a conformationally dynamic protein has motion in its apo state. In some embodiments, a conformationally dynamic protein has motion as evaluated by NMR or X-ray crystallography. Proteins that exhibit multiple conformational states can include, but are not limited to, ubiquitin proteins, enzymes (e.g., HIV proteases or Ras), nuclear hormone receptors (e.g., the estrogen receptor or the androgen receptor), or G-protein coupled receptors (GPCRs). In some embodiments, the substitutions result in the formation of one or more disulfide bonds in the protein. In another embodiment, the substitutions do not result in the formation of one or more disulfide bonds in the protein. In some embodiments, additional substitutions (at random or preselected locations) are made in addition to substitutions at those preselected residues in the interior of the protein.

In some aspects, preselected amino acid residues in the interior of the protein suitable for substitution with other amino acid residues can be selected based on the contribution of the amino acid residues at each location to the overall conformational dynamics within the protein or within a region of the protein. In one embodiment, series of solved high-resolution crystal structures of the conformationally dynamic protein can be used to reveal one or more preferential conformational state(s) the dynamic protein adopts either in solution or when bound to a binding partner. Based on the position of the protein or region of the protein identified using the crystal structures, amino acid residues located within the interior of the conformationally dynamic protein can be identified using a computational search. In one embodiment, the computational search is a single-state RosettaDesign. In another embodiment, the computational search is a multi-state RosettaDesign.

Candidate conformationally stabilized proteins can be assessed by any number of methods. The characteristics of conformationally stabilized proteins can be assessed by determining the ability of the conformationally stabilized proteins to modulate the interaction between the wildtype protein and a binding partner. One of the important characteristics is binding affinity. The binding characteristics of candidate conformationally stabilized proteins of interest can be assessed in any of a number of ways known in the art. Another method to assess a candidate conformationally stabilized protein is to examine the extent of conformational stability of its protein backbone using techniques such as $R_2$ dispersion experiments (sensitive to motion on millisecond timescales) and/or $H_ZN_Z R_{1\rho}R_{ex}$ measurements (sensitive to motion on microsecond timscales).

Also provided herein is a method for screening for a conformationally stabilized ubiquitin protein, wherein the conformationally stabilized ubiquitin has increased binding affinity to a binding partner or an increased ability to modulate (such as to increase or decrease) the activity of the binding partner as compared to wildtype ubiquitin. In some embodiments, the method comprises contacting the binding partner with a library of mutant forms of the ubiquitin protein, wherein the library of mutant forms is produced by randomly substituting an amino acid residue in the amino acid sequence of wildtype ubiquitin with another amino acid residue at one or more preselected locations in the interior of the protein and identifying the conformationally stabilized ubiquitin based on a binding to the binding partner or an increased ability to modulate the activity of the binding partner as compared to wildtype ubiquitin. In some embodiments, the binding partner is a USP deubiquitinase. In some embodiments, the conformationally stabilized ubiquitin selectively inhibits (such as completely inhibits) the enzymatic activity of the USP deubiquitinase. In one embodiment, the deubiquitinase is USP7. Also provided herein is a library of ubiquitin proteins, wherein the ubiquitin proteins in the library comprise one or more random substitutions with another amino acid at amino acid residue positions located at A7, A8, A13, A34, A36, A69, and A71, wherein the amino acid position is relative to SEQ ID NO:1.

An initial step in the process can include generating one or more candidate conformationally stabilized proteins comprising sequences of interest, which are then displayed under conditions suitable to determine their binding characteristics to a binding partner. For example, candidate conformationally stabilized proteins can be displayed as carboxyl-terminal (C-terminal) display libraries of peptides on the surface of a phage or phagemid, for example a filamentous phage(mid) using protein fusions with a coat protein such as p3 or p8. C-terminal display is known in the art. See, e.g., Jespers et al., Biotechnology (NY). 13:378-82 and WO 00/06717. These methods may be used to prepare the fusion genes, fusion proteins, vectors, recombinant phage particles, host cells and libraries thereof described herein. As described herein, in some embodiments, it may be useful to display candidate conformationally stabilized proteins as amino-terminal (N-terminal) display libraries of peptides on the surface of a phage or phagemid. Methods of N-terminal phage(mid) display include those described herein, and those that are well known in the art, e.g., as described in U.S. Pat. No. 5,750,373 (and references cited therein). Methods of characterizing binder molecules obtained by these methods are also known in the art, including those disclosed in the references cited above (Jespers et al., WO 00/06717 & U.S. Pat. No. 5,750,373) and as described herein.

1. Isolation of Binding Phage

A phage display library with the displayed candidate conformationally stabilized proteins is contacted with a binding partner or fragment thereof in vitro to determine those members of the library that bind to a polypeptide. Any method known to the skilled artisan may be used to assay for in vitro protein binding. For example, 1, 2, 3 4, or 5 rounds or more of binding selection (a.k.a "panning") may be performed, after which individual phage are isolated and, optionally, analyzed in a phage ELISA. Binding affinities of peptide-displaying phage particles to immobilized polypeptide may be determined using a phage ELISA (Barrett et al., *Anal Biochem.* 204:357-64 (1992)).

In a situation wherein the candidate is being assessed for the ability to compete with a known conformationally stabilized protein for binding to polypeptide, the appropriate binding competition conditions are provided. For example, in one embodiment, screening/selection/biopanning can be performed in the presence of one or more concentrations of the known conformationally stabilized protein. In another embodiment, conformationally stabilized proteins isolated from the library can be subsequently assessed in a competitive ELISA assay in the presence of the known conformationally stabilized protein.

2. Preparation of Conformationally Stabilized Proteins

The conformationally stabilized proteins may be produced conveniently as protein fragments containing a stabilized domain or as fusion polypeptides using conventional synthetic or recombinant techniques. Fusion polypeptides are useful in phage(mid) display wherein the polypeptide is the target, in expression studies, cell-localization, bioassays, ELISAs (including binding competition assays), etc. The fusion protein can then be purified according to known methods using affinity chromatography and a capture reagent that binds to the second polypeptide. The polypeptide may be fused to an affinity sequence, e.g. the C-terminus of the GST (glutathione S-transferase) sequences. Such fusion proteins facilitate the purification of the recombinant polypeptide using, e.g., glutathione bound to a solid support and/or attachment to solid support (e.g., a matrix for peptide screening/selection/biopanning). Additional exemplary fusions are presented in Table 7, including some common uses for such fusions.

Fusion proteins can be easily created using recombinant methods. A nucleic acid encoding the polypeptide (or portion thereof) can be fused in-frame with a second domain encoding nucleic acid, at the N terminus, C-terminus or internally of the polypeptide. In some embodiments, the second domain is fused at the C-terminus of the polypeptide. Fusion genes may also be synthesized by conventional techniques, including automated DNA synthesizers. PCR amplification using anchor primers that give rise to complementary overhangs between two consecutive gene fragments that can subsequently be annealed and reamplified to generate a chimeric gene sequence is also useful. Many vectors are commercially available that facilitate sub-cloning the polypeptide in-frame to a fusion protein.

TABLE 7

Useful Second Polypeptides For Fusion Proteins

| Fusion partner | in vitro | in vivo |
|---|---|---|
| Human growth hormone (hGH) | Radioimmuno-assay | none |
| β-glucuronidase (GUS) | Colorimetric, fluorescent, or chemi-luminescent | colorimetric (histo-chemical staining with X-gluc) |
| Green fluorescent protein (GFP) and related molecules (RFP, BFP, YFP domain, etc.) | Fluorescent | fluorescent |
| Luciferase (firefly) | Bioluminsecent | Bioluminescent |
| Chloramphenicoal acetyltransferase (CAT) | Chromatography, differential extraction, fluorescent, or immunoassay | none |
| β-galactosidase | Colorimetric, fluorescence, chemi-luminescence | colorimetric (histochemical staining with X-gal), bio-luminescent in live cells |
| Secrete alkaline phosphatase (SEAP) | Colorimetric, bioluminescent, chemi-luminescent | none |
| Tat from HIV | Mediates delivery into cytoplasm and nuclei | Mediates delivery into cytoplasm and nuclei |

As an example of a fusion protein, GST-polypeptide fusion may be prepared from a gene of interest in the following manner. With the full-length gene of interest as the template, the PCR is used to amplify DNA fragments encoding the polypeptide using primers that introduce convenient restriction endonuclease sites to facilitate sub-cloning. Each amplified fragment is digested with the appropriate restriction enzymes and cloned into a similarly digested plasmid, such as pGEX6P-3 or pGEX-4T-3, that contains GST and is designed such that the sub-cloned fragments will be in-frame with the GST and operably linked to a promoter, resulting in plasmids encoding GST-polypeptide.

To produce the fusion protein, E. coli cultures harboring the appropriate expression plasmids are generally grown to mid-log phase ($A_{600}$=1.0) in LB broth, e.g. at about 37° C., and may be induced with IPTG. The bacteria are pelleted by centrifugation, resuspended in PBS and lysed by sonication. The suspension is centrifuged, and GST-polypeptide are purified from the supernatant by affinity chromatography on 0.5 ml of glutathione-Sepharose.

It will be apparent to one of skill in the art that many variations will achieve the goal of isolating a conformationally stabilized protein and may be used in this invention. For example, the conformationally stabilized protein fused to an epitope tag may be constructed as described above and the tags used to affinity purify the conformationally stabilized protein. Conformationally stabilized protein may also be prepared without any fusions; in addition, instead of using the microbial vectors to produce the conformationally stabilized protein, in vitro chemical synthesis may instead be used. Other cells may be used to produce conformationally stabilized protein, such as other bacteria, mammalian cells (such as COS), or baculoviral systems. A wide variety of polynucleotide vectors to produce a variety of fusions are also available. The final purification of a conformationally stabilized protein will generally depend on the fusion partner; for example, a poly-histidine tag fusion can be purified on nickel columns 3. Determining the Sequence of the Conformationally Stabilized Protein Phage(mid) that bind to the binding partner with the desired characteristics (and optionally, does not bind to unrelated sequences), can be subjected to sequence analysis. The phage(mid) particles displaying the candidate conformationally stabilized protein are amplified in host cells, the DNA isolated, and the appropriate portion of the genome (encoding the candidate peptide) sequenced using any appropriate known sequencing technique.

4. Further Enhancement of Binding Via Affinity Maturation

In some aspects, the binding of a conformationally stabilized protein to a binding partner can be further enhanced via affinity maturation. In affinity maturation (Levin and Weiss, Mol. BioSyst. 2:49, 2006), residues on the surface of a protein are varied using mutagenesis, and the resulting mutated proteins are screened for improved binding to a binding partner. Several methods of affinity maturation are known in the art. These include affinity maturation via phage (Gram et al. PNAS 89:3576, 1992; Lowman et al., J. Mol. Biol., 1993, 234, 564), ribosome-display (Lipovsek et al. J. Immunol. Methods 290 (2004), pp. 51-67), yeast surface-display (Graff et al. Protein Eng. Des. Sel. 17 (2004), pp. 293-304), error-prone PCR (Schlapschy et al. Protein Eng. Des. Sel. 17 (2004), pp. 847860), mutator bacterial strains (Low et al. J. Mol. Biol. 260: 359, 1996), stepwise focused mutagenesis (Wu et al. PNAS 95:6037, 1998) and saturation mutagenesis (Nishimiya et al. J. Biol. Chem. 275:12813, 2000; Yang et al. J. Mol. Biol. 254:392, 1995; Chowdhury and Pastan, Nat. Biotechnol. 17:568, 1999). Other techniques often use alanine-scanning or site-directed mutagenesis to generate limited collections of specific variants.

5. Binding Assays

Forming a complex of a conformationally stabilized protein and a binding partner facilitates separation of the complexed from the uncomplexed forms thereof and from impurities. Conformationally stabilized protein fusions can be formed in solution or where one of the binding partners is bound to an insoluble support. The complex can be separated from a solution, for example using column chromatography, and can be separated while bound to a solid support by filtration, centrifugation, etc. using well-known techniques. Binding the conformationally stabilized protein therefor to a solid support facilitates high throughput assays.

Test compounds can be screened for the ability to modulate (e.g., increase) the interaction and/or activity of a conformationally stabilized protein with binding partner in the presence and absence of a candidate binding compound, and screening can be accomplished in any suitable vessel, such as microtiter plates, test tubes, and microcentrifuge tubes. Fusion proteins can also be prepared to facilitate testing or separation, where the fusion protein contains an additional domain that allows one or both of the proteins to be bound to a matrix. For example, GST-conformationally stabilized protein fusion proteins can be adsorbed onto glutathione sepharose beads (SIGMA Chemical, St. Louis, Mo.) or glutathione derivatized microtiter plates that are then combined with the test compound or the test compound and the mixture is incubated under conditions allowing complex formation (e.g., at physiological conditions of salt and pH). Following incubation, the beads or microtiter plate wells are washed to remove any unbound components, the matrix immobilized in the case of beads, and the complex determined either directly or indirectly. Alternatively, the fusions can be dissociated from the matrix, and the level of binding or activity determined using standard techniques.

Other fusion polypeptide techniques for immobilizing proteins on matrices can also be used in screening assays. Either a conformationally stabilized protein or a binding partner can be immobilized using biotin-avidin or biotin-streptavidin systems. Biotinylation can be accomplished using many reagents, such as biotin-N-hydroxy-succinimide (NHS; PIERCE Chemicals, Rockford, Ill.), and immobilized in wells of streptavidin coated 96 well plates (PIERCE Chemical). Alternatively, antibodies reactive with the conformationally stabilized protein or the binding partner but do not interfere with binding of a binding peptide to its target molecule can be derivatized to the wells of the plate, and unbound conformationally stabilized protein or binding partner trapped in the wells by antibody conjugation. Methods for detecting such fusions, in addition to those described for the GST-immobilized fusions, include immunodetection of fusions using antibodies reactive with the binding partners or the conformationally stabilized protein.

6. Assay for Binding: ELISA

To assess the binding affinities of a conformationally stabilized protein, competition binding assays may be used, where the ability of the conformationally stabilized protein to bind a binding partner (and the binding affinity, if desired) is assessed and compared to that of a compound known to bind the conformationally stabilized protein, for example, a high-affinity binder peptide determined by phage display as described herein.

Many methods are known and can be used to identify the binding affinities of conformationally stabilized proteins to a binding partner; for example, binding affinities can be determined as a Kd values using ELISAs. For example, in solid phase assays, assay plates may be prepared by coating microwell plates (preferably treated to efficiently adsorb protein) with neutravidin, avidin or streptavidin. Non-specific binding sites are then blocked through addition of a solution of bovine serum albumin (BSA) or other proteins (for example, nonfat milk) and then washed, preferably with a buffer containing a detergent, such as Tween-20. A biotinylated known conformationally stabilized protein (for example, the phage peptides as fusions with GST or other such molecule to facilitate purification and detection) is prepared and bound to the plate. Serial dilutions of the binding partner to be tested are prepared and contacted with the bound conformationally stabilized protein. The plate coated with the immobilized conformationally stabilized protein is washed before adding each binding reaction to the wells and briefly incubated. After further washing, the binding reactions are detected, often with an antibody recognizing the fusion partner and a labeled (such as horseradish peroxidase (HRP), alkaline phosphatase (AP), or a fluorescent tag such as fluorescein) secondary antibody recognizing the primary antibody. The plates are then developed with the appropriate substrate (depending on the label) and the signal quantified, such as using a spectrophotometric plate reader. The absorption signal may be fit to a binding curve using a least squares fit. Thus the ability of various binding partner to bind the conformationally stabilized protein can be measured.

V. Examples of Uses

The identification and characterization of the conformationally stabilized proteins (such as a conformationally stabilized ubiquitin protein) as described herein provide valuable insights into the cellular functions of the wildtype protein and provides compositions and methods for modulating the in vivo interactions between these proteins and their binding partner(s). For example, these conformationally stabilized proteins can be utilized to enhance in vivo binding interactions and alter the activity (e.g., an enzymatic activity) of one or more binding partners. Homologs can be generated conveniently based on their binding and/or functional characteristics relative to the well-characterized conformationally stabilized proteins provided herein. These conformationally stabilized protein homologues can further be utilized to identify cellular proteins associated with wildtype conformationally dynamic proteins and their binding partners present in protein complexes in vivo.

Well-characterized moderate to high affinity conformationally stabilized proteins (such as a conformationally stabilized ubiquitin protein, such as any of those described herein) can be further used to elucidate important structural characteristics of the binding partner itself. The invention provides conformationally stabilized protein variants as disclosed herein that have enhanced ability to bind and/or activate one or more binding partner targets. Other variants can be similarly identified.

Conformationally stabilized proteins developed based on methods described herein can be used to achieve the modulatory effect of interest. For example, such manipulation may include activation of the association between the conformationally stabilized protein and its cognate binding partner (e.g., in the case of ubiquitin, a deubiquitinase). In another example, such manipulation may include modulatory (such as increased or decreased) effects through, for example, induction of cellular functions as a result of binding of the conformationally stabilized protein or through enhancement of association between the conformationally stabilized protein and its cognate binding partner.

Other uses of conformationally stabilized proteins (such as a conformationally stabilized ubiquitin protein) include diagnostic assays for diseases related to the wildtype form of the protein (e.g., the wildtype conformationally dynamic form of the protein) and its associating partners, the use of the conformationally stabilized protein and binding partners in fusion proteins as purification handles and anchors to substrates.

Identification of conformationally stabilized proteins (such as a conformationally stabilized ubiquitin protein) capable of binding to the binding partners (such as a deubiquitinase of the USP family) at varying affinities, as described herein, provide useful avenues for modulating biologically important interactions in vivo. Thus, identification of conformationally stabilized proteins which are capable of modulating these interactions points to avenues of therapeutic and/or diagnostic applications and strategies that would not be possible in the absence of knowledge of such molecules and interactions.

Conformationally stabilized proteins (such as a conformationally stabilized ubiquitin protein) can be delivered into live cells using appropriate routes of administration known in the art, e.g., via microinjection, antenapedia peptide or lipid transfection reagents in order to modulate, and in some instances validate the physiological importance of the conformationally stabilized form of the protein and its interaction with one or more binding partners in a particular tissue, cell, organ or pathological condition. Suitable assays exist to monitor the conformationally stabilized protein's interaction with a binding partner and the physiological effect of modulation of said interaction. Finally, stabilized proteins may be delivered into live cells or animal models which are models for a disease (i e mimic certain properties of a disease) to determine if binding or interaction with a binding partner of interest provides an outcome consistent with expectations for therapeutic benefit.

Methods of detecting protein-protein (or peptide) interactions in vivo are known in the art. For example, the methods described by Michnick et al. in U.S. Pat. Nos. 6,270,964 B1 & 6,294,330 B1 can be used to analyze interactions and/or activity of the conformationally stabilized protein (including any described herein) and a cognate binding partner (including any described herein).

Conformationally stabilized proteins can be used as tools for any of the methods described above for conformationally stabilized ubiquitin proteins. For example, conformationally stabilized proteins can be used as tools 1) to screen for agents that bind (such as preferentially bind) to the conformationally stabilized protein; 2) to screen for agents that disrupt a conformationally stabilized protein/binding partner protein complex; 3) to inhibit the enzymatic activity of one or more binding partners; or 4) to determine the identity of one or more components of a protein complex that associates with the conformationally stabilized protein in a cell that expresses the wildtype form of the stabilized protein). Additionally, the conformationally stabilized proteins are not limited merely to these uses, but may also be used as tools according to any other method known in the art.

The conformationally stabilized ubiquitin proteins described herein can be used to inhibit the deubiquitination of a deubiquitinase target protein in vivo. For example, a conformationally stabilized ubiquitin protein that is inhibitory with respect to the enzymatic activity of a deubiquitinase specific for a target protein can be used to prevent the deubiquitination of that target protein if expressed in an animal cell. Use of a conformationally stabilized ubiquitin protein in this manner could increase the chances that the target protein would undergo proteolytic degradation in the proteosome, for example. Similarly, the conformationally stabilized ubiquitin proteins disclosed herein can be used in vivo to enhance or maintain the ubiquitinated state of one or a class of target proteins. For example, one such target protein is the oncoprotein Mdm2, which is involved in the development of several types of cancers including soft tissue sarcomas and osteosarcomas as well as breast tumors. The deubiquitinase USP7 specifically deubiquitinates Mdm2, which in turn leads to a downregulation of the p53 tumor suppressor protein. Accordingly, use of a conformationally stabilized ubiquitin protein (such as any of those described herein) to inhibit the enzymatic activity of USP7 could indirectly lead to the maintenance of p53 tumor suppressor protein.

VI. Pharmaceutical Formulations

Pharmaceutical formulations of a conformationally stabilized protein (such as a conformationally stabilized ubiquitin protein) as described herein are prepared by mixing such conformationally stabilized proteins having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The formulation herein may also contain more than one active ingredients as necessary for the particular indication being treated, preferably those with complementary activities that do not adversely affect each other. Such active ingredients are suitably present in combination in amounts that are effective for the purpose intended.

Conformationally stabilized proteins (such as a conformationally stabilized ubiquitin protein) may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the conformationally stabilized protein (such as a conformationally stabilized ubiquitin protein), which matrices are in the form of shaped articles, e.g. films, or microcapsules.

The formulations to be used for in vivo administration are generally sterile. Sterility may be readily accomplished, e.g., by filtration through sterile filtration membranes VII. Therapeutic Uses of Conformationally Stabilized Proteins and Agents Obtained from Screening Agents that have the property of increasing or decreasing the activity (such as an enzymatic activity) of a binding partner of a conformationally dynamic protein (e.g., ubiquitin) are useful. This modulation in activity may come about in a variety of ways, for example by administering to a subject in need thereof an effective amount of one or more of the (such as a conformationally stabilized proteins (such as a conformationally stabilized ubiquitin protein) described herein or by administering any of the agents obtained from any of the screening methods described herein.

Any of the conformationally stabilized proteins or any of the agents obtained using any of the screening methods described herein may be used in therapeutic methods. In one aspect, a conformationally stabilized protein (such as a conformationally stabilized ubiquitin protein) for use as a medicament is provided. In one such embodiment, the method further comprises administering to the individual an effective amount of at least one additional therapeutic agent, e.g., as described below. An "individual" according to any of the above embodiments is preferably a human. In a further aspect, the invention provides for the use of a conformationally stabilized protein (such as a conformationally stabilized ubiquitin protein) in the manufacture or preparation of a medicament. In one such embodiment, the method further comprises administering to the individual an effective amount of at least one additional therapeutic agent, e.g., as described below. An "individual" according to any of the above embodiments may be a human.

In another aspect, an agent obtained from any of the screening methods disclosed herein for use as a medicament is provided. In one such embodiment, the method further comprises administering to the individual an effective amount of at least one additional therapeutic agent, e.g., as described below. An "individual" according to any of the above embodiments is preferably a human. In a further aspect, the invention provides for the use of an agent obtained from any of the screening methods disclosed herein in the manufacture or preparation of a medicament. In one such embodiment, the method further comprises administering to the individual an effective amount of at least one additional therapeutic agent, e.g., as described below.

In a further aspect, provided herein are pharmaceutical formulations comprising any of the conformationally stabilized proteins (such as a conformationally stabilized ubiquitin protein) or agents obtained from any of the screening methods disclosed herein, e.g., for use in any of the above therapeutic methods. In one embodiment, a pharmaceutical formulation comprises any of the conformationally stabilized proteins provided herein and a pharmaceutically acceptable carrier. In one embodiment, a pharmaceutical formulation comprises an agent obtained from any of the screening methods disclosed herein and a pharmaceutically acceptable carrier. In another embodiment, a pharmaceutical formulation comprises any of the conformationally stabilized proteins provided herein or an agent obtained from any of the screening methods disclosed herein and at least one additional therapeutic agent, e.g., as described below.

The conformationally stabilized proteins described herein or any of the agents obtained from any of the screening methods disclosed herein can be used either alone or in combination with other agents in a therapy. For instance, a conformationally stabilized protein of the invention may be co-administered with at least one additional therapeutic agent.

Such combination therapies noted above encompass combined administration (where two or more therapeutic agents are included in the same or separate formulations), and separate administration, in which case, administration of the conformationally stabilized proteins described herein can occur prior to, simultaneously, and/or following, administration of the additional therapeutic agent.

A conformationally stabilized proteins described herein (such as a conformationally stabilized ubiquitin protein) or any of the agents obtained from any of the screening methods disclosed herein (and any additional therapeutic agent) can be administered by any suitable means, including parenteral, intrapulmonary, and intranasal, and, if desired for local treatment, intralesional administration, topical administration, or intraocular administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Conformationally stabilized proteins (such as a conformationally stabilized ubiquitin proteins) and/or agents obtained from any of the screening methods disclosed herein should be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The conformationally stabilized protein or an agent obtained from any of the screening methods disclosed herein need not be, but is optionally formulated with one or more agents currently used to prevent or treat the disorder in question. The effective amount of such other agents depends on the amount of the conformationally stabilized protein present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a conformationally stabilized protein or an agent obtained from any of the screening methods described herein (when used alone or in combination with one or more other additional therapeutic agents) will depend on the type of disease to be treated, the type of conformationally stabilized proteins (e.g., a conformationally stabilized ubiquitin protein) or agent obtained from any of the screening methods disclosed herein (for example an antibody or a small molecule chemical compound), the severity and course of the disease, whether the conformationally stabilized protein or agent obtained from any of the screening methods disclosed herein is administered for preventive or therapeutic purposes, previous therapy, the patient's clinical history and response to the conformationally stabilized protein or agent, and the discretion of the attending physician. The conformationally stabilized protein or agent obtained from any of the screening methods disclosed herein is suitably administered to the patient at one time or over a series of treatments. Depending on the type and severity of the disease, about 10 ng/kg to up to about 100 mg/kg (e.g., 0.01 to about 500 mg/kg) of conformationally stabilized protein or agent can be an initial candidate dosage for administration to the patient, whether, for example, by one or more separate administrations, or by continuous infusion. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage may be about any of 0.05 to 0.5, 0.5 to 5 or 5 to 50 mg/kg per day. For oral administration, the compositions are preferably provided in the form of tablets containing about 1.0 to about 1000 milligrams of the active ingredient, particularly about any of 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. Such doses may be administered intermittently, e.g. every week or every three weeks (e.g. such that the patient receives from about two to about twenty, or e.g.

about six doses of the conformationally stabilized protein. An initial higher loading dose, followed by one or more lower doses may be administered. However, other dosage regimens may be useful. The progress of this therapy is easily monitored by conventional techniques and assays.

VIII. Articles of Manufacture

In another, an article of manufacture containing materials useful for the treatment, prevention and/or diagnosis of the disease and/or disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disease and/or disorder and may have a sterile access port (for example the container may be an intravenous solution bag or a vial having a stopper pierceable by a hypodermic injection needle). At least one active agent in the composition is a conformationally stabilized protein (such as a conformationally stabilized ubiquitin protein) or an agent obtained from any of the screening methods disclosed herein. The label or package insert indicates that the composition is used for treating the disease and/or disorder of choice. Moreover, the article of manufacture may comprise (a) a first container with a composition contained therein, wherein the composition comprises a conformationally stabilized protein described herein or an agent obtained from any of the screening methods disclosed herein; and (b) a second container with a composition contained therein, wherein the composition comprises an additional therapeutic agent. The article of manufacture in this embodiment of the invention may further comprise a package insert indicating that the compositions can be used to treat a particular disease and/or disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user stand point, including other buffers, diluents, filters, needles, and syringes.

EXAMPLES

The following are examples of methods and compositions of the invention. It is understood that various other embodiments may be practiced, given the general description provided above.

Example 1

Engineering a Conformationally Stabilized Ubiquitin Protein

This example illustrates the novel technique of Conformational Display for the identification and engineering of conformationally stabilized proteins. In contrast to traditional phage display, which typically mutates surface positions to find new enthalpic contacts, Conformational Display screens buried amino acid residues to identify new packing arrangements that result in conformations optimal for binding. A flexible molecule with a minority of tight-binding conformations is thereby converted into a stabilized molecule that primarily adopts a high affinity conformation (FIG. 1A).

Cellular signaling cascades frequently converge upon "hub" proteins, which are recognized by a large number of binding partners.[23] Ubiquitin is a highly conserved eukaryotic signaling hub, which is post-translationally attached to a substrate protein lysine via an isopeptide bond with ubiquitin's carboxy terminus. Each ubiquitin linkage type carries a distinct signal, and the tightly regulated processing of ubiquitin chains is used to convey a wide variety of cellular information.[24] Accordingly, misregulation of ubiquitin processing has been implicated in several disease states, including oncogenesis and neurodegeneration.[25-26]

Ubiquitin is canonically attached to substrates through a three-part E1-E2-E3 enzymatic cascade. The removal of ubiquitin is catalyzed by several families of isopeptidases known as deubiquitinases (DUBs). There are approximately 100 human DUBs, each with distinct substrate specificities and enzymatic properties, implying a largely unexplored wealth of signal regulation. Two prominent DUB families are the Ubiquitin C-terminal Hydrolase (UCH) and Ubiquitin Specific Protease (USP) enzymes. UCHs are responsible primarily for recycling ubiquitin by removing small moieties such as intracellular nucleophiles and short peptides from its carboxy terminus. USPs act typically as signaling modulators, regulating ubiquitin chain length by cleaving the isopeptide bond that connects large moieties (such as whole proteins) to ubiquitin.[27]

Recent NMR and computational studies of apo ubiquitin, relying heavily on the thorough analysis of a large set of residual dipolar couplings (RDCs), have suggested that the conformational plasticity of ubiquitin may be fundamental to its recognition by certain partners.[28] This work indicated that the $\beta1$-$\beta2$ loop region is mobile on the fast microsecond timescale and that binding partners may select distinct conformations out of this preexisting equilibrium, although there have been several competing reports that ubiquitin interactions cannot be solely attributed to a conformational selection binding mechanism.[29-30] Although these studies have highlighted the importance of conformational dynamics in ubiquitin recognition, the patterns by which these conformational changes influence the biological function of ubiquitin-partner interactions have not been identified, nor have the consequences of perturbing such motions been addressed.

In the case of ubiquitin, since the parent backbone conformations presumably represent a compromise for several binding partners with a wide variety of folds (e.g. —deubiquitinases, ligases, etc.), selection for sequences that accommodate a single partner could also identify high-affinity conformations not found in nature. Therefore, this study seeks in part, to determine if different DUBs take advantage of ubiquitin dynamics by recognizing unique substates of its conformational ensemble. Such a distinction would conceptually separate the ubiquitin hub from a single entity into a set of related but conformationally unique binding partners.

Materials and Methods

Deubiquitinase Expression and Purification

DNA encoding deubiquitinase constructs were cloned into a pET derivative vector with a TEV-cleavable N-terminal 6×His tag (SEQ ID NO: 2) and a C-terminal Avi tag and expressed in *E. coli* as biotinylated proteins by co-expression with a BirA-containing expression plasmid. Biotinylation was confirmed by mass spectrometry. Biotinylated catalytic domain constructs were USP7 residues 208-554, USP14 residues 91-494, and UCHL5 residues 1-228. UCHL1 and UCHL3 were purified as full-length proteins. Catalytic site mutations were USP7 C223A, USP14 C114A, UCHL1

C90A, UCHL3 C95A, and UCHL5 C88A. After expression, proteins were purified to homogeneity by passage over a Ni-NTA column, cleavage of the His tag with TEV protease, repassage over the nickel column, and purification on an S-200 or S-75 gel filtration column (GE Life Sciences). For enzymatic assays, unbiotinylated USP2 catalytic domain, USP5, USP10, USP47, and USP7 were obtained from Boston Biochem.

Ubiquitin Variant Expression and Purification

DNA encoding ubiquitin variants were cloned into a pET derivative vector with an N-terminal 6×His tag (SEQ ID NO: 2) and expressed in E. coli. as previously described.[45] The proteins were purified by Ni-NTA affinity chromatography followed by S75 size exclusion chromatography.

Display of Ubiquitin on M13 Phage

Ubiquitin was displayed on the surface of M13 bacteriophage by modifying a previously described phagemid pS2202b. Standard molecular biology techniques were used to replace the fragment of pS2202b encoding Erbin PDZ domain with a DNA fragment encoding for ubiquitin. The resulting phagemid p8Ub contained an open reading frame that encoded for the maltose binding protein secretion signal, followed by gD tag and Ubiquitin and ending with the major coat protein p8. E. coli harboring p8Ub were co-infected with M13-KO7 helper phage and were amplified following the standard protocol.[2] The propagated phage was purified according to the standard protocol and re-suspended in 1 ml PBT buffer (PBS, 0.5% BSA and 0.1% Tween 20), resulting in the production of phage particles that encapsulated p8Ub DNA and displayed Ubiquitin. The display level was analyzed using a phage ELISA as following: 2 μg/ml anti-gD antibody were immobilized on the Maxisorp immunoplate and blocked, 1:3 serial dilution of gD-Ubiquitin-displaying phage were applied to the wells. The plate was washed and the bound phage were detected by anti-M13-HRP followed by TMB substrate.

Library Construction and Sorting

Ubiquitin libraries were constructed using the Kunkel mutagenesis method. Residues T7, L8, I13, E34, I36, L69 and L71 were randomized with the NNK codon. A stop template (single strand DNA of p8Ub containing three stop codons in the regions of T7-I13, E34-I36 and L69-L71) was used to construct a library that contained ~5×10$^{10}$ unique members. The library was cycled through rounds of binding selection in solution against the C-terminally monobiotinylated catalytic domain of USP7 (residues 208-554) with a C223A mutation (designated as USP7catC223A). For round one, 20 μg of biotinylated USP7catC223A was incubated with 1 ml of phage library (~1×10$^{13}$ pfu/ml) at 4° C. for 2 h and captured for 15 min at room temperature by 200 μl of Dynabeads® MyOne Streptavidin that has been previously blocked with blocking buffer (PBS, 1% BSA). The supernatant was discarded and the beads were washed three times with PBS, 0.1% Tween20. The bound phage was eluted with 400 μl 0.1 M HCl for 7 min and immediately neutralized with 60 μl of 1 M Tris, pH 13. The eluted phage was amplified as described by Tonikian et al. 2007[2] For round two, the protocol was the same as round one except for using 10 μg biotinylated USP7catC223A and 100 μl of Dynabeads. For round three and round five, 2 μg biotinylated USP7catC223A was incubated with the amplified phage from the previous round and the phage-USP7catC223A complex was captured by NeutrAvidin-coated plates previously treated with blocking buffer. Round four was identical to round three except for using Strepavidin-coated plates to capture biotin-USP7catC223A-phage complex. Phage was propagated in E. coli XL1-blue with M13-KO7 helper phage at 30° C. following the standard protocol.[46]

Results

Figure 2:
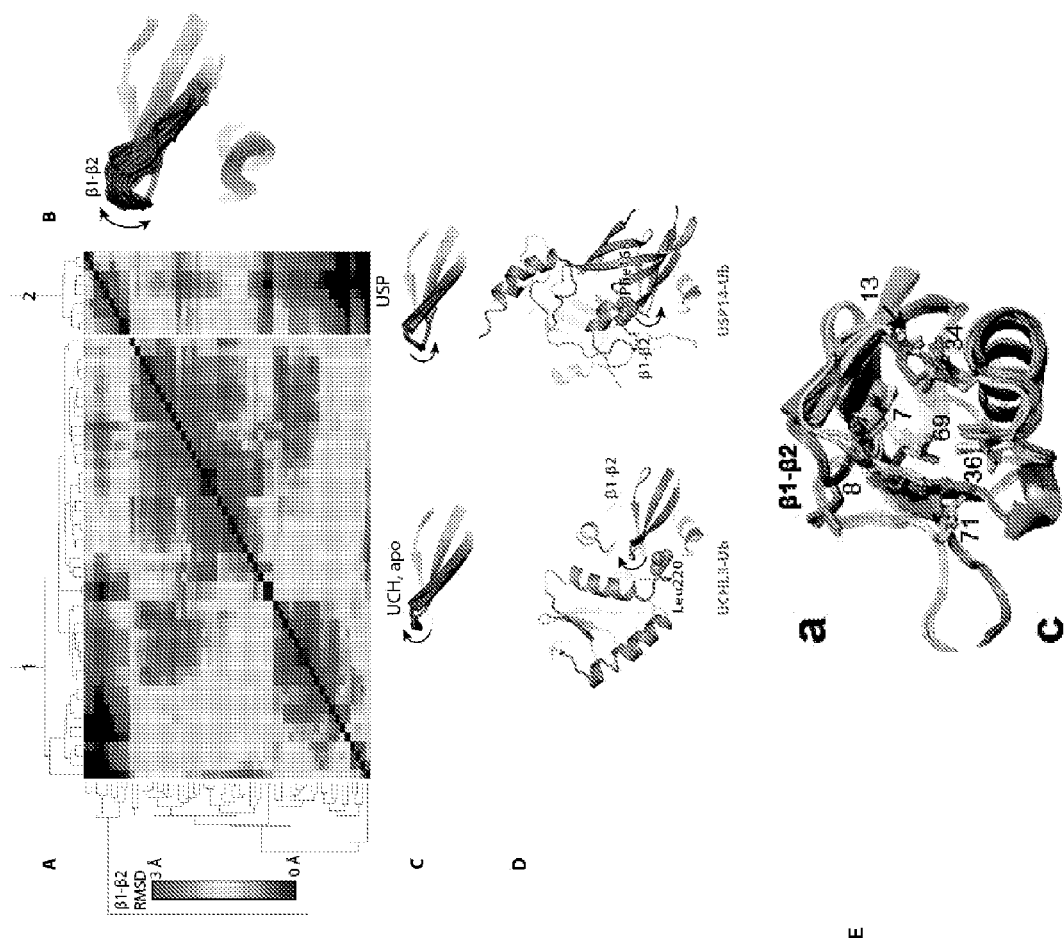
FIG. 2 depicts a cluster root mean squared deviation (RMSD) analysis of the β1/β2 region of ubiquitin within protein complexes which reveals two distinct conformations that influence DUB binding. A) Clustered heat map of the RMSD of ubiquitin's β1/β2 region (residues 6-10) in all high-resolution structures of ubiquitin complexes after pairwise alignment of the remainder of the globular core (residues 1-5 and 11-70). B) Without inspection of the clustered RMSD, the conformations adopted by the β1-β2 region appear as a smear of possible conformers. C) Comparison of the "up" and "down" β1/β2 conformers. D) UCH-type DUBs bind to the "up" conformation of β1/β2 (UCHL3-Ub complex PDB code 1xd3) while USP-type DUBs bind the "down" state (USP14-Ub complex PDB code 2ayo). Ubiquitin is depicted in red, DUBs are shown in blue. A DUB residue packing against β1/β2 thereby restricting its conformation (UCHL3-Leu220, USP14-Phe168) is shown as a sphere. E) Overlay of three ubiquitin structures solved in complex with UCHs (lavender, PDB codes 1cmx, 1xd3 and 3ifw) and USPs (pink, PDB codes 2ayo, 2hd5 and 2ibi). The sidechains of residues allowed to mutate in the phage library are shown.
Figure 30:
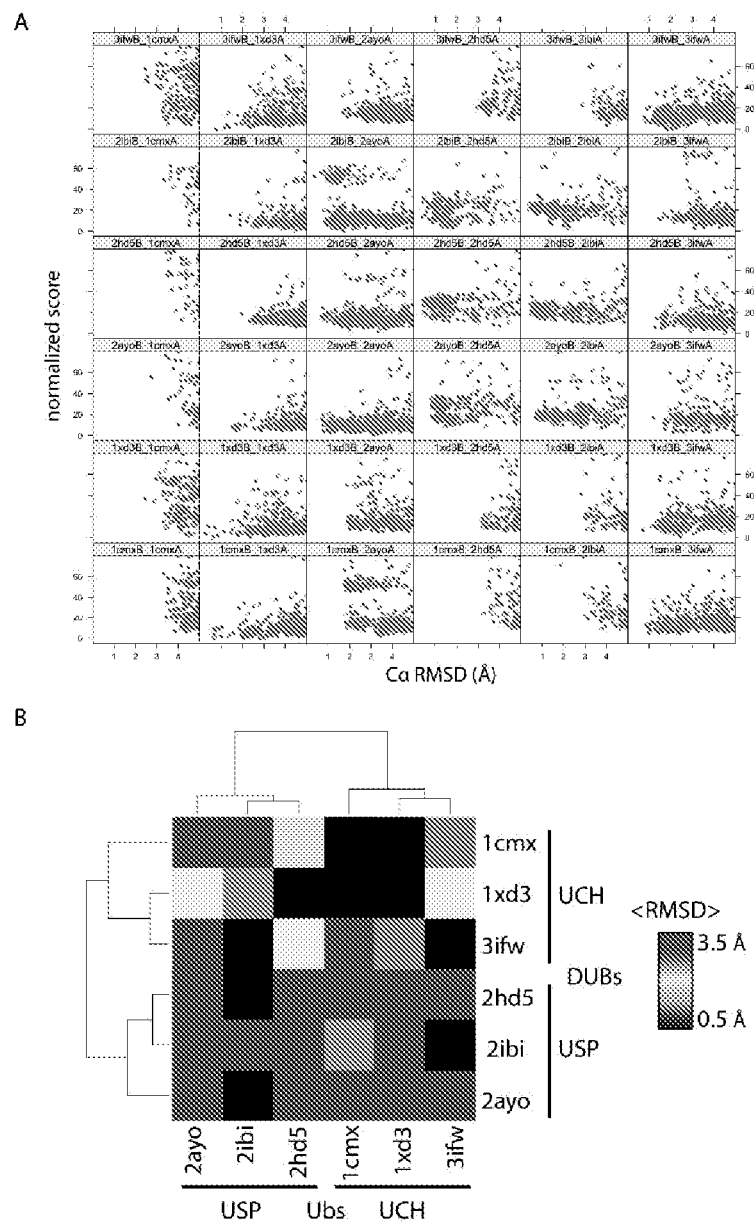
FIG. 30 depicts Cross-docking indicates that ubiquitin state can differentiate USP- and UCH-type deubiquitinases. A) Score-vs-Cα plots for each ubiquitin-deubiquitinase combination, with the PDB code of each model listed above each plot. The ubiquitin moiety is listed first (<PDB code>B) and the deubiquitinase is second (<PDB code>A). For example, 2ibiB_2ayoA is the ubiquitin from 2ibi (USP2-bound Ub) docked onto the deubiquitinase from 2ayo (USP14), whereas 1xd3B_2ayoA is the ubiquitin from 1xd3 (UCHL3-bound Ub) docked onto the deubiquitinase from 2ayo (USP14). Structures were prepared and docked as described in the Methods, excluding the C-terminal tail of ubiquitin to avoid crystallographic bias. B) Summary of cross-docking results in panel A. The lowest five RMSDs from each cross-docking experiment were averaged and are presented as clustered heatmap. Note that all ubiquitins from USP-bound ubiquitins are more readily cross-docked onto USP-type DUBs (lower RMSD), and UCH-bound ubiquitins are more readily docked onto UCH-type DUBs, but cross-family docking is generally unsuccessful.

Since all DUBs bind to the β1/β2 region of ubiquitin but are separable into several structural families, it was hypothesized that some types of DUBs might recognize distinct conformational states of ubiquitin. To address this question, pairwise alignments of all 56 available high-resolution crystal structures of ubiquitin in complex was performed with at least one partner and the results clustered based on the root means square deviation (RMSD) of β1/β2. Cluster analysis separates the apparent "smear" of β1-β2 loop conformations (FIG. 2A) into conformational families, with subtle intra-family differences (FIG. 2B). These atomic "snapshots" imply that ubiquitin's β1-β2 loop accesses a series of substates, with modest energy barriers between each substate, in accordance with fast transitions between substates.[28] The largest cluster (Cluster 1) represents an "up" conformation of the β1/β2 region and contains all ubiquitin structures in complex with UCH-type DUBs, indicating that UCHs bind the "up" conformation (FIG. 2C-D). By contrast, Cluster 2 represents a "down" β1/β2 conformation and contains every USP-type DUB-ubiquitin complex crystallized to date. Notably, UCH-type DUBs typically bind ubiquitin with nanomolar affinities and the UCH-binding state also clusters with apo ubiquitin, suggesting that the "up" state may predominate in solution. Conversely, USP-type DUBs typically have high micromolar affinities for ubiquitin and the USP-binding state is both unobserved in crystal structures of apo ubiquitin and only detectable by NMR measurables sensitive to motion over the nanosecond to microsecond timescale.[28] Thus, the "down" state may be only weakly populated in solution. Comparison of the "up" and "down" conformations reveals markedly distinct packing of each state, with long-range effects transmitted from β1-β2 to the C-terminus in a manner that may also influence binding to the DUBs. For example, the "down" conformation projects Leu8 towards Leu71, pushing the C-terminus as a lever arm towards a conformation that positions it to interact with the active site of USP-type DUBs (FIG. 2E). Computational docking also indicates binding of a DUB to either the "up" or "down" ubiquitin conformer is mutually exclusive: the UCH-family enzymes are disposed to bind the "up" state, while USP family deubiquitinases bind the "down" state (FIG. 30).

Figure 3:
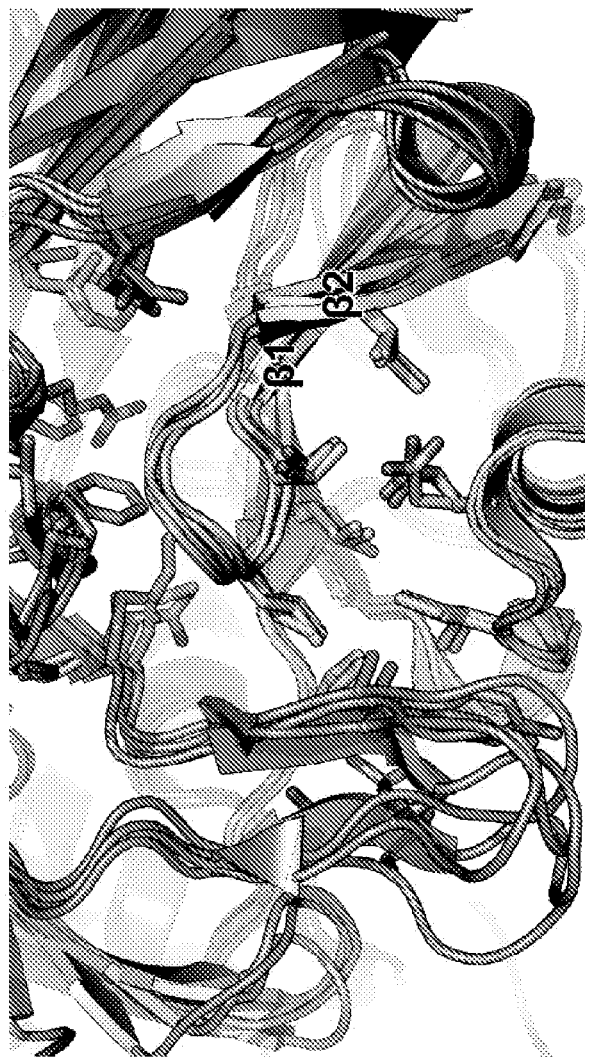
FIG. 3 depicts USP-type deubiquitinases (blue) contacting the β1-β2 loop region of ubiquitin (orange) using variable surface chemistries. Deubiquitinase residues in contact with ubiquitin and ubiquitin residues allowed to vary during Conformational Display are shown as sticks. Deubiquitinases shown are USP7 (PDB code1NBF), USP14 (PDB code 2AYO), USP2 (PDB code 2IBI), and USP21 (PDB code 3I3T).

To stabilize ubiquitin in a desired conformation, full-length human ubiquitin was displayed on the major (p8) or minor (p3) coat proteins of M13 phage with a gD tag fused to its N-terminus. The display levels on both coat proteins are similar as indicated by the detection of gD tag on the phage surface (data not shown). Since protein cores are extensive and cooperative, effective Conformational Display assumes a knowledge of which positions contribute to motion within the region of interest. Hence, computational protein design was used to identify buried amino acid positions within ubiquitin that appear non-optimal for adopting a USP-binding state and contact variable surfaces among different USPs (FIG. 3). The resulting seven positions (Thr7, Leu8, Ile13, Glu34, Ile36, Leu69, and Leu71) were randomized in p8 or p3-displayed ubiquitin libraries and selected against a catalytically inactive mutant of the catalytic domain of USP7.

A total of 69 unique sequences were identified from the p8-displayed ubiquitin library. Approximately 90% of these clones contain cysteine at both position 7 and 69, with some substituting Cys8 for Cys7 (FIG. 1B). Since positions 7/8 and 69 are apposed in the tertiary structure of ubiquitin, this immediately suggested the presence of a disulfide that stabilizes a USP7-binding conformation. Only 7 unique clones lacked the dicysteine motif, and are henceforth designated as "non-disulfide" binders (FIG. 1B). Both disulfide and non-disulfide binders exhibit several significant sequence changes compared to wildtype ubiquitin. A basic residue (mostly Arg with a few Lys) is highly conserved at position 71 in all clones; position 34 was exclusively changed to hydrophobic residues (Ile, Leu or Val) from Glu in wildtype; and position 36 was primarily aromatic (Tyr and Phe) in disulfide-bonded clones. For disulfide-containing binders, position 13 preferred polar residues (Arg, His, Ser, Lys, and Asn), whereas non-disulfide clones preferred a tyrosine.

To test the specificity of the USP7-selected conformational binders, designated as "U7UbXX" (where XX is the clone number), 24 phage-displayed clones were tested against a panel of DUBs in phage spot ELISA. As shown in FIG. 1C, all of these clones bind specifically to USP7 with no detectable binding signal to USP14, UCHL1, UCHL3 and UCHL5.

TABLE 8

Equilibrium dissociation constants (nM) of U7Ub variants for deubiquitinases.

|  | USP7[§] | USP14[§] | UCHL1 | UCHL3 |
| --- | --- | --- | --- | --- |
| Wildtype | ND | ND | 385[21] | 500[22] |
| U7Ub7 | 200 ± 22 | ND | ND | ND |
| U7Ub25 | 86 ± 2 | ND | ND | ND |
| U7Ub25.2540 | 36 ± 2 | ND | ND | ND |

[§]catalytic domain, active site mutant;
ND = not detectable

Figure 4:
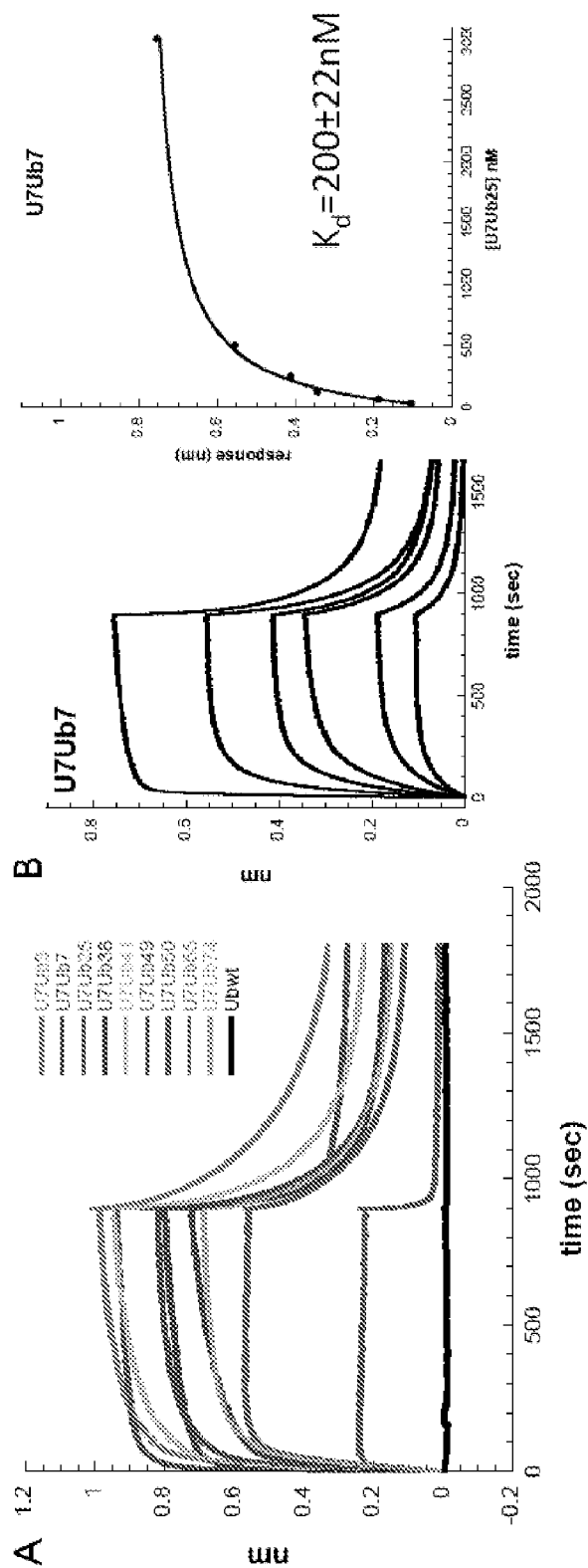
FIG. 4 depicts A) Screening of U7Ub variants by biolayer interferometry. Equal amounts of USP7 catalytic domain active site mutant (USP7catC223A) was coupled to each sensor tip and immersed in a constant concentration of each U7Ub. Variants were chosen based on steady state response and apparent on and off rates. B) Titration of the U7Ub7 variant against USP7catC223A indicates a dissociation constant of approximately 200 nM.

To quantitate the binding of the U7Ub variants as purified proteins, eight clones were transferred to an N-terminally His-tagged pET expression vector. After expression and purification to homogeneity, relative affinities via biolayer interferometry were determined by measuring steady state response at a single concentration of ubiquitin variant (FIG. 4A). Follow-up biolayer interferometry titrations revealed that two of the tightest binders, U7Ub7 (disulfide) and U7Ub25 (non-disulfide), have affinities for the catalytic core of USP7 of less than 200 nM (Tables 8 and 9; FIG. 4B). Isothermal titration calorimetry confirmed that U7Ub25 tightly binds the catalytic core of USP7 in a 1:1 complex (FIG. 1C) and with an affinity of approximately 190 nM. Notably, the association of wildtype ubiquitin with USP7 is nearly undetectable at concentrations up to 200 μM (data not shown[10]), revealing that these initially-selected ubiquitin variants have affinity improvements of more than 1,000-fold.

TABLE 9

Dissociation constants of ubiquitin variants for USP7catC223A, obtained from steady state and kinetic fitting of biolayer interferometry data.

|  | U7Ub7 | U7Ub25 | U7Ub25.2540 |
| --- | --- | --- | --- |
| $K_d$(steady state) nM | 200 ± 22 | 86 ± 2 | 36 ± 2 |
| $K_{on}$ (1/Ms) E+04 | 1.80 ± 0.95 | 7.32 ± 0.78 | 12.5 ± 2.2 |
| $K_{off}$(1/s) E−03 | 7.01 ± 0.56 | 8.83 ± 0.81 | 5.48 ± 0.79 |
| $K_d$(kinetic) nM | 353 ± 16 | 121 ± 1 | 44 ± 2 |

This Example validates the novel technique of Conformational Display and identifies conformationally stabilized variants of the conformationally heterologous ubiquitin protein that is not otherwise found in nature. Additionally, this novel stabilized ubiquitin protein binds to the deubiquitinase USP7 with a thousand-fold greater affinity versus wildtype ubiquitin.

Example 2

Surface Maturation of Conformationally Stabilized Ubiquitin Proteins

Since the conformationally-designed library does not focus on residues at the surface of wildtype ubiquitin, it was reasoned that doing so might further improve affinity for USP7. This example therefore demonstrates that surface maturation can be used to further enhance the binding of a conformationally stabilized protein to a substrate.

Materials and Methods

Affinity maturation of U7Ub25

The affinity maturation library was constructed using the Kunkel mutagenesis method. Surface residues Q2, F4, T14, Q40, R42, A46, G47, Q49, Q62, E64, S65, T66, H68, V70 and R72 were "soft randomized" using a doping codon in which each base position was a mixture of 70% wildtype base and 10% of the other three bases that would result in ~50% mutation rate at amino acid level. A stop template (single strand DNA of p8U7Ub25 containing three stop codons in the regions of 7-13, 34-36 and 69-71) was used to construct a library that contained ~4×10[10] unique members. The library was cycled against USP7catC223A for 5 rounds as described above, except for round 3-5, lowered USP7catC223A concentration were used, which is 10, 5 and 2 nM, respectively.

Spot Phage ELISA

After five rounds of binding selection, individual phage clones were picked and inoculated into 450 μl 2YT media containing 50 μg/ml carbenecillin and M13-KO7 helper phage in 96-well blocks, which were grown at 37° C. overnight. The supernatant was analyzed with spot phage ELISA as follows: biotinylated USP7catC223A, USP14 catalytic domain (C114A), UCHL1, UCHL3, or UCHL5 catalytic domain were captured to NeutrAvidin-coated 384-well Maxisorp immunoplates and phage supernatant diluted (1:3) with PBT buffer was added to the wells. The plates were washed and bound phage was detected with anti-M13-HRP followed by TMB substrate. In these assays, phage binding to NeutrAvidin alone was tested in parallel to assess background binding. Clones whose binding signals for USP7catC223A were more than 5 times higher than to NeutrAvidin (background) were considered positive. Positive clones were subjected to DNA sequence analysis.

Isothermal Titration Calorimetry

U7Ub25 and USP7catC223A were dialyzed overnight into 50 mM HEPES pH 7.5 and 150 mM NaCl and titrated on a MicroCal ITC200. The concentration of U7Ub25 in the cell was 200 μM and the concentration of USP7catC223A in the syringe was 20 μM. Experiments were performed with a 0.2 μL initial injection, discarded during data analysis, followed by twenty 2 uL injections spaced 250 s apart. The cell stirred at 1000 rpm at 25° C. Binding curves were fit to a one-site binding model in Microcal Origin.

Binding Assay by ELISA

Biotinylated USP7catC223A was captured on NeutrAvidin coated Maxisorp® Plate that was previously blocked by Blocking Buffer and was incubated with 1:3 serial dilution of His-tagged Ubiquitin variants at concentration range of 0-20 μM for 1 hour at 4° C. in PBT buffer. The plate was then washed with PT buffer and the bound His-tagged proteins were detected by anti-PentaHis-HRP conjugate ('PentaHis' disclosed as SEQ ID NO: 13) (Qiagen, Cat. No. 34460, Germantown, Md.) followed by TMB substrate.

Affinity Measurement by Biolayer Interferometry

The binding affinities of Ubiquitin variants to USP7catC223A were measured by biolayer interferometry on an OctetRed 384 (Fortebio, Menlo Park, Calif.). Strepavidin biosensors (Fortebio, Cat. No. 18-5020) were loaded with biotinylated USP7catC223A in PBS buffer containing 0.05% Tween20 and 0.1% BSA, washed in the same buffer and transferred to wells containing ubiquitin variants at concentrations ranging from 0-2 µM in the same buffer. The dissociation constant was obtained by non-linear fitting of the responses to a steady state algorithm using Octet software. Similar affinities were obtained by kinetic fitting.

Results

The highest affinity non-disulfide variant, U7Ub25, which may achieve high affinity and specificity through core repacking around β1-β2 was chosen for surface maturation. An affinity maturation library was designed by randomizing surface residues of U7Ub25 predicted to be involved in interaction of USP7 with ubiquitin (FIG. 5A), based on the crystal structure of wildtype ubiquitin in complex with USP7 (PDB code 1NBF[15]).

Figure 5:
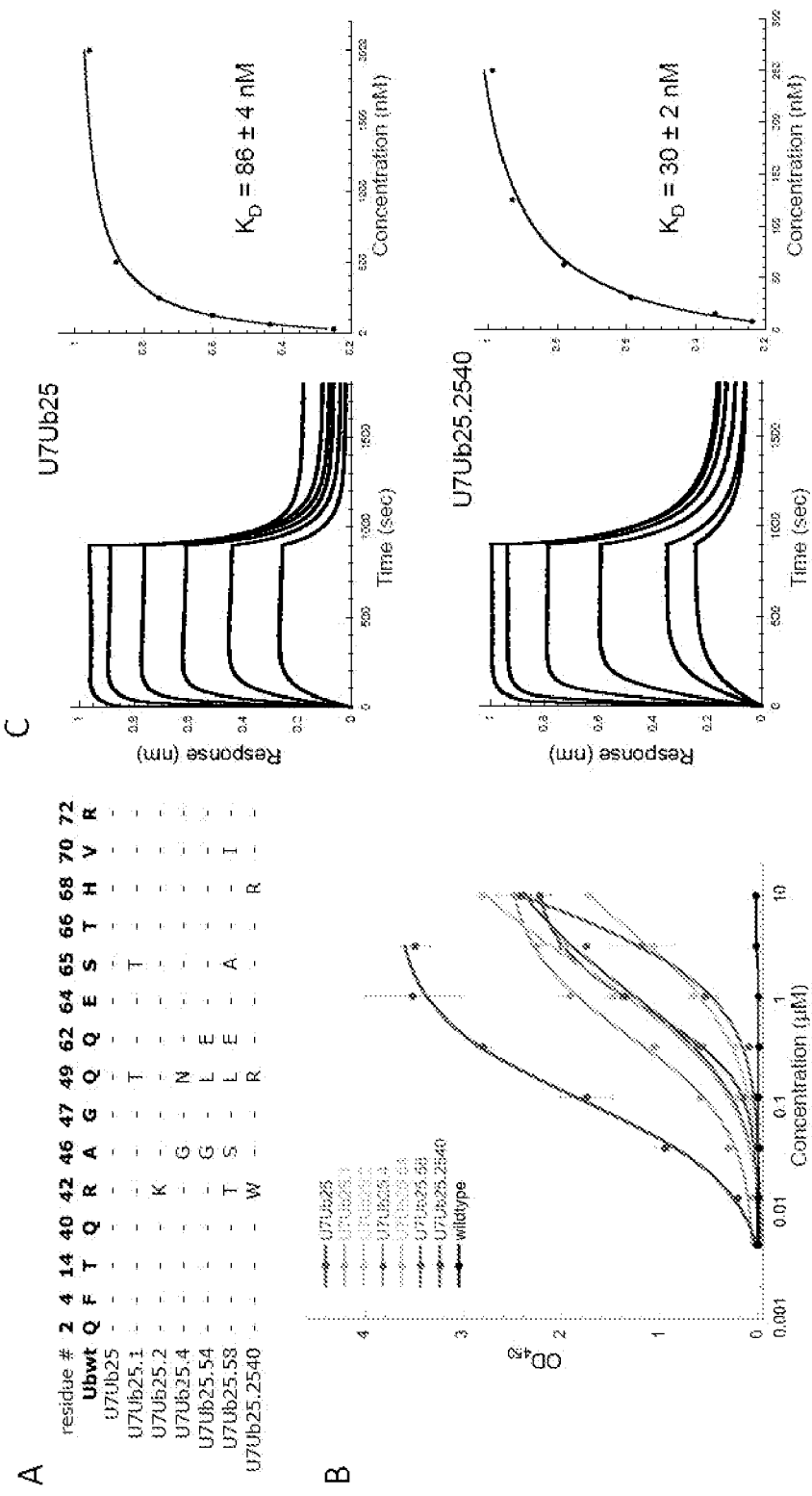
FIG. 5 depicts affinity maturation of the surface of a non-disulfide bond U7Ub further improves affinity for USP7. A) Sequences of affinity-matured cloned based on the U7Ub25 scaffold contain a small number of surface mutations. Ubwt (SEQ ID NO: 1) and mutant (SEQ ID NO: 20) sequences with specific residues as shown. B) Affinity-matured clone U7Ub25.2540 is the most potent binder of the USP7 catalytic domain in a protein ELISA assay. C) Biolayer interferometry indicates that U7Ub25 binds the catalytic domain of USP7 with a dissociation constant of 90 nM, while the affinity matured U7Ub25.2540 has a 3-fold enhanced affinity.

To isolate improved binders, the library was selected against decreasing concentrations of USP7. After 4 rounds of panning 6 unique clones that strongly bound USP7 were identified (FIG. 5A). All unique affinity matured clones were expressed and purified as His-tagged protein and their relative affinities were ranked by $EC_{50}$ as measured by ELISA. As shown in FIG. 5B, U7Ub25.2540 is the tightest USP7-binder and contains three mutations relative to U7Ub25: Gln42Trp, Gln49Arg, and His68Arg (FIG. 5A). The affinity of U7Ub25.2540 for the catalytic core of USP7, as measured by biolayer interferometry, is approximately 30 nM, representing a several-fold improvement relative to the U7Ub25 parent (FIG. 5C; Tables 8 and 9).

This Example illustrates that even further substrate binding affinity can be achieved for conformationally stabilized protein variants via surface maturation of amino acid residues that directly interact with residues on the surface of the substrate protein.

Example 3

Crystal Structures of Conformationally Stabilized Ubiquitin Proteins

In this example, the crystal structures of both U7Ub7 (disulfide) and U7Ub25.2540 (non-disulfide, affinity matured) were solved to understand how the mutations within the disulfide and non-disulfide classes of USP7-binding variants affect the structure of these molecules.

Materials and Methods

Crystallization and Data Collection

Cell pastes were resuspended into 25 mM Tris pH 8.0, 150 mM NaCl; reducing agent (0.5 mM TCEP) was added throughout the purification of U7Ub25.2540. Cells were purified on a Ni-chelating-affinity column and the tags were removed using a 6× his tagged (SEQ ID NO: 2) TEV protease overnight. Cleaved mixture was then further purified over a second Ni-chelating-affinity column and finally purified on a Superdex™75 (GE Healthcare) size exclusion column in 25 mM TRIS pH 8.0, 150 mM NaCl.

Diffraction quality crystals of U7Ub7 and U7Ub25.2540 were grown at 18° C. using the sitting and hanging drop vapor diffusion method by mixing 1 µl protein at 10 mg/ml in purification buffer and 1 µl crystallization solution containing 2.4 M $AmSO_4$ and 0.1M Citric acid pH 4.0. Crystals grew after 3 days and were transferred into a cryoprotectant solution containing 3.2 M $AmSO_4$ and 0.1M Citric acid pH 4.0. The crystals diffracted to 1.4 Å, and belong to spacegroup $P3_12$ with 4 molecules in the asymmetric unit. A single ubiquitin chain (PDB-ID 1UBQ) was used as a search model for molecular replacement.

NMR Spectroscopy

Samples were prepared for NMR spectroscopy with labeling performed according to the method of Cai et al.[47] with the modification that cells were spun down and transferred to M9 media containing U-$^2$H, $^{13}$C-D-glucose and ⅔ $^2H_2O$. Approximately 50% deuteration is required for the implementation of the µs $R_{ex}$ experiment.[48] NMR samples contained 10% $^2H_2O$ and 0.1 mM trimethylsilylpropionate. Deuterium incorporation was determined to be ca. 50% by mass spectrometry.

Resonance assignments for wild-type ubiquitin, U7Ub7 and U7Ub25 were obtained from semi-automated analysis of peak positions in $^1$H-$^{15}$N HSQC, HNCA, HNCACB and HNcoCA spectra using PINE.[49] Chemical shifts were referenced to trimethylsilylpropionate. Nearly complete backbone assignments were obtained for wild-type ubiquitin and the U7Ubs. The amide resonances of E24 and G53 are unobserved in all proteins. All NMR data sets were collected at 18.8 T on a Bruker DRX spectrometer or at 14.1 T on a Bruker Avance III spectrometer. Unless otherwise noted, NMR experiments were conducted at 24° C., calibrated to deuterated methanol.[50]

The {$^1$H}-$^{15}$N heteronuclear NOE values for wild-type ubiquitin and 7.7 were determined according to the method of Grzesiek and Bax.[51] The recycle delay in all experiments and $^1$H irradiation time were set to 5s and 1s, respectively. Microsecond $R_{ex}$ values were extracted from $H_z'N_z$, $H_zN_z'$, $H_z'N_z'$, and $H_zN_z$ $R_{1\rho}$ measurements where the prime denotes the presence of a spin-lock field during the relaxation delay.[48, 52] The spin lock fields employed were 10 kHz and 2 kHz on the $^1$H and $^{15}$N frequencies, respectively. Delay times were between 2 ms and 32 ms for all experiments with spin lock irradiation and 4 and 128 ms for $H_zN_z$, recorded in the absence of irradiation. Each of these experiments was recorded as a pseudo-3D with 64 complex $^{15}$N points in each plane and nine relaxation delay times recorded in an interleaved fashion to alleviate potential artifacts due to differential sample heating. Evolution curves were fit using nmrPipe[53] and data analysis was conducted according to Hansen et al.[52] $R_2$ dispersion data sets were collected according to the methodology of Tollinger et al.[54] with $R_{2obs}$ determined from 2-point fits in order to more fully sample the dispersion curve.[55] Data sets were collected as interleaved pseudo-3Ds with 64 complex $^{15}$N points in each plane and ca. 15 CPMG frequencies. CPMG frequencies sampled were between 50 and 950 Hz with two frequencies repeated for error analysis. $R_2$ dispersion curves were collected for 7.25 at 14.1 T and 6° C.

Results

Figure 6:
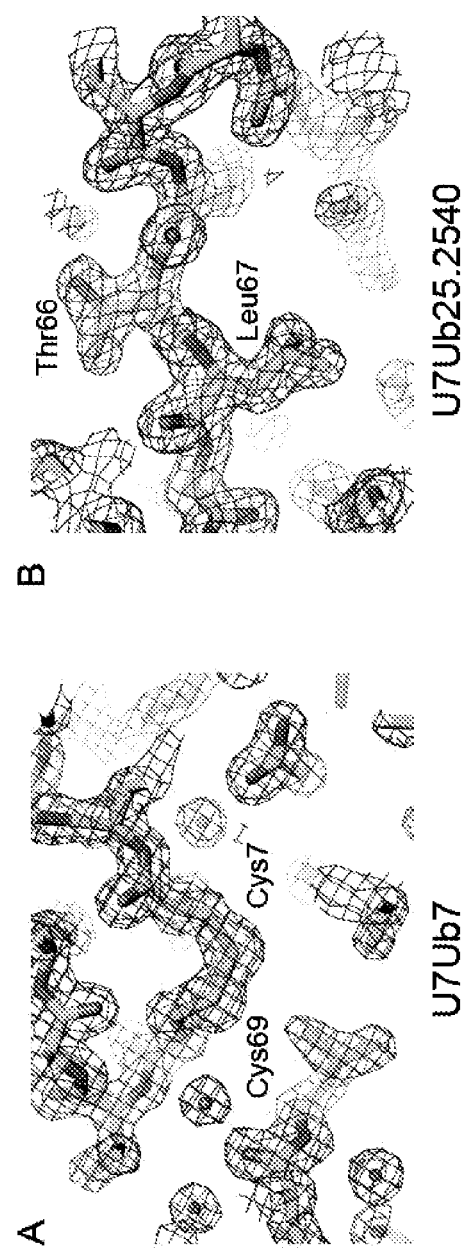
FIG. 6 depicts $2F_o\text{-}F_c$ electron density, contoured at $1\sigma$, for A) U7Ub7 and B) U7Ub25.2540. The final refined model is shown for reference.
Figure 7:
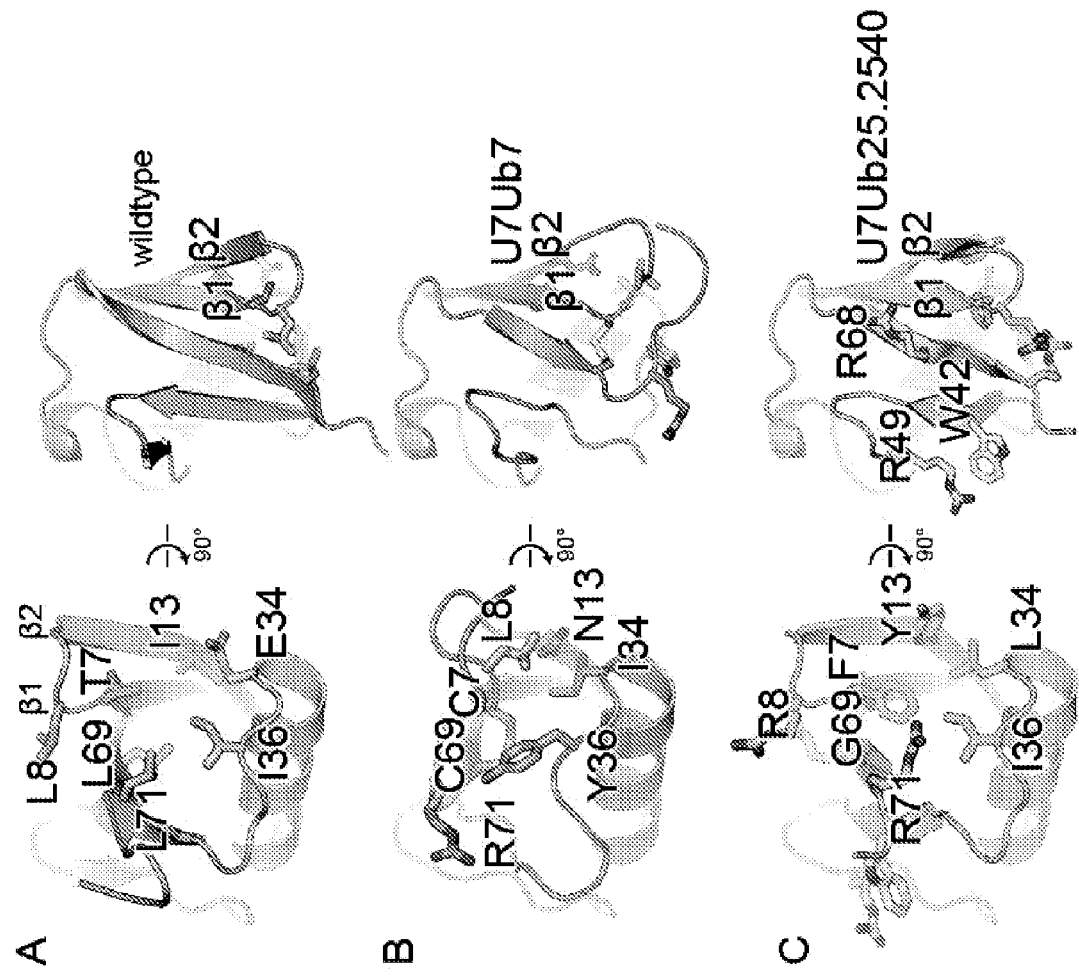
FIG. 7 depicts crystal structures of U7Ubs revealing altered backbone conformations or core packing. A) The structure of wildtype ubiquitin is shown for reference, with positions mutated in the originally selected variants shown as sticks and the β1-β2 region is labeled. B) The structure of U7Ub7 reveals a disulfide bond formed between positions 8 and 69, which distorts the conformation of the β1-β2 loop. C) The backbone conformation of the U7Ub25.2540 variant is almost identical to that of wildtype ubiquitin, but with altered packing around the β1-β2 region. Affinity-matured surface mutations are shown in yellow.
Figure 8:
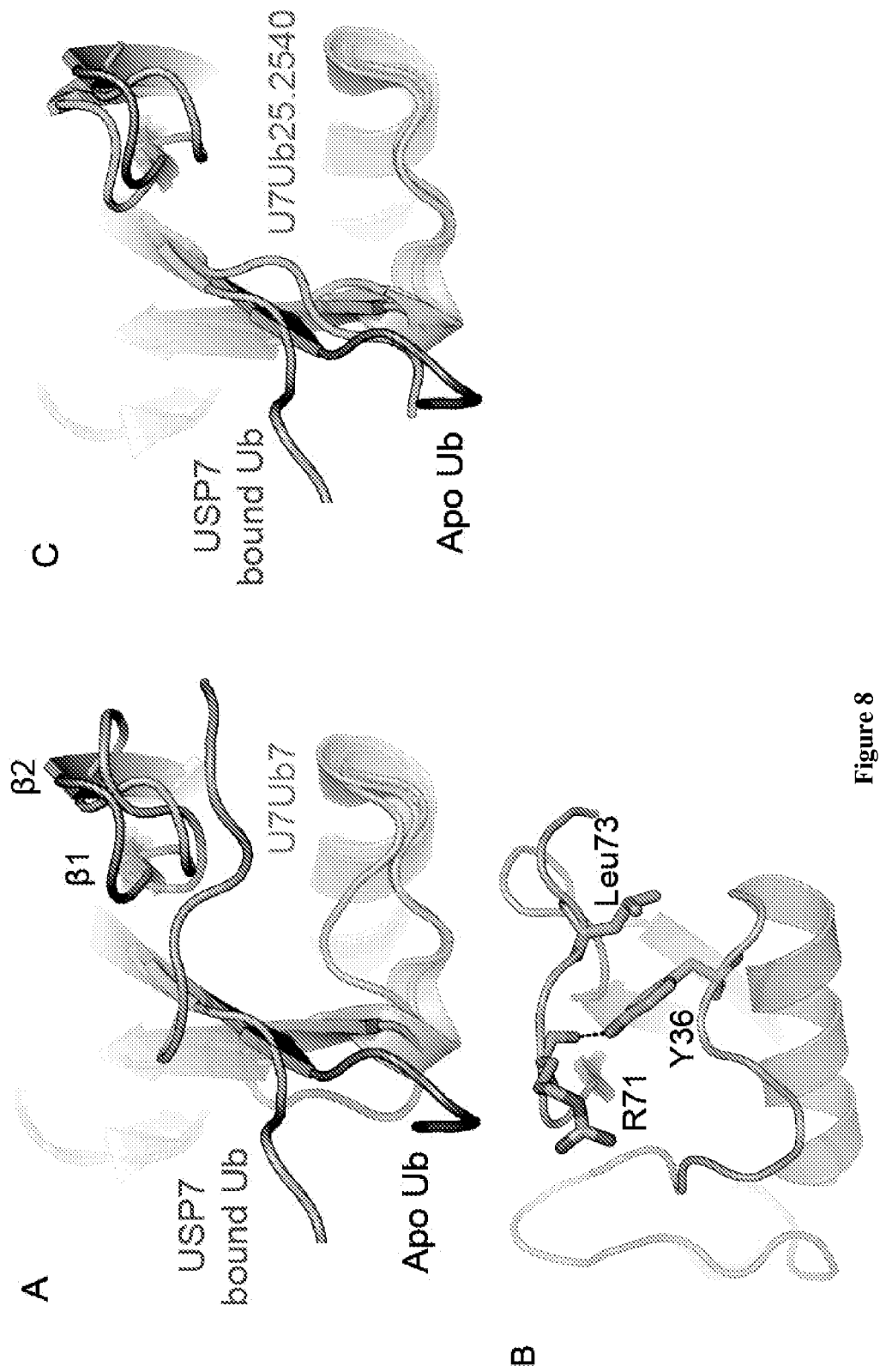
FIG. 8 depicts structural analysis of U7Ub variants. A) The β1-β2 loop of U7Ub7 is twisted downward, similar to that of USP7-bound ubiquitin and distinct from apo ubiquitin. B) Packing and hydrogen bonding interactions between the C-terminus of U7Ub7 and the rest of the protein. C) The conformation of U7Ub25.2540's β1-β2 loop is similar to that of apo ubiquitin.
Figure 9:
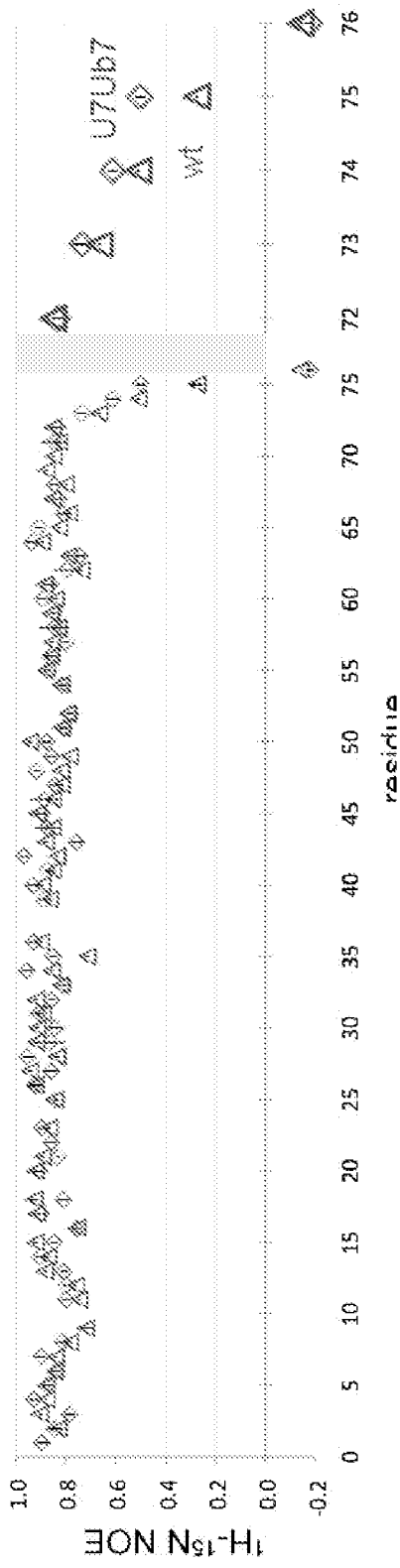
FIG. 9 depicts heteronuclear {$^1$H}-$^{15}$N NOE data showing that the C-terminus of Ub7.7 is mobile in solution, although restricted relative to wild-type.

As suspected from the strong preference towards cysteines at positions 7 and 69, The 1.8 Å structure of U7Ub7 reveals that these residues form a disulfide bond at the base of the β1-β2 loop (FIGS. 6-7; Table 10). The orientation of this disulfide twists β1-β2 downward relative to the apo wildtype conformation in a manner similar to that observed for wild-type ubiquitin bound to USP7 (FIG. 8A). Ile36Tyr also contributes to this twist by hydrogen bonding to the backbone of Arg71 and forming a stacking interaction with Leu73 (FIG. 8B). The Tyr36-Leu73 stack pushes the C-terminus of U7Ub7 so that it is oriented orthogonally to that of wildtype ubiquitin and forms backbone hydrogen bonds to the β1/β2 loop (FIG. 8A). However, heteronuclear NOE NMR measurements that probe fast timescale dynamics indicate the C-terminus of U7Ub7 is slightly less mobile than wildtype ubiquitin, but not completely restrained (FIG. 9). Hence, the unusual location of U7Ub7's C-terminus may not play a deciding role in its high affinity for USP7.

TABLE 10

Data collection and refinement statistics for U7Ub7 and U7Ub25.2540 crystals.

|  | UTUb25.2540 | U7Ub7 |
|---|---|---|
| PDB code | XYZ | XYZ |
| Resolution range (Å) | 28.08-1.4 | 37.92-1.784 |
| Space group | P3, 2 1 | P4, 2, 2 |
| Unit cell | 85.8 85.8 54.5 90 90 120 | 43.2 43.2 79.2 90 90 90 |
| Total reflections | 316470 | 95489 |
| Unique reflections | 45185 | 7483 |
| Multiplicity | 7.0 (3.5) | 12.8 (8.9) |
| Completeness (%) | 98.7 (88.0) | 97.7 (69.2) |
| I/sigma(I) | 34.9 (3.9) | 22.7 (6.7) |
| Wilson B-factor | 13.30 | 12.49 |
| R-sym | 0.031 (0.319) | 0.098 (0.338) |
| R-factor | 0.1966 | 0.1835 |
| R-free | 0.2364 | 0.2175 |
| Number of atoms | 2696 | 702 |
| Protein residues | 299 | 77 |
| Water molecules | 250 | 88 |
| RMS(bonds) | 0.029 | 0.016 |
| RMS(angles) | 1.92 | 1.43 |
| Ramachandran favored (%) | 100 | 100 |
| Ramachandran outliers (%) | 0 | 0 |
| Average B-factor | 19.10 | 12.12 |

Statistics for the highest-resolution shell are shown in parentheses.

Figure 10:
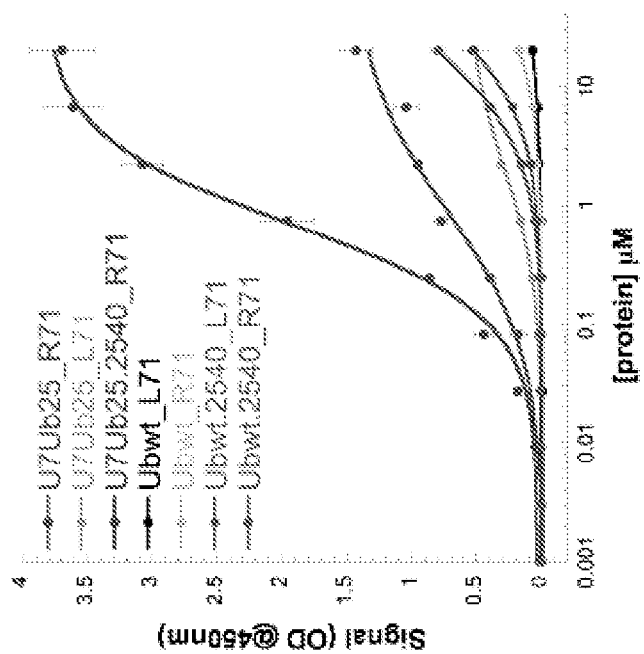
FIG. 10 depicts both core-repacking and solvent-exposed mutations are necessary for U7Ub25 to achieve high affinity. Although reverting the Leu71Arg mutation to its wildtype identity in the context of the U7Ub25 core (U7Ub25_L71 and U7Ub25.2540_L71) strongly decreases affinity, introducing Arg71 into wildtype ubiquitin (Ubwt_R71) is insufficient for tight binding. Similarly, a wildtype ubiquitin core with all combinations of surface mutations has compromised binding to USP7 (Ubwt_R71, Ubwt.2540_L71, Ubwt.2540_R71). Combining the repacked core with the wildtype ubiquitin surface (U7Ub25_L71) is also insufficient for tight binding. Hence, both the newly selected core and rearranged surface are required for high affinity binding (U7Ub25_R71, U7Ub25.2540_R71).
Figure 11:
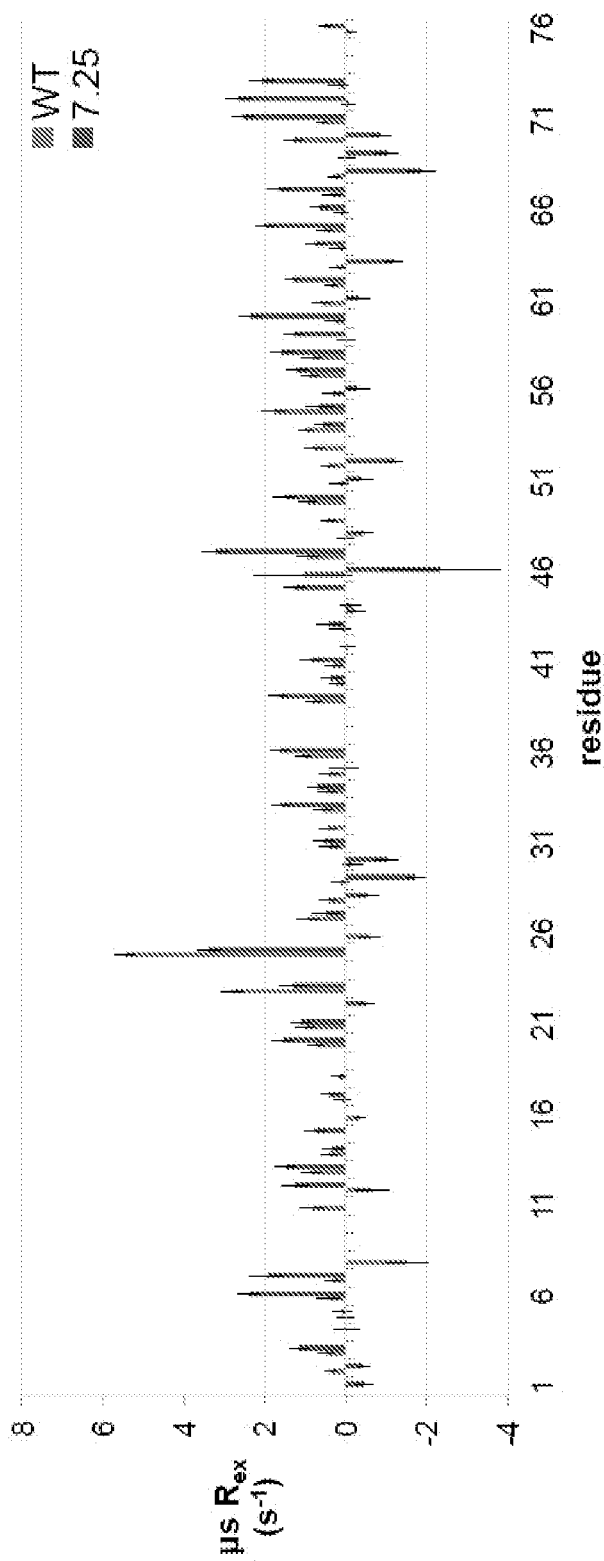
FIG. 11 depicts U7Ub25 possesses microsecond motions similar to wild-type ubiquitin. U7Ub25 has no detectable motions on the millisecond timescale as the $R_2$ values determined for U7Ub25 show no dependence on the frequency of CPMG refocusing pulses (data not shown).

By contrast to U7Ub7, the 1.3 Å resolution structure of U7Ub25.2540 indicates that its backbone is nearly identical to apo wildtype ubiquitin (FIGS. 8C and 10). The core mutated residues (Thr7Phe, Leu8Arg, Ile13Tyr, Glu34Leu, Leu69Gly, and Leu71Arg) are tightly packed, but in a manner distinct from wildtype (FIG. 7A, C). The mutations introduced by affinity maturation (Arg42Trp, Gln49Arg, and His68Arg) all cluster on the USP7-contacting sheet of the variant and form a continuous interaction surface. Since the backbone structure of U7Ub25.2540 is so similar to that of wildtype ubiquitin, relaxation dispersion measurements were used to determine whether apo state dynamics had been perturbed, but found no significant differences compared to wildtype ubiquitin (FIG. 11).

This example demonstrates that, while the conformationally stabilized U7Ub25 and U7Ub25.2540 ubiquitin proteins have significantly increased affinity for USP7 and markedly different packing around the β1-β2 element, their backbone are minimally affected versus as compared to wildtype ubiquitin.

Example 4

Core and Surface Mutations in U7Ub25 Cooperate for Affinity Towards USP7

This example evaluates whether the alternative packing around β1-β2 observed for the non-disulfide conformationally stabilized ubiquitin clones determine affinity.
Results The binding of reversion and addition mutants in the context of U7Ub25 and wildtype ubiquitin was initially measured (FIG. 10). Since the U7Ub variants contain concerted buried changes within a local region of tertiary structure, single reversion would be expected to produce clashes and yield poorly folded proteins. An exception is the Leu71Arg mutation, which is shared amongst almost all U7Ub2 (FIG. 1B), and which is solvent-exposed and relatively independent of the new packing around β1-β2 (FIG. 7B-C). Hence, the buried non-native core was added or subtracted as one mutational unit, as well as changed position 71 to the selected Arg or wildtype Leu. The importance of the affinity-matured surface residues found in U7Ub25.2540 was also investigated. In the following descriptions, the clone name indicates the identity of the core mutations, surface changes if any are indicated after a dot, and the identity of the residue at position 71 is preceded by an underscore. For example, Ubwt.2540_L71 indicates a mutant with a wildtype ubiquitin core, the affinity matured surface mutations found in U7Ub25.2540, and a leucine (wildtype identity) at position 71.

In the context of the newly packed core, Arg71 is critical for binding to USP7 (FIG. 10, U7Ub25_R71 vs U7Ub25_L71). However, the Arg71 mutation on its own, paired with ubiquitin's wildtype core, is insufficient for tight binding (Ubwt_L71 vs Ubwt_R71). Therefore, it appears that the packing engendered by buried mutations around β1-β2 is critical for proper positioning of Arg71. Similarly, the multiple mutations across the affinity-matured surface do impart some affinity in the context of the wildtype core (FIG. 10, Ubwt_L71 vs Ubwt.2540_L71), but these changes are most effective in the presence of both the accompanying repacked core and Arg71 (FIG. 10, Ubwt.2540_L71 vs U7Ub25.2540_R71). Notably, a mutant carrying every mutation except for the repacked core is strongly compromised in its binding to USP7 (FIG. 10, Ubwt.2540_R71 vs U7Ub25.2540_R71).

In sum, this example shows that the buried and surface mutations found in U7Ub25 and U7Ub25.2540 inextricably cooperate to yield their potent increase in affinity for USP7.

Example 5

U7Ub Conformationally Stabilized Ubiquitin Variants Inhibit USP7 Catalytic Activity This example determines whether binding of U7Ub25 and U7Ub25.2540 to USP7 is inhibitory with respect to USP7's proteolytic deubiquitinase enzymatic activity.
Materials and Methods Ubiquitin variants at a concentration range of 0-20 µM were mixed with 250 nM Ubiquitin-AMC (Boston Biochem, Boston, Mass., Cat. No. U-550). A panel of DUBs at 2, 5, 3 and 5 nM for USP7, USP47, USP2 and USP5, respectively, in PBS buffer containing 0.05% Tween20, 0.1% BSA and 1 mM DTT for 30 minutes were added to the Ubiquitin-AMC/Ubiquitin variants mixture and the initial velocity was immediately measured by monitoring fluorescence excited at 340 nm and emission at 465 nm using SpectraMax®M5e (Molecular Device, Sunnyvale, Calif.). The initial rates were calculated based on slopes of increasing fluorescence signal. Enzyme activity was also measured as end point fluorescence intensity for USP10 and full length USP7, in which increasing concentration of ubiquitin variants were incubated with 20 nM USP10 or 1.7 nM USP7 and 2 µM Ubiquitin-AMC for 1 hour, then the fluorescence intensity were measured. In both cases, the velocity were normalized to percentage of the maximum rate (when concentration of inhibitor is zero) and the data was processed using KaleidaGraph by fitting to the following equation:

$$v = v_0 + \frac{v_{max} - v_0}{1 + \left(\frac{I}{IC_{50}}\right)^n},$$

in which v is the percentage of maximum rate; I is the concentration of inhibitor (Ubiquitin variants); $v_0$ and $v_{max}$ are minimum and maximum percentage of the rate, respectively.

Results

Figure 12:
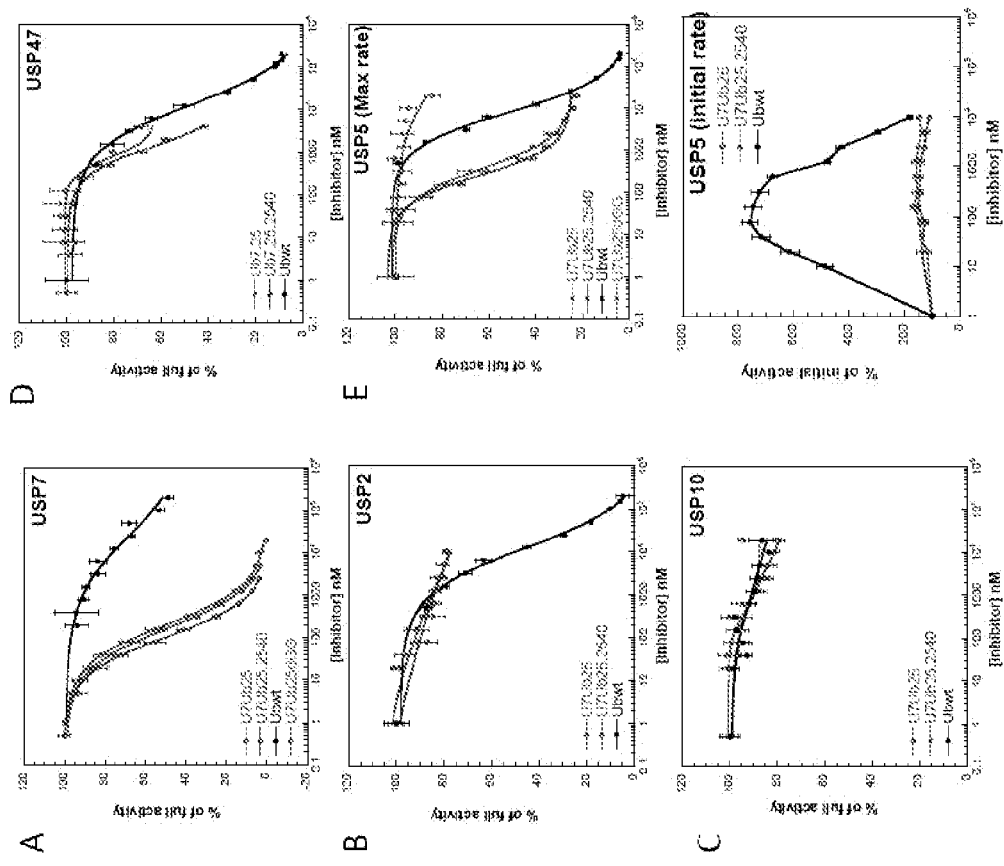
FIG. 12 depict that enzymatic assays reveal U7Ub25 and U7Ub25.250 are potent inhibitors of full-length USP7. A) Both U7Ub25 and U7Ub25.2540 strongly inhibit full-length USP7 ($IC_{50}$ 172 nM and 104 nM, respectively). Deletion of the C-terminal diglycine motif (U7Ub25dGG) has no effect upon inhibitory potential. B) The U7Ubs do not inhibit the highly active USP2 catalytic domain. C) USP10, whose cellular function directly opposes that of USP7, is not inhibited by the U7Ubs. D) Although USP47 is the most closely related deubiquitinase to USP7, the U7Ubs are much less potent inhibitors of this DUB than USP7 ($IC_{50}$~10 μM). E) Top: The U7Ubs inhibit full-length USP5, with $IC_{50}$s of 373 nM (U7Ub25) and 253 nM (U7Ub25.2540). However, deletion of the C-terminal diglycine (U7Ub25dGG) abrogates inhibition of USP5. Bottom: USP5 is strongly activated by wildtype ubiquitin, but not by the U7Ubs. All activities are normalized to the initial rate at zero concentration ubiquitin, with the exception of "USP5 (Max rate)," which is normalized to the maximal velocity measured after the initial lag phase.

The ability of the U7Ub25 and U7Ub25.2540 variants to compete for wildtype ubiquitin in a kinetic assay was assessed. As shown in FIG. 12A, U7Ub25 and U7Ub25.2540 inhibit full-length USP7 activity with similar $IC_{50}$'s (250 nM and 160 nM, respectively), which represents a greater than 1,000 fold improvement relative to the ability of wildtype ubiquitin to inhibit USP7 (Table 11). This is consistent with Kd values measured by biolayer interferometry and ITC (FIGS. 1D, 5C, and Table 9).

TABLE 11

$IC_{50}$ (nM) of U7Ub variants against USP deubiquinases

|  | USP7 | USP2[§] | USP5 | USP10* | USP47 |
|---|---|---|---|---|---|
| Wildtype | N.D. | 13,700 ± 1798 | 8,660 ± 716 | ND | 13,200 ± 1975 |
| U7Ub25 | 172 ± 9 | ND | 373 ± 32 | ND | 1337 ± 385 |
| U7Ub25.2540 | 104 ± 4 | ND | 251 ± 25 | ND | 752 ± 214 |
| U7Ub25.2540ΔGG | 203 ± 11 | NT | ND | NT | NT |

[§]catalytic domain;
*end point assay (Methods);
ND = not detectable;
NT = not tested In order to test the specificity with which U7Ub25 and U7Ub25.2540 inhibit USP-type enzymes, the $IC_{50}$ of these two ubiquitin variants against USP2 catalytic domain, USP5, USP10 and USP47 was measured (FIG. 12B-E and Table 11). USP2 was chosen as a general highly active deubiquitinase, whereas USP5 was chosen for containing multiple ubiquitin binding sites with disparate functions.[16] USP47 is the most closely related deubiquitinase to USP7, and is a stringent test of specificity. USP10 is known to deubiquitinate and stabilize p53, and hence is directly opposed to the action of USP7. Molecules that target USP7 to stabilize p53 must therefore avoid cross-reactivity with USP10.

Both U7Ub25 and U7Ub25.2540 have no effect on USP2 and USP10 activity at concentrations up to 20 µM (FIG. 12B, C), and are similar to wildtype ubiquitin in their inhibition of USP47 (FIG. 5D). Surprisingly, both U7Ub25 and U7Ub25.2540 are relatively potent inhibitors of USP5 (IC50=373 nM and 251 nM, respectively), compared to wildtype ubiquitin ($IC_{50}$=8.27 µM) (FIG. 12E, top). However, the inhibitory mechanism is different for these two variants compared to the wildtype. Sub-inhibitory concentrations of ubiquitin strongly activate USP5 through binding to its zinc finger (ZnF4) domain, an activity that is proposed to regulate USP5's cellular function against linear ubiquitin chains.[16] Notably, neither U7Ub25 nor U7Ub25.2540 allosterically activate USP5 (FIG. 12E, bottom), suggesting that they do not engage the regulatory ZnF4 domain, and only bind to the catalytic USP domain. Since USP5's ZnF4 domain primarily engages the C-terminus of ubiquitin, the last two glycines of U7Ub25 were deleted in an attempt to abrogate USP5 inhibition. The resulting variant, U7Ub25ΔGG, retains its potency towards full-length USP7, but no longer inhibits USP5 (FIG. 12A, E).

In sum, this example demonstrates that both the U7Ub25 and U7Ub25.2540 conformationally stabilized ubiquitin variants inhibit USP7 and USP5 enzymatic activity while having no effect on USP2 or USP10.

Example 6

The U7Ub25.2540 Conformationally Stabilized Ubiquitin Variant is a Potent and Selective USP7 Inhibitor in Human Cells Since the U7Ub variants are based on a ubiquitin scaffold, this Example examines whether stabilized ubiquitin variants interact with and/or interfere with the cellular ubiquitin ligation machinery as well as whether the variants are able to be incorporated into polyubiquitin chains.

Materials and Methods

Mammalian Expression Constructs and Cell Culture

The 3XHA-wildtype ubiquitin construct was produced by synthesizing 3XHA ubiquitin (MCLAB) and subcloning into pcDNA3.1 (Invitrogen). The 3XHA-U7Ub25.2540 construct was produced by PCR amplifying U7Ub25.2540 from phage solution and subcloning the product into a modified pcDNA3.1 (+) vector (Invitrogen) that includes an N-terminal 3X HA tag. The 3XHA pcDNA3.1 vector was generated by ligating in a 3XHA sequence that includes the Kozak sequence using restriction sites NheI and HindIII as follows:

gctagcGCCGCCACCatggagTACCCATACGACGTACCAGATTACGCTTA

CCCATACGACGTACCAGATTACGCTTACCCATACGACGTACCAGATTACG

CTaagctt (SEQ ID NO: 14).

The U7Ub25.2540 was then cloned into the 3×HA pcDNA3.1 (+) vector using BamHI and EcoRI restriction sites. The ΔGG versions (UbΔGG and U7Ub25.2540ΔGG) were generated by mutating Gly 75 and 76 (GGTGGT) to stop codons (TGATGA). The human cell lines HEK293T, U2OS, and SiHa were obtained from ATCC, whereas HCT116 parental and USP7−/− cell lines were obtained from Horizon Discovery. Cells were maintained following standard protocols and DNA transfections were achieved using Lipofectamine 2000 transfection reagent (Invitrogen).

Immunoblotting Analysis and Immunoprecipitations

Antibodies generated against the following proteins were purchased from the indicated vendors and were used for immunoblotting using standard protocols as described previously.[56] HA-HRP (Sigma HA-7), Ubiquitin-HRP (Santa Cruz Biotech P4D1), USP7 (Bethyl A300-034A), USP47 (AbCam ab72143), USP14 (Bethyl A300-919A), USP10 (AbCam ab70895), USP5 (AbCam ab84695), UCHL1 rabbit polyclonal (Invitrogen), tubulin murine monoclonal (MP biomedical), MDM2 (Calbiochem Ab-1), p53 (Neomarkers Ab-8), p21 (AbCam ab7960), and GAPdH (Assay Designs, 1D4). Standard immunoprecipitations were performed as described previously (Wertz et al Nature 2004) using the indicated antibodies or antibody-conjugated agarose: anti-HA agarose (Roche 3F10) or anti-myc (Covance 9E10). Generation of the ubiquitin linkage-selective antibodies and the specific protocols optimized for immunoprecipitations using these antibodies have been described previously.[57-59]

Proteomics and Mass Spectrometry

Anti-HA immunoprecipitates were purified as described above. Protein complexes were eluted in SDS sample buffer, separated by SDS-PAGE, and then digested with trypsin. Peptides were separated by reverse phase chromatography followed by tandem mass spectrometric analysis in a LTQ-Orbitrap Velos (Thermo Fisher). MS/MS data were searched with Mascot[60] (Matrix Science, London, UK), using a 50 ppm precursor ion tolerance and full trypsin specificity against a concatenated target-decoy database containing human proteins extracted from the Uniprot database and common contaminants. Peptide spectral matches were filtered to a 1% FDR using linear discriminant analysis.

Results

Figure 13:
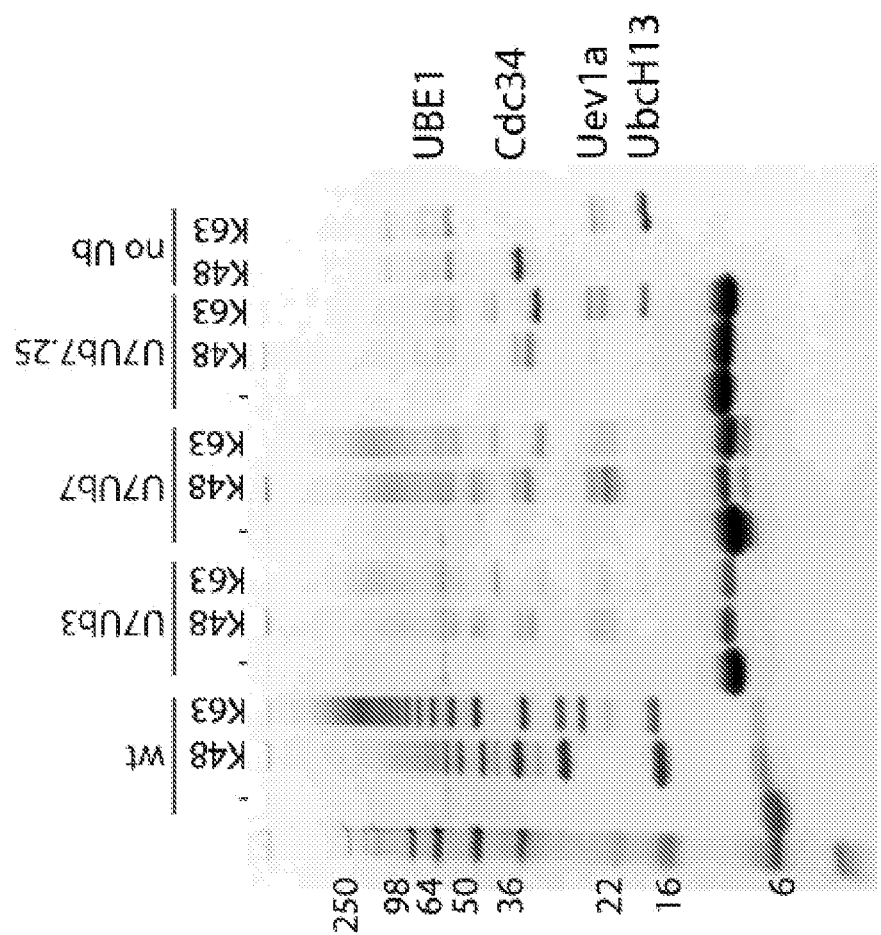
FIG. 13 depicts anti-USP7 variants are not efficiently incorporated into either Lys48- or Lys63-linked chains by E1 and E2 enzymes. Neither U7Ub3 nor U7Ub7 are efficiently incorporated into K48- or K63-linked chains in biochemical ligation assays utilizing the E1 UBE1 and the E2s Cdc34 (that promotes K48 polyubiquitination) or Uev1a/UbCH13 (that promote K63 polyubiquitination); depletion of the monomer ubiquitin pool supports that the variants partially engage the E1 and/or the E2 enzymes evaluated. In contrast, no detectable polymerization is achieved with U7Ub25.

Neither U7Ub3 nor U7Ub7 are efficiently incorporated into K48- or K63-linked chains in biochemical ligation assays utilizing the E1 UBE1 and the E2s Cdc34 (that promotes K48 polyubiquitination) or Uev1a/UbCH13 (that promote K63 polyubiquitination); depletion of the monomer ubiquitin pool supports that the variants partially engage the E1 and/or the E2 enzymes evaluated (FIG. 13). In contrast, no detectable polymerization is achieved with U7Ub25 although it remains possible that including E3 proteins in the biochemical assay may enhance polymerization of the U7Ub variants.

Figure 14:
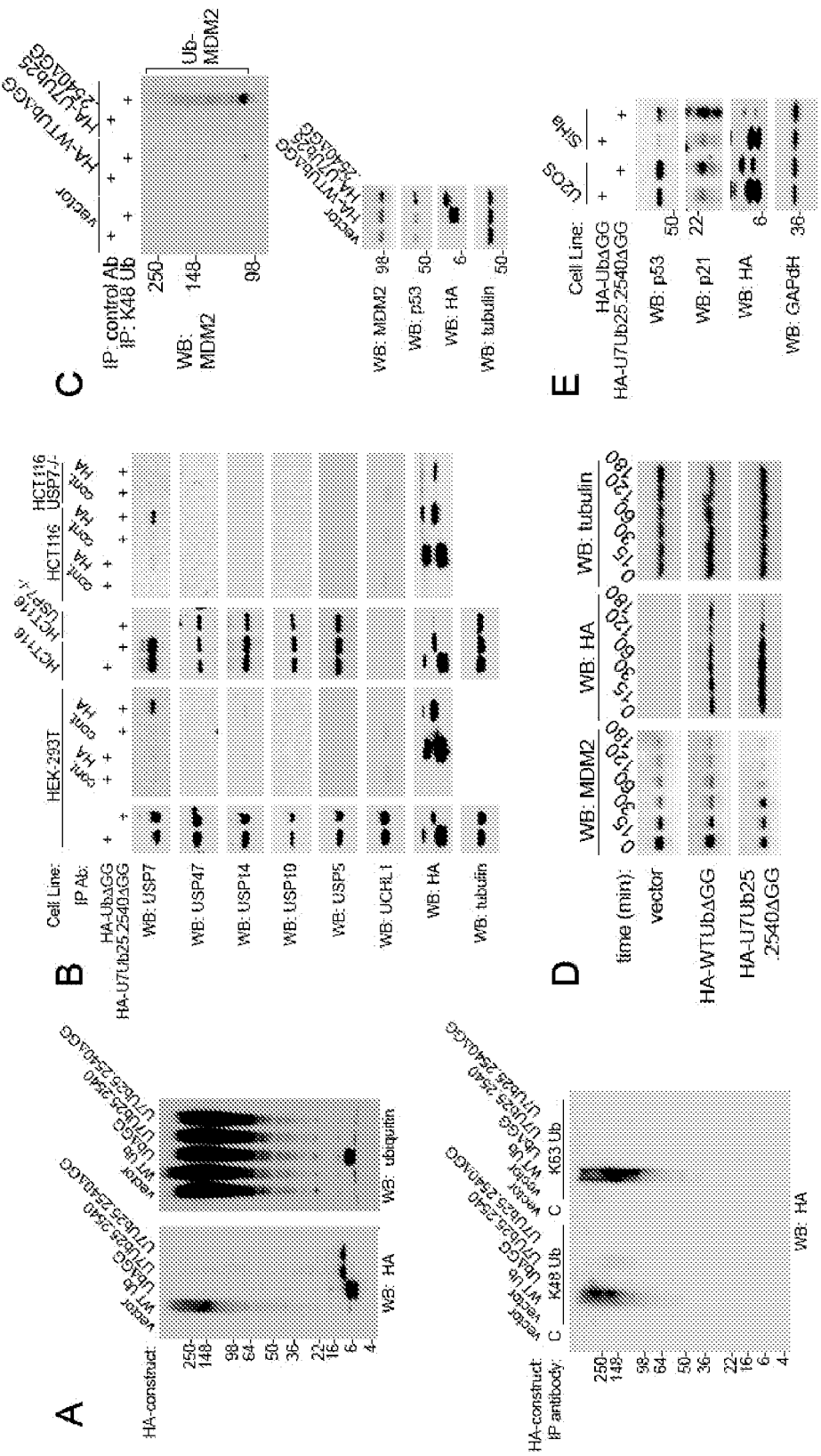
FIG. 14 depicts U7Ub25.2540 variants are selective inhibitors of endogenous USP7 in the cellular environment. A) U7Ub25.2540 is weakly incorporated into polyubiquitin chains in cells; U7Ub25.2540ΔGG abrogates chain incorporation. Investigation of specific ubiquitin chain linkages is shown in FIG. 15. HCT116 cells were transfected with the indicated expression constructs and lysates were blotted as indicated or were immunoprecipitated with the indicated antibodies; the isotype control (C) antibody is cell culture grade Herceptin. B) U7Ub25.2540ΔGG selectively binds endogenous USP7 relative to other cellular DUBs. Anti-HA or isotype antibody control (anti-c-myc) immunoprecipitates or cell lysates were blotted with antibodies to the indicated proteins. The HCT116 USP7−/− cell line was used as an additional control for USP7 association. C) Expression of U7Ub25.2540ΔGG in cells promotes MDM2 polyubiquitination, an indication of endogenous USP7 inhibition. U2OS cells were transfected with the indicated constructs and cell lysates were immunoprecipitated with a control (Trastuzumb) or a K48 linkage-selective antibody and blotted to reveal MDM2 ubiquitination. D) Expression of U7Ub25.2540ΔGG in cells increases MDM2 turnover, a reflection of endogenous USP7 inhibition. U2OS cells were transfected with the indicated constructs, treated with 100 μM cycloheximide, collected at the indicated time points, and lysates were blotted with the indicated antibodies. E) Expression of U7Ub25.2540ΔGG in cells stabilizes p53, subsequently upregulating the p53 response gene p21. U2OS or SiHa cells were transfected with the indicated expression constructs and lysates were blotted with the indicated antibodies.
Figure 15:
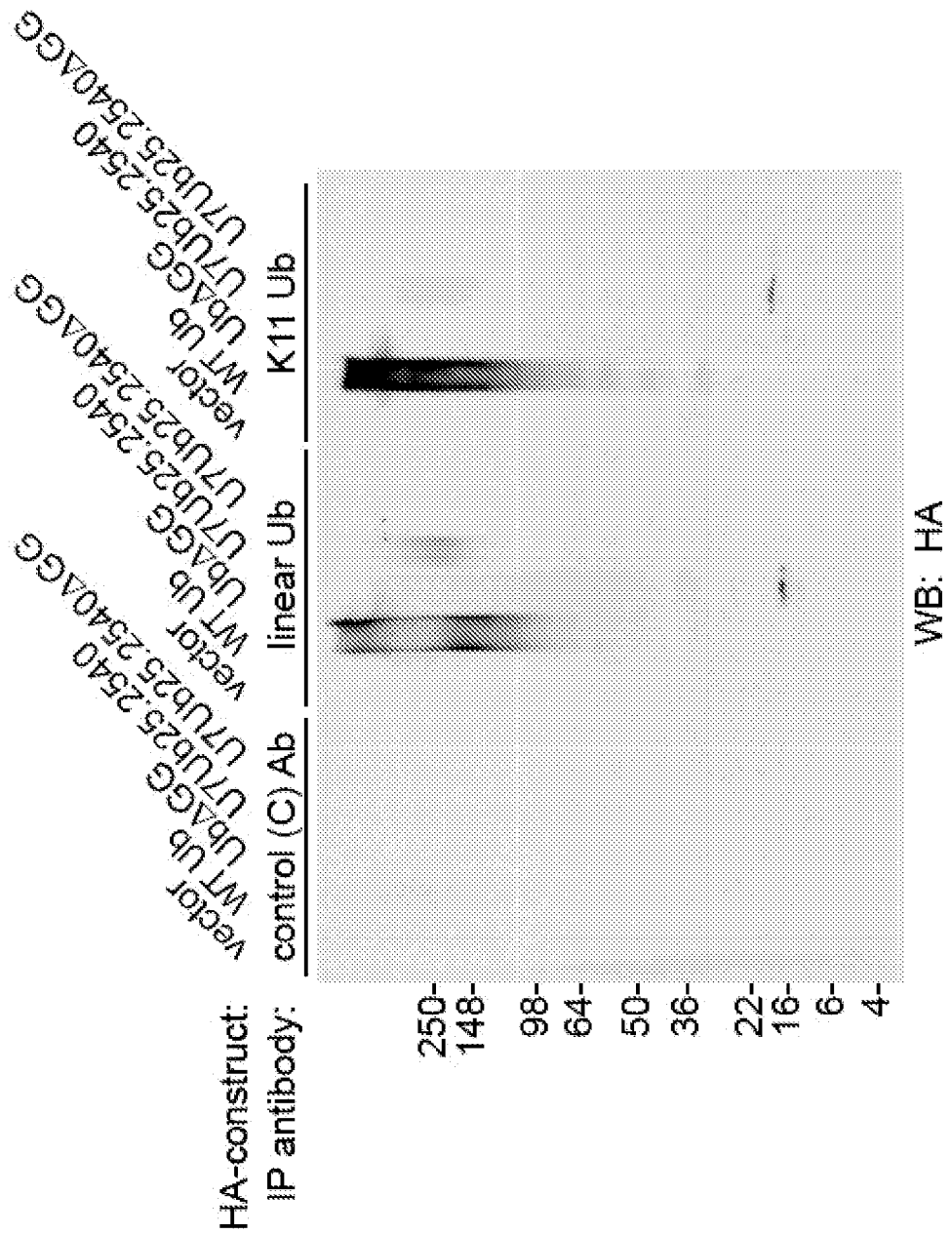
FIG. 15 depicts U7Ub25.2540 being weakly incorporated into polyubiquitin chains in cells; U7Ub25.2540ΔGG abrogates chain incorporation. HCT116 cells were transfected with the indicated expression constructs and lysates were immunoprecipitated with the indicated antibodies; the isotype control (C) antibody is Trastuzumab.

The interaction of the U7Ub variants with cellular ubiquitination enzymes was next explored. To this end HA epitope-tagged versions of wildtype ubiquitin, ubiquitin ΔGG, U7Ub25.2540, and U7Ub25.2540ΔGG were expressed in human cells (FIG. 14A). Similar to the biochemical assays, U7Ub25.2540 was poorly incorporated into polyubiquitin chains, despite the presence of the ubiquitin ligases expressed in the cellular environment (FIGS. 14A and 15). No changes in cellular ubiquitination patterns were detectable by western blot analysis, indicating that expression of the U7Ub variants has a minimal impact on the endogenous ubiquitin ligation machinery (FIG. 14A).

Figure 16:
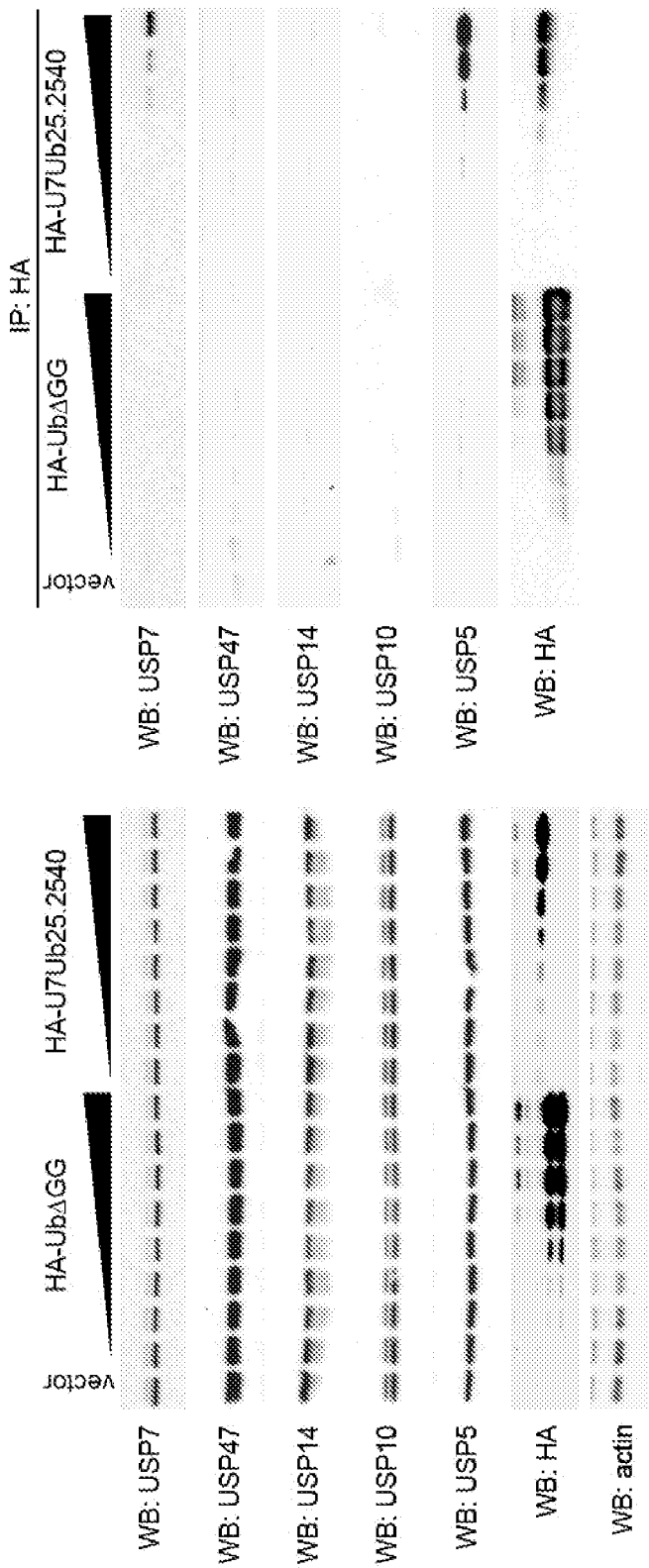
FIG. 16 depicts U7Ub25.2540 binding to endogenous USP7 and USP5 relative to other cellular DUBs. HCT116 cells were transfected as indicated and anti-HA immunoprecipitates or cell lysates were blotted with antibodies to the indicated proteins.

The DUB binding selectivity and the DUB inhibition efficacy of the U7Ubs in the cellular environment was next explored. Endogenous USP7 fails to associate with HA-wildtype ubiquitin but is detected HA-U7Ub25.2540 immunoprecipitates in a dose-dependent manner (FIG. 16). USP5 was the only other DUB detected in HA-U7Ub25.2540 immunoprecipitates (FIG. 16). Since deleting the C-terminal diglycine from U7Ub25 provided additional specificity for USP7 in enzymatic inhibition assays, the C-terminus of the affinity matured variant was removed (U7Ub25.2540ΔGG). When transfected into human cell lines this clone specifically immunoprecipitates endogenous USP7 without apparent binding to USP5 (FIG. 14B). These data are confirmed by mass spec analysis: USP7 is substantially enriched (up to 15-fold) in HA-U7Ub25.2540ΔGG immunoprecipitates from two cell lines, whereas most other DUBs are pulled down by HA-U7Ub25.2540ΔGG to an equal or lesser extent relative to the diglycine-deleted wildtype ubiquitin. (FIG. 17). Consistent with endogenous USP7 binding, expression of HA-U7Ub25.2540ΔGG also inhibits USP7 catalytic activity as indicated by enhanced MDM2 ubiquitination (FIG. 14C) and turnover (FIG. 14D). The net result of inhibiting USP7 activity and decreasing MDM2 protein levels is stabilization of the p53 tumor suppressor (FIG. 14E).

Therefore this example shows that the collective biophysical, biochemical, and cellular data demonstrate that Conformational Display is a powerful tool that may be used to engineer ubiquitin variants that selectively bind and thereby inhibit the cellular action of the oncogenic DUB USP7.

Example 7

Use of Conformational Display to Identify a Conformationally Stabilized USP14-Binding Ubiquitin Variant Because of their key role in the regulation of intracellular signaling, DUBs have emerged as promising new therapeutic targets.[31] For example, small molecule inhibition of the proteasome-associated USP14 DUB has been shown recently to enhance degradation of proteins involved in amyloidogenic neurodegeneration[32] and to prevent tumor progression.[33] The study of USP-type DUB mechanism and regulation is complicated by their relatively poor activity: the catalytic domain of USP-type DUBs typically has an enzyme efficiency of $10^3$ to $105$ $M^{-1}$ $s^{-1}$, and high micromolar substrate affinities, necessitating the use of covalent suicide "warheads" in structural studies.[34] By contrast, UCH-type DUBs are often highly active, with enzyme efficiencies of up to $10^8$ $M^{-1}$ $s^{-1}$ and affinity for ubiquitin in the low nanomolar range.[35-36] This example investigates whether Conformational Display can be used to generate a stabilized ubiquitin variant that tightly binds to USP14.

Materials and Methods

Identification of "Up" and "Down" β1-β2 Conformations

Figure 21:
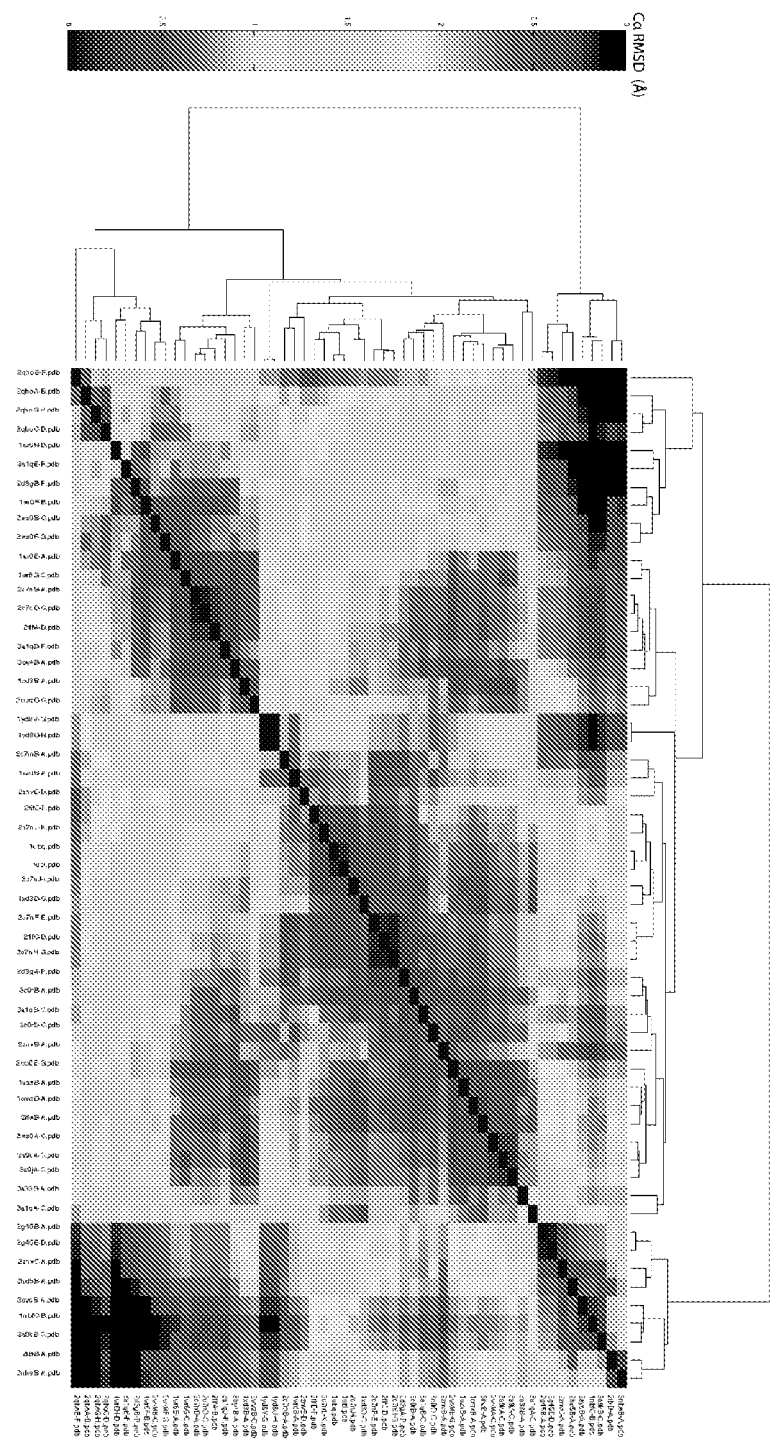
FIG. 21 depicts a clustered heatmap of β1-β2 RMSD for all Ub-partner structures in the PDB. Structures were aligned and clustered as described in the results and methods. Complexes listed along each axis are in the format <PDB code><ubiquitin chain letter>-<partner chain letter>. For example, 2ibiB-A represents the β1-β2 loop from ubiquitin (chain B) bound to USP2 (chain A) in PDB code 2ibi.

All crystal structures of ubiquitin bound to a partner protein determined at a resolution greater than 2.5 Å were obtained from the PDB and split into individual models containing single ubiquitin-partner pair each. Two apo ubiquitin structures (1ubi and 1ubq) were also included to determine the dominant apo conformation of β1-β2. After manual inspection of each structure, models were excluded if the β1-β2 loop was clearly involved in crystal packing. The remaining 56 structures (Table 12) were pairwise aligned on the Cα's of the globular core sans β1-β2 (residues 1-5 and 11-70) and the Cα RMSD of the β1-β2 loop (residues 6-10) was calculated. These pairwise RMSDs were organized into a matrix and clustered using MATLAB (clustergram, Bioinformatics toolbox). Visual inspection of structures in each of the two major clusters revealed that they represented "up" and "down" conformations of β1-β2. The fully labeled clustergram, containing PDB codes for each complex and chain identifiers of each partner is available in FIG. 21.

TABLE 12

PDBs used for clustering β1-β2 loop conformations.
Names are in the format
<PDB code><ubiquitin chain letter>-<partner chain letter>

1cmxB-A.pdb
1nbfC-B.pdb
1ubi.pdb
1ubq.pdb
1uzxB-A.pdb
1wr6E-A.pdb
1wr6F-B.pdb
1wr6G-C.pdb
1wr6H-D.pdb
1wrdB-A.pdb
1xd3B-A.pdb
1xd3D-C.pdb
1yd8U-H.pdb
1yd8V-G.pdb
2ayoB-A.pdb
2c7mB-A.pdb
2c7nB-A.pdb
2c7nD-C.pdb
2c7nF-E.pdb
2c7nH-G.pdb
2c7nJ-I.pdb
2c7nL-K.pdb
2d3gA-P.pdb
2d3gB-P.pdb
2fifA-B.pdb
2fifC-D.pdb
2fifE-F.pdb
2g45B-A.pdb
2g45E-D.pdb
2hd5B-A.pdb
2ibiB-A.pdb
2qhoA-B.pdb
2qhoC-D.pdb

TABLE 12-continued

PDBs used for clustering β1-β2 loop conformations.
Names are in the format
<PDB code><ubiquitin chain letter>-<partner chain letter>

2qhoE-F.pdb
2qhoG-H.pdb
2wwzB-C.pdb
2wx0A-C.pdb
2wx0B-C.pdb
2wx0E-G.pdb
2wx0F-G.pdb
2znvB-A.pdb
2znvC-A.pdb
2znvE-D.pdb
3a1qA-C.pdb
3a1qB-C.pdb
3a1qD-F.pdb
3a1qE-F.pdb
3a33B-A.pdb
3a9jA-C.pdb
3a9kA-C.pdb
3a9kB-C.pdb
3by4B-A.pdb
3c0rB-A.pdb
3c0rD-C.pdb
3ifwB-A.pdb
3nheB-A.pdb Computational Design to Determine Residues Important for β1-β2 Conformation Positions that influence the conformation of β1/β2 were identified using a computational design strategy. Briefly, residues within the β1/β2 region and the hydrophobic core of ubiquitin were computationally allowed to mutate in either the up or down states, and positions that adopted different preferred identities compared to wild-type ubiquitin and the opposite state were considered for variation in a phage display experiment.

Figure 22:
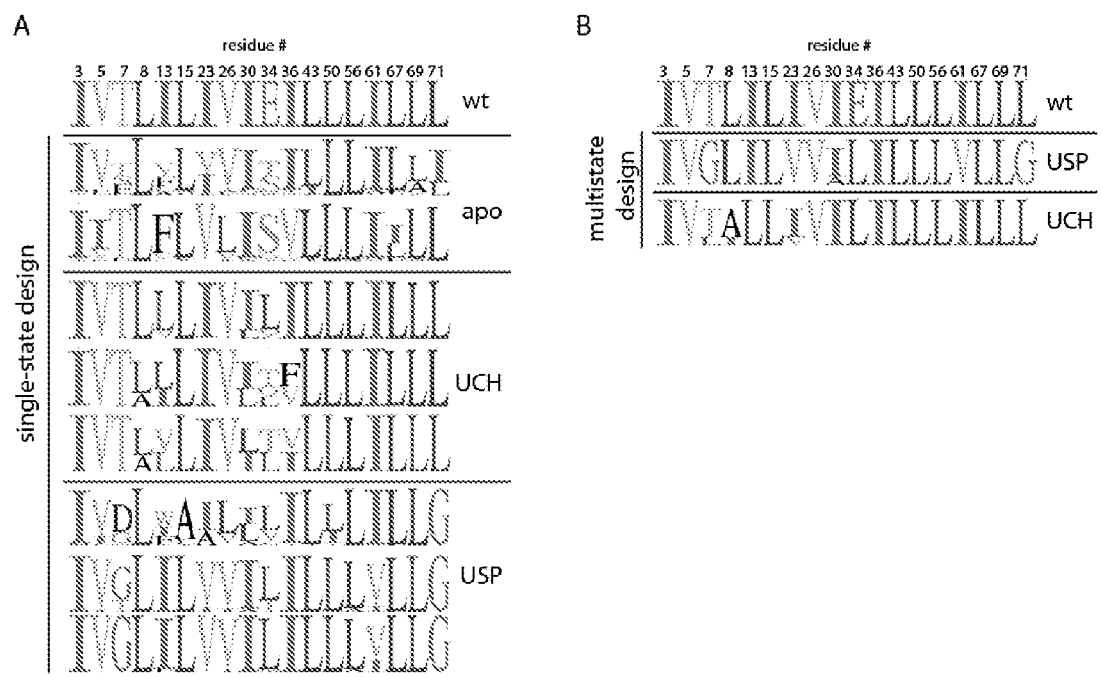
FIG. 22 depicts design results from U14Ub engineering experiments. Ubwt (SEQ ID NO: 1) sequence with specific residues as shown. A) Consensus sequence preference for single-state design and B) multi-state design.

The following template crystal structures were selected for computational design: apo wild-type ubiquitin (1ubi), bound "up" states (1cmx, 1xd3, 3ifw), and USP-bound "down" states (2ayo, 2hd5, 2ibi). Both single state and multistate design strategies were employed, with positions 3, 5, 7, 8, 13, 15, 23, 26, 30, 34, 36, 43, 50, 56, 61, 67, 69, and 71 allowed to mutate. In the single state protocol, each template was independently designed 10,000 times using RosettaDesign (Kuhlman, et al., *Science* 302, 1364-1368 (2003)) and the top 1,000 sequences by total system energy were compared to the other templates (FIG. 22A). In the multistate protocol, each template was designed using a genetic algorithm was used to optimize a fitness function that favored three "down" positive states (2ayo, 2hd5, 2ibi) and disfavored three "up" negative states (1cmx, 1xd3, 3ifw) across a population of 2000 members 150 generations (Havranek & Harbury, *Nat. Struct. Biol.* 10, 45-52 (2003)). This protocol was independently repeated three times for the backbone template of each positive state and position-specific score matrices were constructed with Boltzmann weighting of sequence fitnesses (FIG. 22B) (Smith & Kortemme, *PLoS ONE* 6, e20451 (2011)). Both single-state and multistate methods indicated that the wild-type residues at positions 7, 8, 13, 34, 36, 61, and 71 were suboptimal for the "down" USP-binding state (FIG. 22). These positions, together with neighboring position 69 were randomized to NNK codons in subsequent phage display experiments.

Computational Cross-Docking

Structures of ubiquitin bound to USP- or UCH-type deubiquitinases (PDB codes 3IFW, 2AYO, 2HD5, 1CMX, 1XD3, and 2IBI) were separated into ubiquitin (chain B) and deubiquitinase (chain A) components. Only the globular portion of ubiquitin (residues 1-70) was docked, to avoid crystallographic bias arising from positioning of the flexible C-terminal tail. Memory of the bound complex was removed by prepacking all sidechains in the apo state. Each ubiquitin structure was placed into the binding site of every deubiquitinase by aligning on the cognate ubiquitin, then docked onto the deubiquitinase using RosettaDock (Gray, et al., *J. Mol. Biol.* 331, 281-299 (2003)) after a small random perturbation of 3 Å and 8°. 1,800 trajectories were run per ubiquitin-deubiquitinase complex, and the total system energies of each combination were normalized relative to the lowest-scoring model, which was set to a score of zero. Cα RMSD for residues 1-70 was calculated relative to the cognate structure of ubiquitin bound to the deubiquitinase in question.

Display of Ubiquitin on M13 Phage

Ubiquitin was displayed on the surface of M13 bacteriophage by modifying a previously described phagemid pS2202d (Skelton, N. J. et al., *J. Biol. Chem.* 278, 7645-7654 (2003)). Standard molecular biology techniques were used to replace the fragment of pS2202d encoding Erbin PDZ domain with a DNA fragment encoding for ubiquitin. The resulting phagemid p3Ub contained an open reading frame that encoded for the maltose binding protein secretion signal, followed by gD tag and Ubiquitin and ending with the C-terminus domain of minor coat protein p3. *E. Coli* harboring p3Ub were co-infected with M13-KO7 helper phage and were amplified following the standard protocol (Tonikian et al., *Nat Protoc.*, 2(6):1368-86 (2007)). The propagated phage was purified according to the standard protocol (Tonikian et al., *Nat Protoc.*, 2(6):1368-86 (2007)) and re-suspended in 1 mL PBT buffer (PBS, 0.5% BSA and 0.1% Tween 20), resulting in the production of phage particles that encapsulated p3Ub DNA and displayed Ubiquitin. The display level was analyzed using a phage ELISA.

Library Construction and Sorting

Ubiquitin libraries were constructed using the Kunkel mutagenesis method (Kunkel, et al., *Meth. Enzymol.* 154, 367-382 (1987)). Wild-type ubiquitin residues T7, L8, I13, E34, I36, L69 and L71 were randomized with the NNK codon. A stop template (single strand DNA of p3Ub containing three stop codons in the regions of 7-13, 34-36 and 69-71) was used to construct a library that contained ~2×10$^{10}$ unique members. The library was cycled through rounds of binding selection in solution against the C-terminally monobiotinylated catalytic domain of USP14 (residues D91-Q494) with a C114A mutation (designated as USP14catC114A). For round one, 20 µg of biotinylated USP14catC114A was incubated with 1 ml of phage library (~1×10$^{13}$ pfu/mL) at 4° C. for 2 h and captured for 15 min at room temperature by 200 µL of Dynabeads® MyOne Streptavidin that had been previously blocked with blocking buffer (PBS, 1% BSA). The supernatant was discarded and the beads were washed three times with PBS, 0.1% Tween20. The bound phage was eluted with 400 µL 0.1 M HCl for 7 min and immediately neutralized with 60 µL of 1 M Tris, pH 13. The eluted phage was amplified as described by Tonikian et al., *Nat Protoc.*, 2(6):1368-86 (2007). For round two, the protocol was the same as round one except for using 10 µg biotinylated USP14catC114A and 100 µL of Dynabeads. For round three and round five, 2 µg biotinylated USP14catC114A was incubated with the amplified phage from the previous round and the phage-USP14catC114A complex was captured by NeutrAvidin-coated plates previously treated with blocking buffer. Round four was identical to round three except for using Strepavidin-coated plates to capture biotin-USP14catC114A-phage complex. Phage was propagated in *E. coli* XL1-blue with M13-

KO7 helper phage at 30° C. following the standard protocol (Tonikian et al., *Nat Protoc.*, 2(6):1368-86 (2007)).

Spot Phage ELISA

After five rounds of binding selection, individual phage clones were picked and inoculated into 450 μl 2YT media containing 50 μg/ml carbenecillin and M13-KO7 helper phage in 96-well blocks, which were grown at 37° C. overnight. The supernatant was analyzed with spot phage ELISA as follows: biotinylated USP14catC114A were captured to NeutrAvidin-coated 384-well Maxisorp immunoplates and phage supernatant diluted (1:3) with PBT buffer was added to the wells. The plates were washed and bound phage was detected with anti-M13-HRP followed by TMB substrate. In these assays, phage binding to NeutrAvidin alone was tested in parallel to assess background binding. Clones whose binding signals for USP14catC114A were more than 5 times higher than to NeutrAvidin (background) were considered positive. Positive clones were subjected to DNA sequence analysis.

Ubiquitin Variant Expression and Purification

DNA encoding ubiquitin variants were cloned into a pET derivative vector (EitNTH vector) with an N-terminal 6×His tag (SEQ ID NO: 2) and expressed in E. *Coli* as previously described (Dueber, et al., *Science* 334, 376-380 (2011)). Briefly, BL21 (DE3) gold *E. coli* cells were transformed with the U14Ub containing plasmids and grown in LB media containing 50 mg/L carbenicillin to an $OD_{600}$ of ~0.7 and induced with 0.2-0.5 mM isopropyl β-D-1-thiogalactopyranoside for 16 hours at 16° C. and then harvested by centrifugation. The cells were resuspended in PBS plus Roche complete protease inhibitors (no EDTA) and 10 mM imidazole and lysed via sonication. The soluble fraction was loaded onto Ni-NTA resin (Qiagen) and washed with ca. ten column volumes of PBS plus 20 mM imidazole and then eluted with PBS plus 300 mM imidazole. The 6×His tag (SEQ ID NO: 2) was then cleaved from the protein for crystallography and NMR spectroscopy via the addition of TEV protease and dialyzed against PBS overnight at 4° C. This solution was then run over Ni-NTA resin to remove the cleaved tag and the TEV. Samples were then concentrated with 3 kDa MWCO Ultra-free 15 centrifugal filter devices (Amersham) and ran over a gel filtration column (S75 Superdex 16/60, GE Healthcare). Fractions were then pooled, analyzed by SDS-PAGE, and concentrated to 1-20 mg/mL.

Samples were prepared for NMR spectroscopy with labeling performed according to the method of Cai et al. (*J Biomol NMR* 11, 97-102 (1998)) with the modification that cells were spun down and transferred to M9 media containing U-$^2$H, $^{13}$C-D-glucose and ⅔ $^2$H$_2$O. Approximately 50% deuteration is required for the implementation of the μs $R_{ex}$ experiment (Hansen, et al., *J. Am. Chem. Soc.* 129, 11468-11479 (2007)). NMR samples contained 10% $^2$H$_2$O and 0.1 mM trimethylsilylpropionate. Deuterium incorporation was determined to be ca. 50% by mass spectrometry.

Binding Assay by ELISA

The biotinylated USP14catC114A, UCHL3, or UCHL1 was captured on NeutrAvidin coated Maxisorp® Plate that was previously blocked by Blocking Buffer and was incubated with 1:3 serial dilution of His-tagged Ubiquitin variants at concentration range of 0-20 μM for 1 hour at 4° C. in PBT buffer. The plate was then washed with PT buffer and the bound His-tagged proteins were detected by anti-PentaHis-HRP ('PentaHis' disclosed as SEQ ID NO: 13) conjugate (Qiagen, Cat. No. 34460, Germantown, Md.) followed by TMB substrate.

Affinity Measurement by Biolayer Inferiority

The binding affinities of Ubiquitin variants to USP14catC114A were measured by biolayer interferometry on an OctetRed 384 (Fortebio, Menlo Park, Calif.). Strepavidin biosensors (Fortebio, Cat. No. 18-5020) were loaded with biotinylated USP14catC114A in PBS buffer containing 0.05% Tween20 and 0.5% BSA, washed in the same buffer and transferred to wells containing ubiquitin variants at concentrations ranging from 0-50 μM in the same buffer. The signal against the reference cell that contains buffer only was subtracted from all the binding data. For each concentration of ligand, two biosensors, with or without biotinylated USP14catC114A loaded, were used to detect binding in parallel. The signal detected by the bare biosensor was subtracted from the binding signal from the biosensor that loaded with USP14catC114A. The dissociation constant, $K_D$, was obtained by non-linear fitting of the responses to a steady state algorithm using Octet software.

For kinetics, the association data was fitted using KaleidaGraph software to the following equation for a biphasic association model:

$$r = R_{max} f_{fast}(1-e^{-k_{fast}t}) + R_{max}(1-f_{fast})(1-e^{-k_{slow}t}) \quad \text{(equation 1)}$$

$R_{max}$ is the maximum response
$f_{fast}$ is the fraction of contribution from the fast phase binding toward the total $R_{max}$
$k_{fast}$ is the association constant for the fast phase binding
$k_{slow}$ is the association constant for the slow phase binding
r is the response at any time point and t is the time
The dissociation constant $k_{off}$ was obtained by fitting the dissociation data to 1:1 model using Octet software.

For the fast phase, $k_{on} = (k_{fast} - k_{off})/[L]$ (equation 2), where [L] is the concentration of the ligands. For the slow phase, $k_{slow} = k_f + k_r/(1+[L]/K_D)$ (equation 3) is for "conformation selection" model and $k_{slow} = k_r + k_f/(1+K_D/[L])$ (equation 4) is for "induced-fit" model (Hammes, et al., *Proc. Natl. Acad. Sci. U.S.A.* 106, 13737-13741 (2009); James et al., *Science* 299, 1362-1367 (2003)).

The $K_D$ derived from kinetic fitting was calculated as $k_{off}/k_{on}$, in which $k_{on}$ was calculated from equation 2

From the shape of the dependence of $k_{slow}$ obtained from equation 1 at various ligand concentrations, it was clear that the induced-fit model (equation 4) describes the experimental data. In the fitting process, $K_D$ is a free parameter and the values obtained from the fitting of $k_{slow}$ were compared to the $K_D$ values obtained from both steady state and kinetic fitting (Table 13).

TABLE 13

Characterization of the U14Ubs with the highest apparent affinity for USP14.
Sequences and ELISA based EC50s of the five U14Ubs with the highest apparent affinity for USP14.

| | Sequence Position | | | | | | | EC$_{50}$ Usp14 (μM) | EC$_{50}$ UCHL3 (μM) | Steady State $K_D$ from BLI (μM) |
|---|---|---|---|---|---|---|---|---|---|---|
| | 7 | 8 | 13 | 34 | 36 | 69 | 71 | | | |
| wt | T | L | I | E | I | L | L | >50 | 0.0059 ± 0.0004 | 100 ± 29 |
| U14Ub1 | G | L | T | T | L | I | W | 0.30 ± 0.03 | 0.016 ± 0.001 | 2.9 ± 0.07 |

TABLE 13-continued

Characterization of the U14Ubs with the highest apparent affinity for USP14.
Sequences and ELISA based EC50s of the five U14Ubs with the highest apparent affinity for USP14.

| Sequence Position | 7 | 8 | 13 | 34 | 36 | 69 | 71 | EC$_{50}$ Usp14 (μM) | EC$_{50}$ UCHL3 (μM) | Steady State K$_D$ from BLI (μM) |
|---|---|---|---|---|---|---|---|---|---|---|
| U14Ub14 | G | F | L | T | L | S | W | 0.086 ± 0.004 | 0.013 ± 0.001 | 0.39 ± 0.03 |
| U14Ub2  | G | L | V | V | L | I | W | 0.28 ± 0.01   | 0.022 ± 0.001 | 0.77 ± 0.06 |
| U14Ub22 | G | L | L | S | L | V | W | 0.57 ± 0.01   | 0.054 ± 0.002 | 0.59 ± 0.07 |
| U14Ub24 | G | F | L | T | W | Y | H | 0.025 ± 0.01  | 1.2 ± 0.2     | 1.10 ± 0.10 |

Thermal Stability Measurements Using Differential Static Light Scattering

Thermal stability of the U14Ubs was compared to wild-type ubiquitin a commercial differential static light scattering instrument (Stargazer, Harbinger Biotech) as outlined by Vedadi et al (*Proc. Natl. Acad. Sci. U.S.A.* 103, 15835-15840 (2006). The concentration of each protein was 0.2 mg/mL Results To alter the dynamics of ubiquitin's β1/β2 loop, core positions where mutations are predicted to stabilize the USP-binding "down" state were computationally searched for, using both single-state and multi-state RosettaDesign.[37-39] Both types of design experiments identified a consistent set of positions where mutations were predicted to favor the USP-binding state. This information was incorporated into phage-displayed libraries of ubiquitin variants, which were panned against a catalytically inactive mutant of the USP domain of USP14 (FIG. 22).

Figure 18:
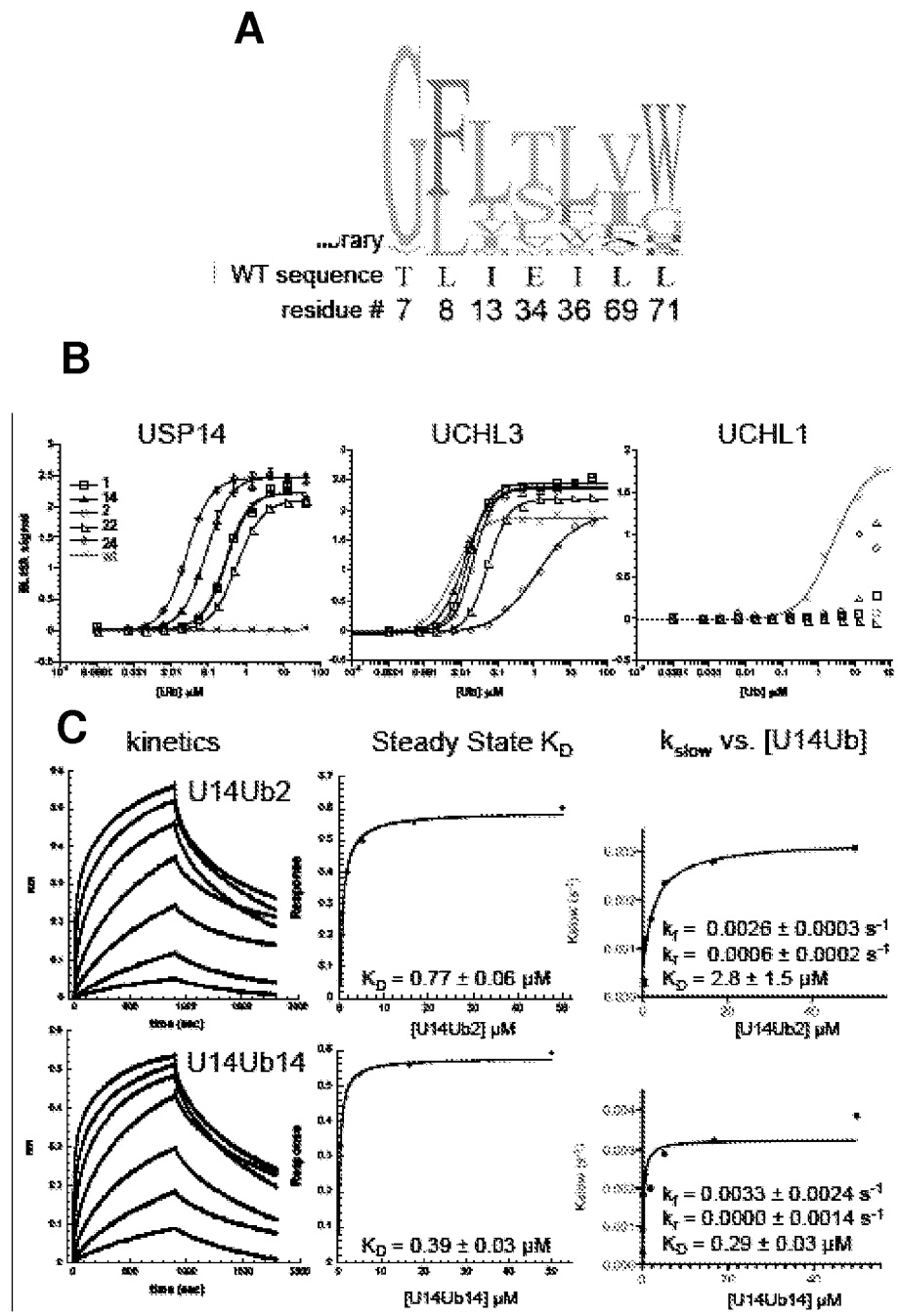
FIG. 18 depicts A) sequence preferences 23 phage clones isolated after five rounds of phage panning against USP14. Ubwt (SEQ ID NO: 1) sequence with specific residues as shown. B) Protein ELISAs demonstrate that the U14Ubs have an increased affinity for USP14 with a commensurate decrease in the affinity for UCHL3 and UCHL1. Wild-type ubiquitin curves are shown in blue, the various U14Ubs are in black. C) Biolayer interferometry titrations of USP14 with U14Ub2 and U14Ub14. The slow component of the biphasic association rate shows a dependence on the concentration of U14Ub that indicates an induced fit binding mechanism.[40] Dissociation constants determined by steady state and kinetic fits are in agreement.
Figure 27:
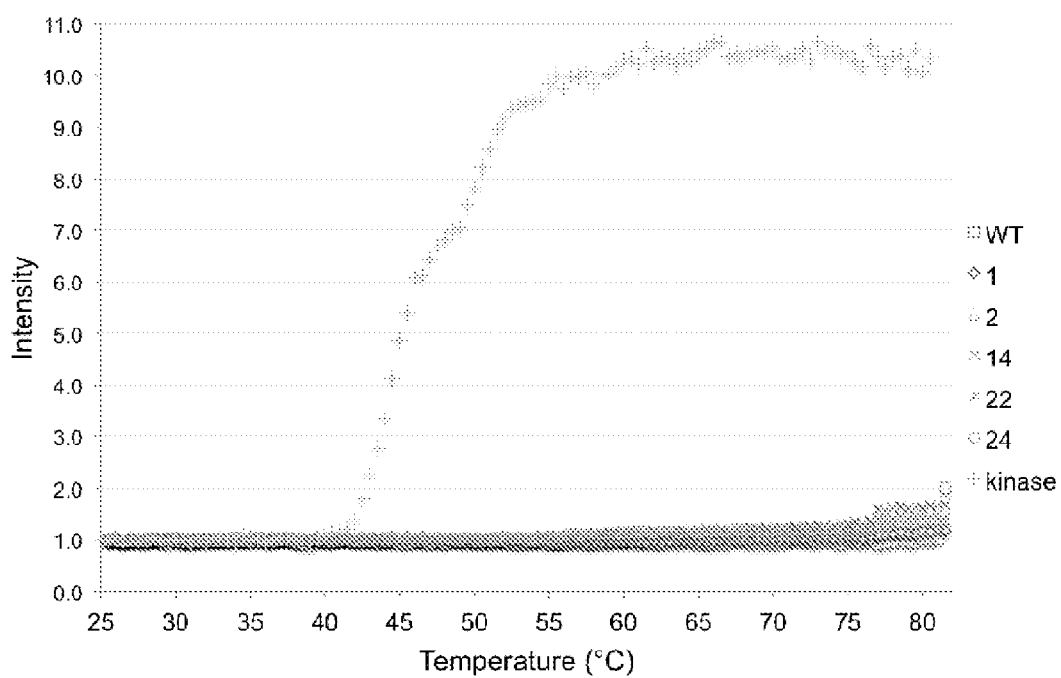
FIG. 27 depicts thermal stability measurements of U14Ubs and wild-type ubiquitin using differential static light scattering show that none of the mutants are dramatically destabilized relative to wild-type. The transition of a kinase is shown for clarity. Transitions of wild-type ubiquitin and the U14Ubs are unobserved up to 81° C., the high temperature limit of the instrument. Data were normalized to the intensity of the low-temperature baseline.
Figure 28:
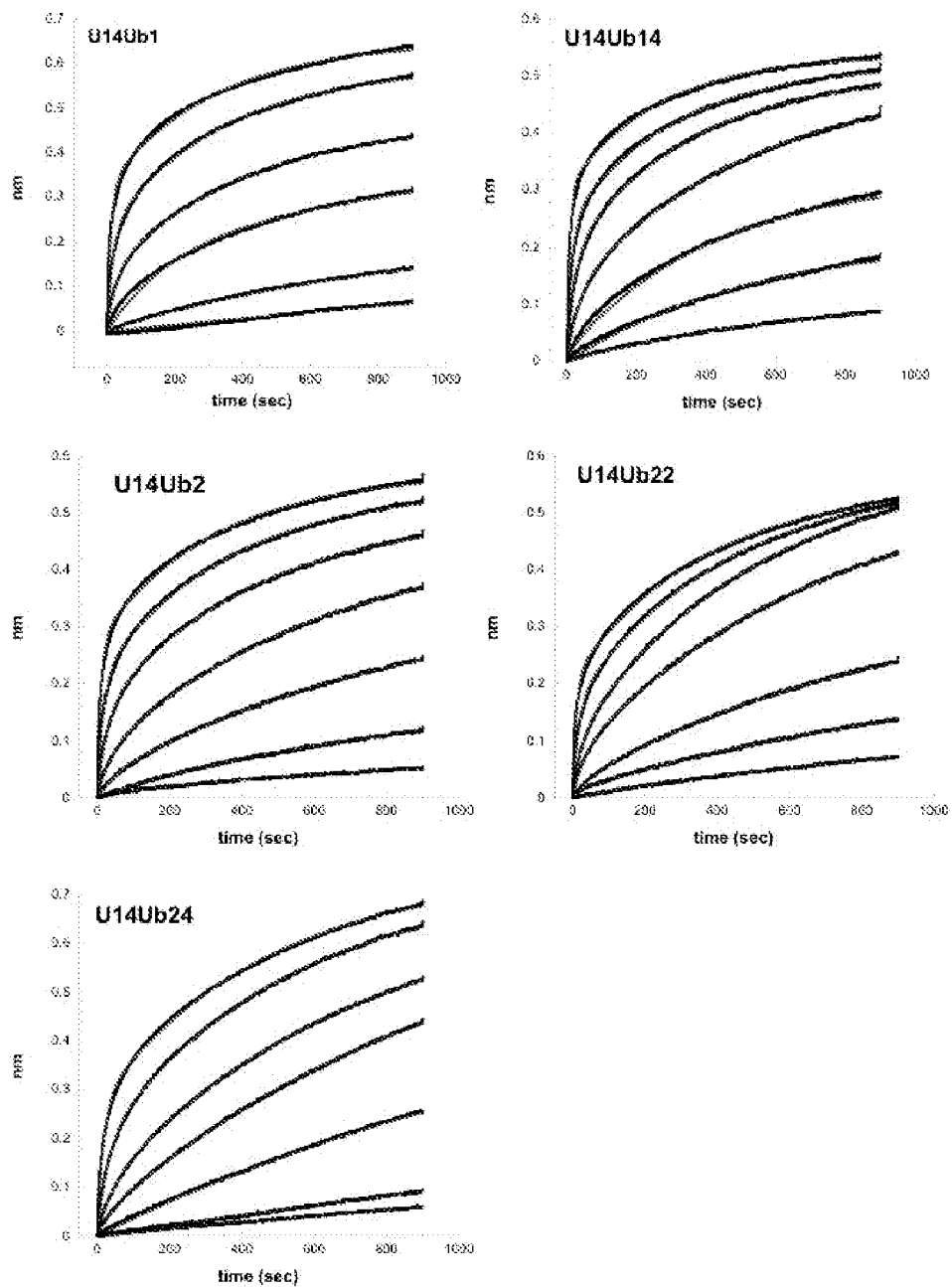
FIG. 28 depicts Biolayer Interferometry titrations fit to a biphasic association model. Titrations of USP14 with the U14Ubs detected by biolayer interferometry (black) fit well to a biphasic association model (red). The concentrations of the U14Ubs used in the assay are 0.068, 0.206, 0.618, 1.85, 5.17, 16.7 and 50 µM.
Figure 29:
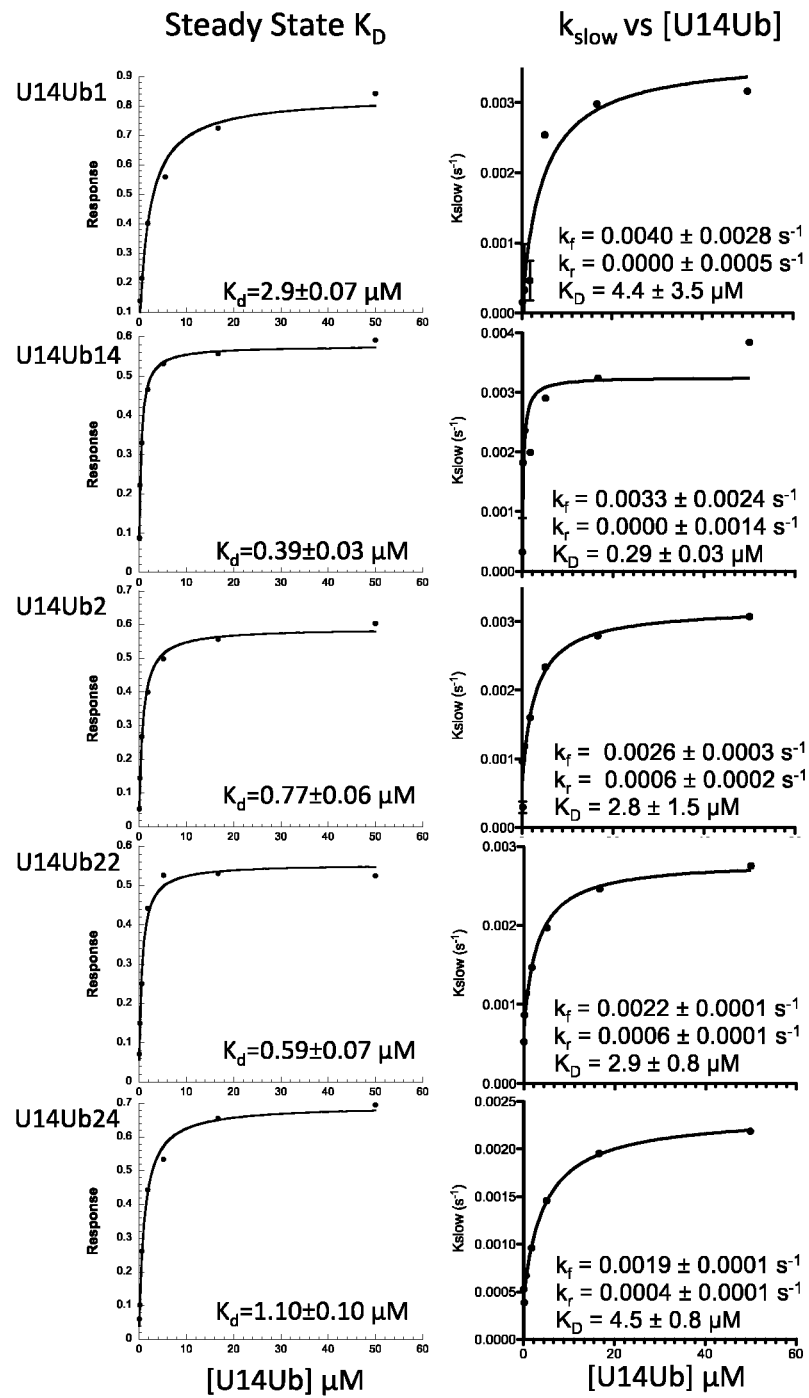
FIG. 29 depicts Equilibrium $K_D$ from Steady State Response and plots of $k_{slow}$ vs. the concentration of U14Ub with induced-fit model fits. The slow phase of the association fits well to the induced-fit model outlined by Hammes, et al., Proc. Natl. Acad. Sci. U.S.A. 106, 13737-13741 (2009).

Selecting for USP14-binding ubiquitin variants (U14Ubs) yielded several strong sequence preferences, such as the nearly invariant incorporation of a glycine at position 7 (FIG. 18A). Over forty U14Ubs (designated U14UbXX, where XX denotes the clone number) were cloned, expressed, purified, and screened for their ability to bind USP14, UCHL1, and UCHL3 via ELISA and/or biolayer interferometry. The analysis was focused on the five clones with the highest apparent affinity for USP14: U14Ub1, 2, 14, 22, and 24 (FIG. 18B). Thermal stability measurements show that the U14Ubs are not significantly destabilized with respect to wild-type (FIG. 27). ELISA and biolayer interferometry titrations of these ubiquitin variants reveal that each binds USP14 with 100-500-fold improved affinity compared to wild-type ubiquitin (FIG. 18B). Conversely, each variant binds UCHL1 and UCHL3 with 40-2,000 fold weaker affinity than wild-type (FIG. 18B; Table 14). Close inspection of titrations of USP14 with the U14Ubs initially revealed that single-parameter fitting of the association kinetics is insufficient to explain the data. Instead, biphasic association was observed, with a dependence of the slower rate on the concentration of U14Ub indicative of an induced fit mechanism of binding (FIGS. 18C and 28-29).[40]

If the U14Ubs were to bind USP14 via a conformational selection mechanism, it would be expected that the population of the U14Ub state competent for USP14 binding would be enriched relative to wild-type; at its most extreme this could result in a change in the ground-state structure of the U14Ubs. However, if the U14Ubs were to bind USP14 via an induced-fit mechanism, it would be expected that the transition between the U14Ub-USP14 encounter complex and the fully-bound state has become more favorable. The conformational selection and induced-fit binding models represent two extremes of a single reaction cycle,[40] therefore, any perturbation disfavoring one arm of the pathway would favor the other. As both binding mechanisms seem to play a role in wild-type ubiquitin binding interactions,[29-30] the observation of binding kinetics consistent with a binding mechanism dominated by induced-fit may be linked to a perturbation in the transitions between substates in the apo U14Ub conformational ensemble.

Figure 35:
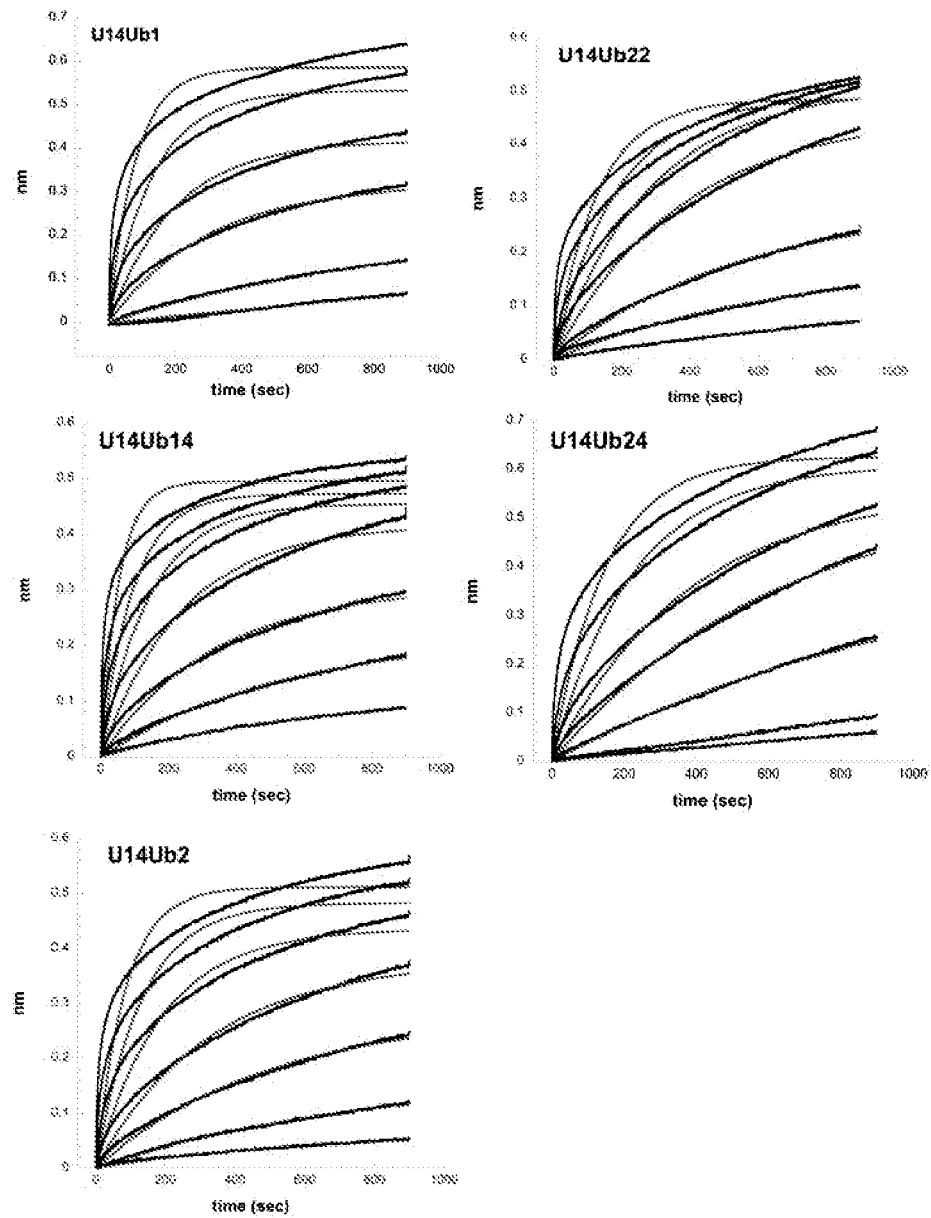
FIG. 35 depicts Biolayer Interferometry titrations (black) do not fit to a single-phase disassociation model (red). The concentrations of the U14Ubs used in the assay are 0.068, 0.206, 0.618, 1.85, 5.17, 16.7 and 50 µM.
Figure 36:
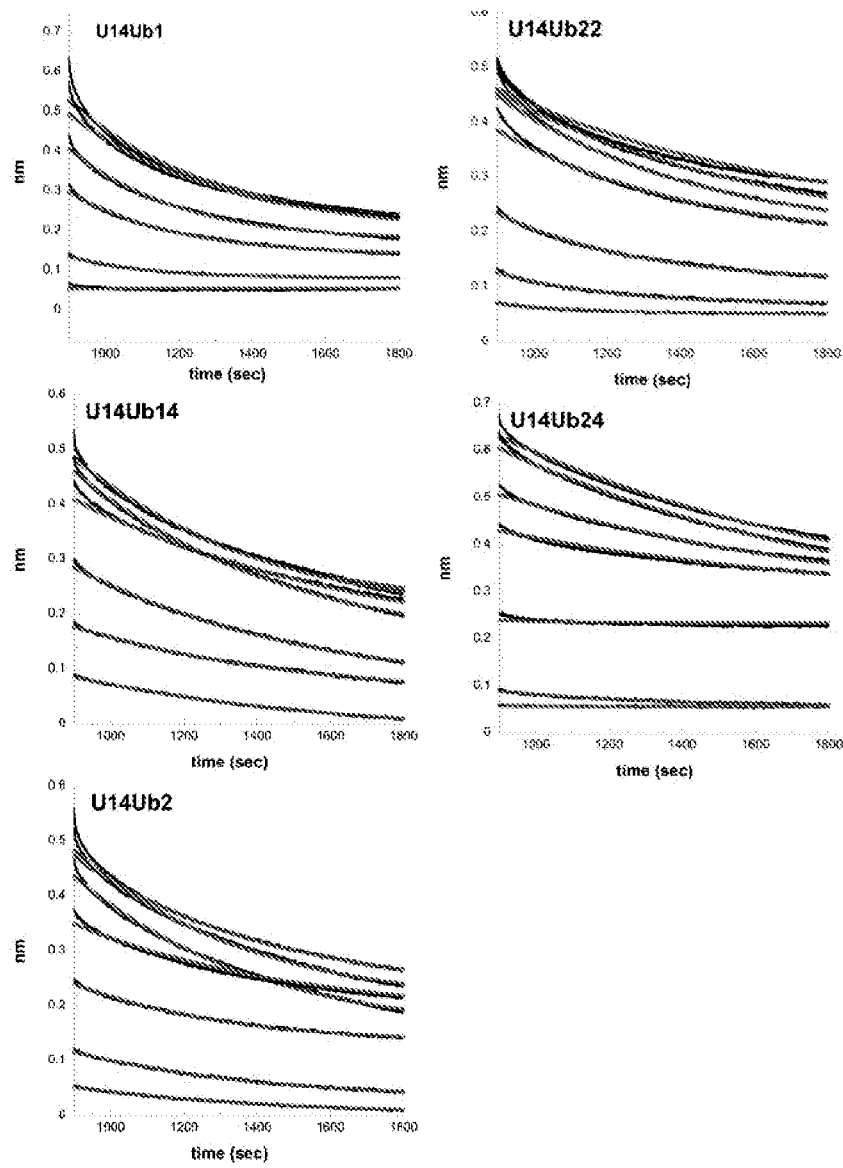
FIG. 36 depicts Biolayer Interferometry titrations (black) fit to a single-phase disassociation model (red). The concentrations of the U14Ubs used in the assay are 0.068, 0.206, 0.618, 1.85, 5.17, 16.7 and 50 µM.

Further inspection of titrations of USP14 with the U14Ubs detected by biolayer interferometry did not fit to a single-phase association model over a 1,000 second measurement (FIG. 35). However, when the measurement time was extended to 1,800 seconds, titrations of USP14 with the U14Ubs detected by biolayer interferometry were then found to fit reasonably well to a single-phase disassociation model (FIG. 36). There is a small deviation from idealized behavior at early time points and higher concentrations of the U14Ubs that is, without being bound to theory, likely linked to the induced fit nature of the U14Ub-USP14 binding event. However, these data were not fit to a biphasic disassociation model due to the limited data available to sufficiently sample the faster phase.

This example demonstrates that the technique of Conformational Display can successfully identify a conformationally stabilized ubiquitin variant that binds to USP14 with 100-500-fold improved affinity compared to wild-type ubiquitin. This ubiquitin variant exhibits binding kinetics consistent with an induced-fit mechanism with respect to USP14.

TABLE 14

Equilibrium and kinetic parameters for the association of Usp14 with U14Ubs. Kinetic parameters were determined from the titration data as discussed in the methods.

|  | U14Ub1 | U14Ub14 | U14Ub2 | U14Ub22 | U14Ub24 |
|---|---|---|---|---|---|
| K$_d$(steady state) μM | 2.90 ± 0.07 | 0.39 ± 0.03 | 0.77 ± 0.06 | 0.59 ± 0.07 | 1.1 ± 0.1 |
| k$_{on}^a$ (1/M*s) | (4.0 ± 2.8) × 10$^3$ | (5.0 ± 3.1) × 10$^3$ | (4.2 ± 2.6) × 10$^3$ | (4.3 ± 2.8) × 10$^3$ | (2.7 ± 2.0) × 10$^3$ |
| k$_{off}^a$ (1/s) | (3.7 ± 0.01) × 10$^{-3}$ | (2.0 ± 0.2) × 10$^{-3}$ | (2.2 ± 0.3) × 10$^{-3}$ | (2.5 ± 0.1) × 10$^{-3}$ | (1.5 ± 0.1) × 10$^{-3}$ |
| K$_D^a$ (kinetic) μM | 1.3 ± 0.9 | 0.5 ± 0.3 | 0.7 ± 0.5 | 0.7 ± 0.4 | 0.8 ± 0.5 |
| k$_f$(1/s) | (3.7 ± 0.6) × 10$^{-3}$ | (3.3 ± 2.4) × 10$^{-3}$ | (2.6 ± 0.3) × 10$^{-3}$ | (2.2 ± 0.1) × 10$^{-3}$ | (1.9 ± 0.1) × 10$^{-3}$ |
| k$_r$(1/s) | (0.0 ± 0.5) × 10$^{-3}$ | (0.0 ± 1.4) × 10$^{-3}$ | (0.6 ± 0.2) × 10$^{-3}$ | (0.6 ± 0.1) × 10$^{-3}$ | (0.4 ± 0.1) × 10$^{-3}$ |
| K$_D$(induced fit) μM | 4.4 ± 3.5 | 0.29 ± 0.31 | 2.8 ± 1.5 | 2.9 ± 0.8 | 4.5 ± 0.8 |

[a]Kinetic fits were averaged together for the highest three concentration, reported errors are the standard deviation of the values for the three highest concentrations.

Example 8

Crystal Structure of U14Ub2

This example investigates the connection between the shift towards an induced fit binding mechanism and the structure and dynamics of apo U14Ubs.
Materials and Methods
X-Ray Crystallography and Structure Determination
U14Ub2 for crystallography was purified as above passed with the final gel filtration step performed in 25 mM HEPES pH 7.2 with 100 mM NaCl. The final pool was concentrated to 15 mg/mL and frozen at −80° C. U14Ub2 was crystallized at 19° C. in hanging drops, consisting of a 1:1 ratio of protein (15 mg/mL) to mother liquor, suspended over mother liquor (0.1 M MES pH 6.1, 1% 2-Methyl-2,4-pentanediol, and 3.5 M ammonium sulfate). Crystals appeared after 2 days and grew to full size after 1 week. For data collection crystals were transferred to fresh mother liquor and then flash frozen in liquid nitrogen. The crystals diffracted to 2.54 Å, and belong to space group $P2_1$ with 8 molecules in the asymmetric unit. A single ubiquitin chain (PDB code: 1UBQ) was used as a search model for molecular replacement. Crystallographic statistics are presented in Table 15.

TABLE 15

Crystallographic statistics

| Data Collection | |
|---|---|
| Resolution (Å)[a] | 50.73-2.54 (2.631-2.54) |
| Space group | P 1 21 1 |
| Unit cell | a = 50.73, b = 55.45, c = 94.28 β = 89.99 |
| Total reflections | 60870 (509) |
| Unique reflections | 17488 (144) |
| Multiplicity | 3.5 (3.5) |
| Completeness (%) | 99.93 (100.00) |
| Mean I/sigma(I) | 7.13 (2.12) |
| Wilson B-factor | 28 |
| R-sym[b] | 0.207 (0.341) |
| Refinement | |
| R-factor/R-free[c] | 0.2668/0.2997 |
| Number of atoms | 4541 |
| Water | 47 |
| Protein residues | 568 |
| RMS(bonds) | 0.005 |
| RMS(angles) | 0.76 |
| Ramachandran favored (%) | 99 |
| Ramachandran outliers (%) | 0 |
| Average B-factor | 46.4 |

Figure 19:
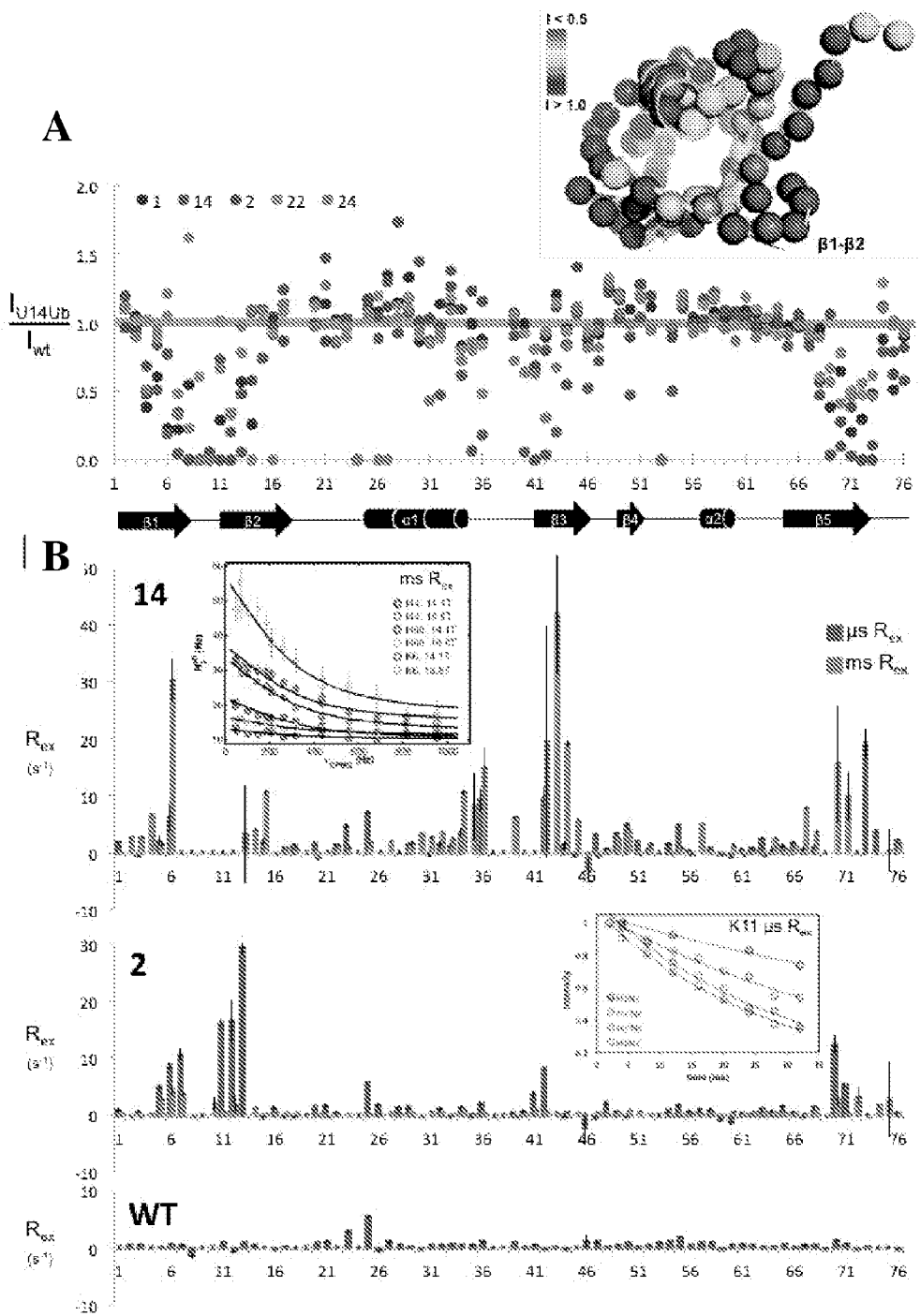
FIG. 19 depicts U14Ub apo dynamics are slowed relative to wild-type. A) Ratios of the intensities of amide resonances in $^1$H-$^{15}$N HSQC spectra of U14Ubs versus wild-type. The ratios were normalized to resonances that showed no exchange. The inset shows these ratios plotted onto the structure of wild-type ubiquitin (PDB code 1ubi); the most significant changes occur in the β1-β2 region. B) Millisecond (blue) and microsecond (red) motions quantified by $R_{ex}$ measurements for U14Ub14, U14Ub2 and wild-type ubiquitin. Insets in the U14Ub14 and U14Ub2 plots display examples of the raw data for the ms and μs $R_{ex}$ measurement, respectively. Resonances lacking data due to exchange broadening or spectral overlap are denoted with an X. Wild-type ubiquitin shows no ms $R_{ex}$ at these conditions.
Figure 24:
FIG. 24 depicts CS-Rosetta models of all five U14Ubs. CS-Rosetta models of all five U14Ubs (ribbons) overlaid with CS-Rosetta models of wild-type ubiquitin (cartoon). The two lowest energy models for each variant are shown. U14Ubs are colored according to the scheme in FIG. 19: 1 in purple, 2 in blue, 14 in red, 22 in orange, and 24 in green. The fold for each variant is indistinguishable from wild-type ubiquitin.
Figure 31:
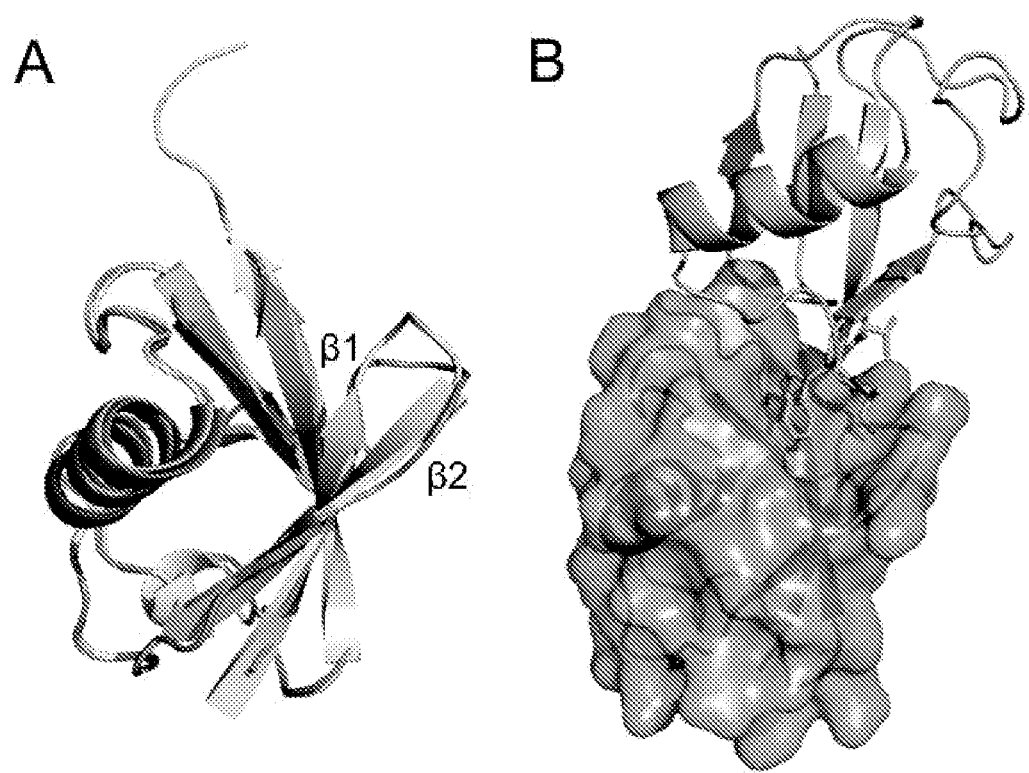
FIG. 31 depicts the Crystal Structure of U14Ub2. A) Overlay of U14Ub2 (blue) with wild-type ubiquitin (wheat, PDB code: 1UBI). The overall fold of U14Ub2 is the same as wild-type, with deviations in the β1-β2 region likely due to crystal packing. B) Tryptophan 71 packs into the hydrophobic core of the adjacent molecule in the asymmetric unit, distorting the conformation of β1-β2. The structure of U14Ub2 is shown as the surface representation in the same orientation as in panel A. The adjacent molecule in the asymmetric unit is shown in salmon.

Results
The crystal structure of U14Ub2 was solved and the backbone NMR resonances of all five U14Ubs were assigned. Both the crystal structure and NMR-derived CS-Rosetta models[41] indicate that the ground state fold of each of the variants is indistinguishable from wild-type (FIGS. 24 and 31). However, in the $^1H/^{15}N$ HSQC spectra of all of the U14Ubs, many of the backbone amide resonances are broadened relative to wild-type (FIG. 19A). The broadened residues are spatially clustered around the β1-β2 loop and in the neighboring β3 and β5 strands, signifying a modulation of conformational dynamics in these regions. Conversely, the $\{^1H\}$-$^{15}N$ heteronuclear NOE remains largely unchanged, indicating that fast, sub-nanosecond motions are unperturbed.[42]

Taken together with the observation that the β1-β2 region of wild-type ubiquitin is mobile on the sub-50 μs timescale,[28] the observed line broadening in this example indicates a slowing of large scale conformational dynamics in this region of the apo U14Ubs without a change in small scale fast motions.

Example 9

Figure 23:
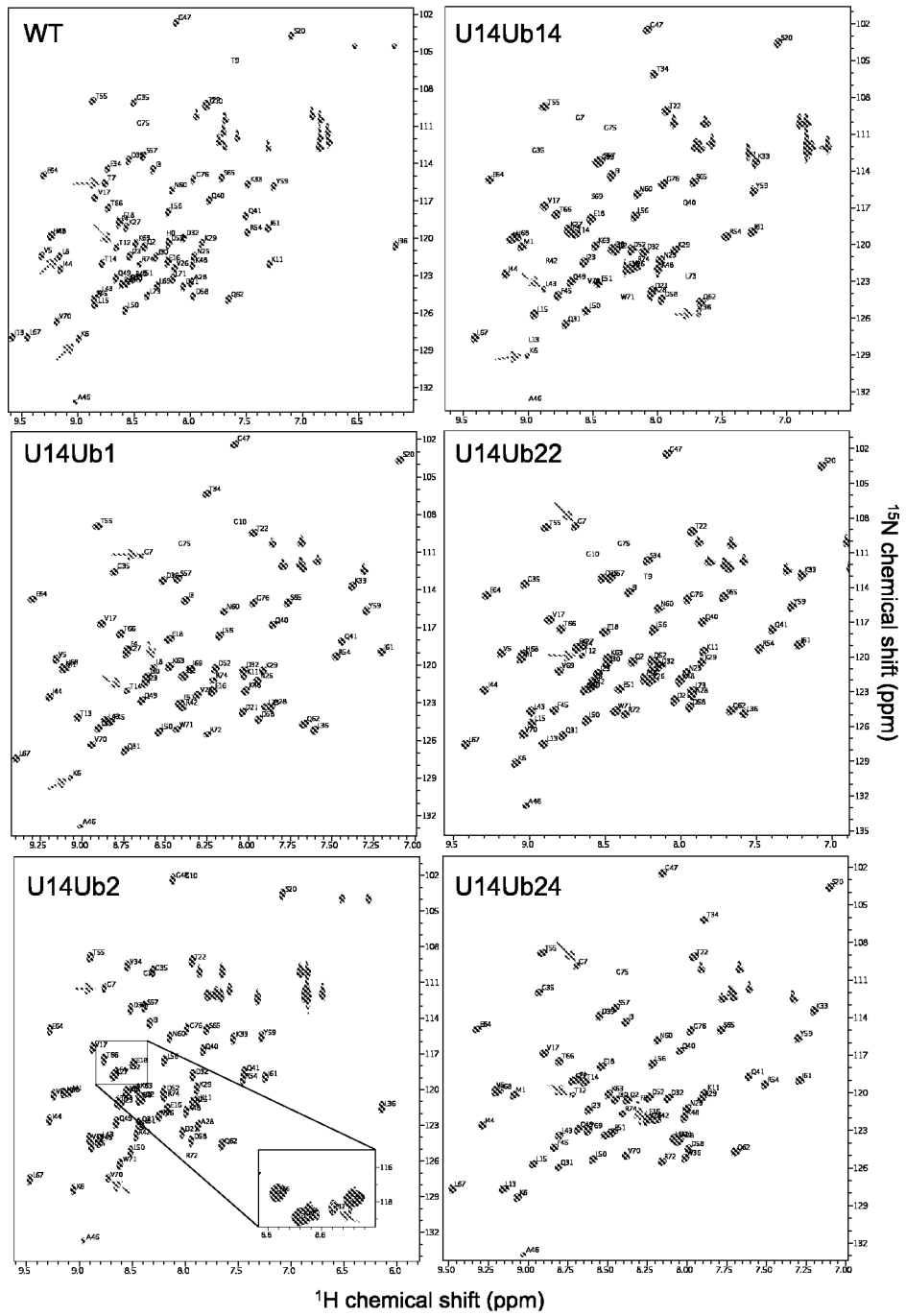
FIG. 23 depicts assigned $^1$H-$^{15}$N HSQC spectra of the five U14Ubs and wild-type ubiquitin. Selected residues around the β1-β2 region showing significant exchange broadening are highlighted. U14Ub14 shows the most severe exchange broadening, consistent with it having the largest values for ms $R_{ex}$.

Conformational Dynamics of the β1-β2 Region in Conformationally Stabilized Ubiquitin Variants This example utilizes $R_2$ dispersion experiments to examine whether the β1-β2 structural motif in conformationally stabilized ubiquitin proteins exhibit slower dynamics in comparison to the motion observable in this region in wildtype ubiquitin.
Materials and Methods
NMR Spectroscopy
Resonance assignments for wild-type ubiquitin and the U14Ubs were obtained from semi-automated analysis of peak positions in $^1H$-$^{15}N$ HSQC, HNCA, HNCACB and HNcoCA spectra using PINE (Bahrami et al., *PLoS Comput. Biol.* 5, e1000307 (2009)). Chemical shifts were referenced to trimethylsilylpropionate. Nearly complete backbone assignments were obtained for wild-type ubiquitin and the U14Ubs. The amide resonances of E24 and G53 are unobserved in all proteins. As discussed below and depicted in FIG. 19 and FIG. 23, all of U14Ubs show broadening of NMR resonances due to chemical exchange. This is most noticeable in U14Ub14, which required triple resonance experiments conducted at higher temperatures to establish connectivities between residues. In summary, in addition to residues 24 and 53 for all proteins, residues 9 and 12 are unobserved for U14Ub1; residues 9 and 73 are unobserved for U14Ub2; residues 8-12, 41 and 72 are unobserved for U14Ub14; and residues 9 and 10 are unobserved for U14Ub24. Along with the amino-acid sequence, $^1H$, $^{15}N$, $^{13}C\alpha$ and $^{13}C\beta$ chemical shifts were used as inputs for the generation of CS-Rosetta models (Shen, et al. *Proc. Natl. Acad. Sci. U.S.A.* 105, 4685-4690 (2008)). For each U14Ub the lowest energy CS-Rosetta model converged to a single fold that was indistinguishable from wild-type (FIG. 24). All NMR data sets were collected at 18.8 T on a Bruker DRX spectrometer or at 14.1 T on a Bruker Avance III spectrometer. NMR experiments were conducted at 24° C., calibrated to deuterated methanol (Findeisen, et al., *Magn Reson Chem* 45, 175-178 (2007)).

The $\{^1H\}$-$^{15}N$ heteronuclear NOE values were determined according to the method of Grzesiek and Bax (Grzesiek & Bax, *J. Am. Chem. Soc.* 115, 12593-12594 (1993)). The recycle delay in all experiments and $^1H$ irradiation time were set to 5s and 1s, respectively. Microsecond $R_{ex}$ values were extracted from $H_zN_z$, $H_zN_z'$, $H_z'N_z'$, and $H_zN_z R_{1\rho}$ measurements where the prime denotes the presence of a spin-lock field during the relaxation delay (Hansen, et al., *J. Am. Chem. Soc.* 129, 11468-11479 (2007); Hansen et al., *J. Am. Chem. Soc.* 131, 16257-16265 (2009)). The spin lock fields employed were 10 kHz and 2 kHz on the $^1H$ and $^{15}N$ frequencies, respectively. Delay times were between 2 ms and 32 ms for all experiments with spin lock irradiation and 4 and 128 ms for $H_zN_z$, recorded in the absence of irradiation. Each of these experiments was recorded as a pseudo-3D with 64 complex $^{15}N$ points in each plane and nine relaxation delay times recorded in an interleaved fashion to alleviate potential artifacts due to differential sample heating. Evolution curves were fit using nmrPipe (Delaglio, et al., *J Biomol NMR* 6, 277-293 (1995)) and data analysis was conducted according to Hansen et al. (*J. Am. Chem. Soc.* 131, 16257-16265 (2009)).

Figure 25:
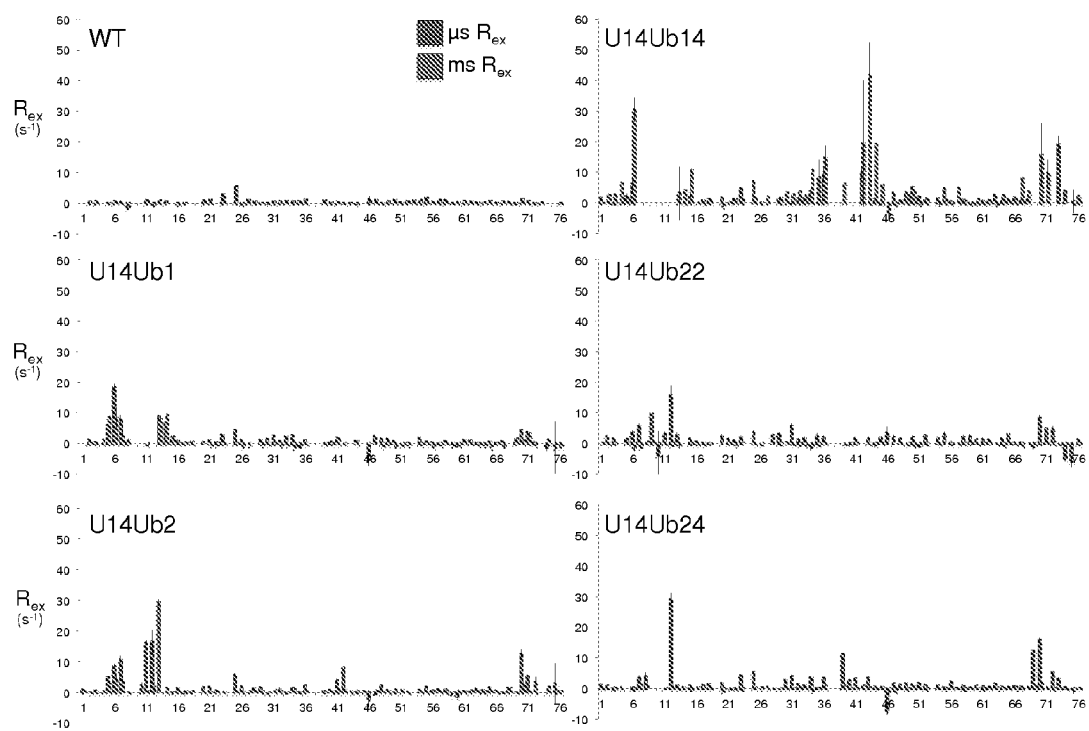
FIG. 25 depicts microsecond and millisecond $R_{ex}$ values for all variants. $R_{ex}$ values were measured at 18.8 T and 297K. Millisecond $R_{ex}$ is estimated for each residue by the difference between $R_{2obs}$ at CPMG fields of 50 and 950 Hz.
Figure 26:
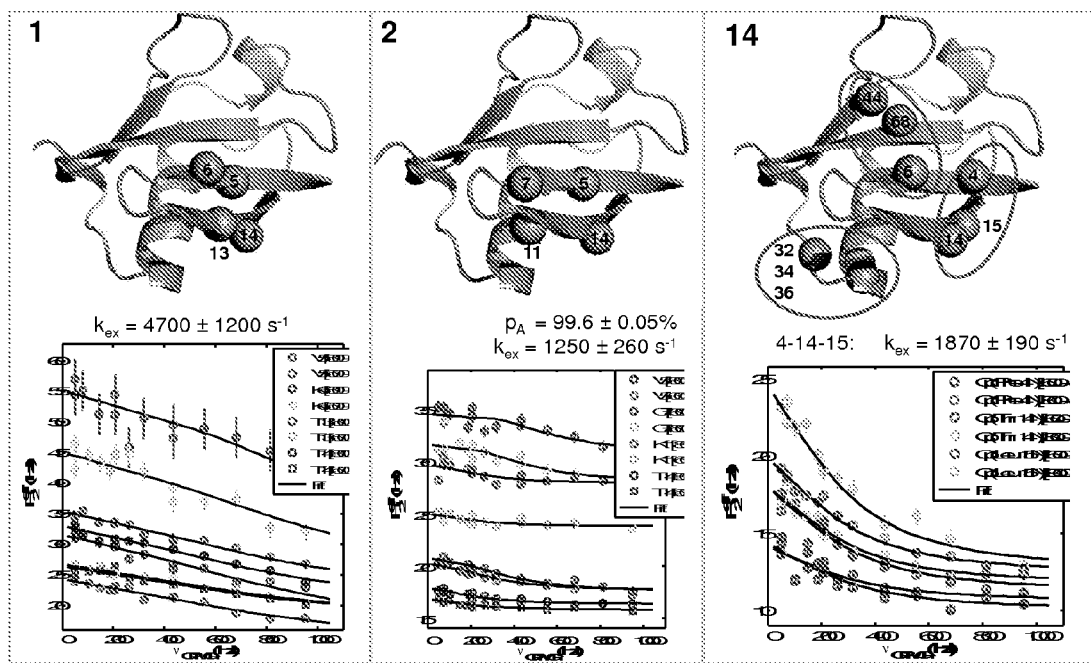
FIG. 26 depicts group fits of $R_2$ dispersion data at two fields. Residues that show $R_2$ dispersion that are not too noisy to fit are shown as orange spheres mapped onto the crystal structure of wild-type ubiquitin for U14Ub1, U14Ub2 and U14Ub14. Residues displaying significant ms $R_{ex}$ values cluster together in the structure. Fits to the Carver Richards equations were obtained globally for all residues highlighted for U14Ub1 and U14Ub2. The three clusters of residues highlighted for U14Ub14 were fit both as independent groups due to their spatial separation and also globally, yielding similar values for $k_{ex}$. The fit for U14Ub14 shown here is for the cluster of residues 4, 14 and 15.

$R_2$ dispersion data sets were collected according to the methodology of Tollinger et al. (*J. Am. Chem. Soc.* 123, 11341-11352 (2001)) with $R_{2obs}$ determined from 2-point fits in order to more fully sample the dispersion curve (Mulder, et al., *J. Am. Chem. Soc.* 123, 967-975 (2001)). Data sets were collected as interleaved pseudo-3Ds with 64 complex $^{15}N$ points in each plane and ca. 15 CPMG frequencies. CPMG frequencies sampled were between 50 and 950 Hz with two frequencies repeated for error analysis. Plots of ms $R_{ex}$ versus sequence described in the results and in FIG. 25 are estimates derived from the difference in $R_{2obs}$ determined at CPMG frequencies of 50 and 950 Hz. $R_2$ dispersion curves were collected for all U14Ubs at 18.8 T and 14.1 T. U14Ub1, 2 and 14 had sufficient dispersion to be fit to the Carver-Richards equation (Richards & Carver, *Journal of Magnetic Resonance* (1972)), implemented via the GUARDD program (Kleckner & Foster, *J Biomol NMR* 52, 11-22 (2012)) within MATLAB. Dispersion data was fit to groups of residues that physically cluster and show similar exchange behavior (FIG. 26). All of the U14Ubs except U14Ub2 are in the fast exchange regime; therefore, the populations and chemical shift differences between states are not separable. The exchange rates determined for U14Ub1, U14Ub2, and U14Ub14 are 4700±1200 s$^{-1}$, 1250±260 s$^{-1}$, and 1870±190 s$^{-1}$, respectively. The population of the ground state of U14Ub2 is 99.6±0.05%. $R_2$ dispersion was explored at lower temperatures, but data sets were generally not amenable to analysis due to increased broadening in the region of interest Results To confirm that the stabilized ubiquitin variants exhibit a slowing of large scale conformational dynamics in the β1-β2 region and to provide deeper insight into the nature of these motions, $R_2$ dispersion experiments, sensitive to motions on millisecond timescales (ms $R_{ex}$),[42] were performed as well as $H_zN_z$ $R_{1\rho}R_{ex}$ measurements,[43] which probe the dynamics of backbone amides on the microsecond timescale (μs $R_{ex}$). In these measurements higher $R_{ex}$ values imply slower conformational exchange of a mobile segment on the timescale probed by the experiment. Although the motions present in wild-type ubiquitin are largely too fast to observe by ms $R_{ex}$,[44] several of the U14Ubs show significant $R_2$ dispersion (ms $R_{ex}$) at room temperature, most dramatically in U14Ub14 (FIG. 19B). The $R_2$ dispersion data fits well to a two-site exchange model;[42] however, most of the U14Ubs are in the fast exchange limit, meaning that populations of the excited state are inseparable from the chemical shift changes. The exception is U14Ub2, which could be fit with a sparsely populated excited state (0.4±0.05%). The μs $R_{ex}$ values in the regions surrounding the β1-β2 loop in tertiary structure are up to forty-fold higher in the U14Ubs than the corresponding positions in wild-type, most notably in U14Ub2 (FIG. 19B).

This example demonstrates that, while the motion of wild-type ubiquitin is so fast as to require a complex RDC-based analysis to observe,[28] the dynamics of U14Ubs are dominated by much slower μs-ms timescales. As the motion in the apo U14Ubs has slowed relative to wildtype, it follows that the energy barrier between substates has increased. It can be hypothesized, without being bound to theory, that this has reduced the flux through the conformational selection arm of the pathway resulting in a binding mechanism dominated by induced fit.

Example 10

Incorporation of U14Ub into Polyubiquitin Chains

Figure 20:
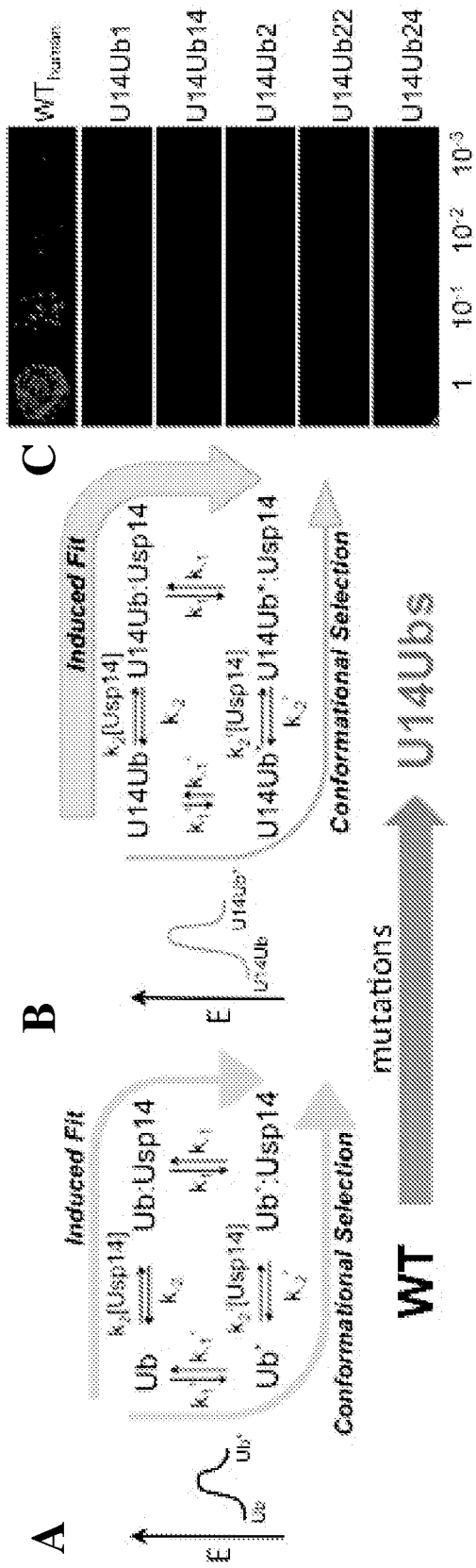
FIG. 20 depicts perturbation of the energy landscape of ubiquitin affects the mechanism of USP14 binding and results in ubiquitin variants that cannot support growth in vivo. A) Ubiquitin binding can occur through either conformational selection or induced fit. The interconversion between conformational substates of wild-type ubiquitin is fast, therefore the energy barrier separating substates is modest. B) The motions of the U14Ubs are much slower than wild-type, reducing the flux through the conformational selection arm of the pathway and causing the binding mechanism to be dominated by induced fit. C) Despite their ability to be ligated into Lys48-linked chains, unlike human ubiquitin, the U14Ubs cannot replace endogenous ubiquitin in yeast.

Taken together, the data of the previous examples indicate that the U14Ubs achieve affinity changes by modulating the conformational dynamics of the apo state rather than the ground state structure. The mutations, designed to stabilize the USP-binding "down" conformation, have resulted in an increase in the energy barrier between the conformational substates, thereby driving the U14Ub-USP14 interaction through the induced-fit arm of the reaction cycle (FIG. 20A-B). The experiments in this example seek to determine whether the slowed conformational dynamics in the U14Ubs had consequences for other aspects of ubiquitin processing. Accordingly, their ability to be assembled into chains was examined.

Materials and Methods

U14Ub Transformation and Growth in Yeast

SUB328 (MATa lys2-801 leu2-3, 2-112 ura3-52 his3-Δ200 trp1-1 ubil-Δ1::TRP1 ubi3-Δ2::URA3 ubi3Δub-2 ubi5-Δ2::LEU2) competent yeast cells containing pUB146 URA3-marked plasmid expressing wild-type ubiquitin on a galactose-regulated promoter (Spence, et al., *Mol. Cell. Biol.* 15, 1265-1273 (1995)) were grown in YPDRafGal at 30° C. and prepared using Zymo Research Frozen-EZ Yeast Transformation Kit II. Each U14Ub and wild-type ubiquitin was cloned into Yep96 TRP1-marked plasmid on a copper inducible promoter (Hanna & Finley, *Mol. Cell. Biol.* 23, 9251-9261 (2003)) using BglII/Kpn1 restriction sites. 400 ng of each plasmid was incubated with the competent cells and transformed per kit protocol. Cells were pelleted and resuspended in YPDRafGal media before being serially diluted and drop plated onto YEPD+5'FOA plates for selection of Yep96 expressing plasmid. Plates were incubated at 30° C. for 3 days and imaged.

Ub14 Chain Polymerization

Figure 32:
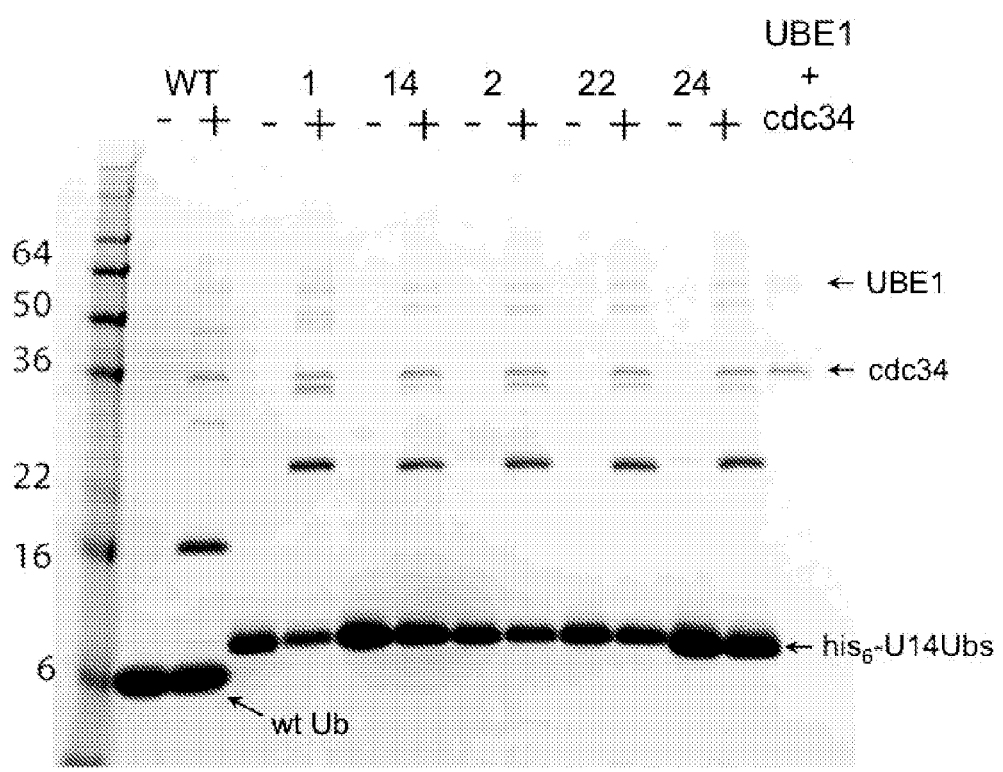
FIG. 32 depicts incorporation into K48-linked chains. SDS-Page of U14Ub variants showing incorporation into K48-linked chains to a similar extent as wild-type by UBE1 and cdc34. The weight discrepancy between the U14Ubs and wild-type ubiquitin is due to the presence of the 6xHis tag (SEQ ID NO: 2), which has not been cleaved from the mutants.

Ubiquitin chain polymerization was performed as described previously (Dong, et al., *Structure* 19, 1053-1063 (2011) in 100 mM Tris (pH 8), 20 mM ATP, 20 mM MgCl$_2$, and 1.2 mM DTT. Each reaction contained 30 μM ubiquitin or variant, 125 nM UBE1, and 1.25 μM Cdc34. Reactions were allowed to proceed for 20 hours at 37° C., followed by quenching in reducing SDS loading buffer and visualization via 18% tris-glycine SDS-PAGE Results The U14UBs are assembled into Lys48-linked chains by UBE1 and Cdc34 to a similar extent as wild-type ubiquitin (FIG. 32), suggesting that the mutations around β1-β2 may influence DUB interactions without globally disrupting ubiquitin signaling. Intriguingly, the U14Ubs are not capable of supporting in vivo growth in yeast despite being able to be processed into Lys48-linked chains, the only chain linkage required for growth[45] (FIG. 20C).

This example reveals for the first time how perturbation of a conformational energy landscape can have drastic consequences in vivo. Hence, the exquisitely tuned conformational plasticity of ubiquitin, required to maintain its ability to interact with a diverse group of binding partners, is inextricably linked to its profound conservation in eukaryotes.

Conclusions

In sum, while phage display, coupled with random or targeted mutagenesis, is an effective technique to select for surface mutations that improve the affinity between a scaffold and a target of interest, these approaches usually neglect the influence of dynamics and conformational change upon protein-protein interactions, though they may serendipitously take advantage of dynamics to select for conformation-specific effects.[18] Methods have recently been described that use small molecules to "lock" a flexible target into one a given state, allowing the engineering of antibodies that bind a certain conformation. However, this pre-supposes the existence of chemical tools to influence a protein's conformational equilibrium.[1-2] It is believed that these studies represent the first instance where sequence diversity methods are used to purposefully discover sequences that favor a desired conformation.

By mutagenizing a protein's core and selecting for high affinity interactions, Conformational Display implicitly favors a reduction in entropy of the target's apo state. Since macromolecular associations often freeze out a particular conformation, a reduction in entropy of the apo state leads to a smaller entropic penalty upon complex formation. This is evident from the preponderance of intramolecularly disulfide-bonded U7Ub clones discovered the initial panning (FIG. 1B). Notably, disulfide stabilization is reminiscent of a strategy commonly used in in medicinal chemistry, where small molecules with flexible torsions are made more rigid by the addition of bulky groups, unsaturation, or cyclization.[19] Since proteins typically have many more degrees of freedom than small molecules, and the determinants of their backbone flexibility are less well-determined, Conformational Display efficiently screens many sequences to find combinations of buried amino acids that reduce flexibility to promote high affinity interactions.

Additionally, functional conformations of ubiquitin that govern its interaction with therapeutically relevant USP- and UCH-type deubiquitinases have been identified and the energy landscape connecting these states to increase affinity for USP14 and decrease affinity for other DUBs has been modulated. It is believed that these represent the first gain-of-function mutations to affect conformational motion at a protein interface.

Example 11

Second Generation Affinity Maturation for U7Ub25

The apo structure of U7Ub7 suggested that the C-terminal region might be involved in binding to USP7 by surface interaction. Accordingly, further maturation of surface residues was performed in this region.

Materials and Methods

Affinity maturation and spot phage ELISA were performed as described above. The second generation affinity maturation library was designed by combining soft randomizing (~50% mutation rate at each amino acid) surface residues Q40, R42, A46, G47, Q49, Q62, E64, S65, T66, H68, V70 and R72 using a doping codon and hard randomizing C-terminus residues of R72-G76 using NNK codon. A stop template (single strand DNA of p8U7Ub25 containing two stop codons in the regions of 34-36 and 69-76) was used to construct a library that contained $\sim 2 \times 10^{10}$ unique members. The library was cycled against USP7catC223A for 4 rounds and 61 unique binders were identified.

Results

Figure 34:
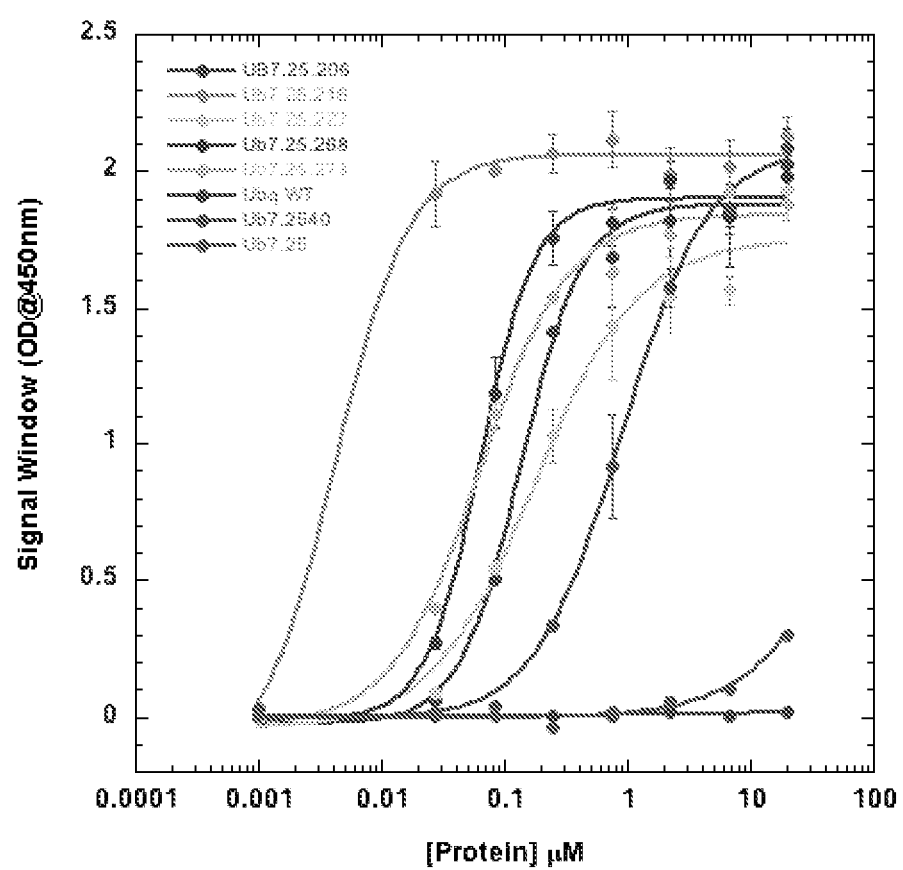
FIG. 34 depicts affinity ranking of U7Ub25 affinity matured variants by ELISA.

Ten clones showed IC50 in 20 nM range by a spot phage competition ELISA (data not shown) and were selected for further characterization (FIG. 33). Five of 10 clones were expressed and purified as proteins and the affinity were ranked using a ELISA, in which serial dilution of his-tagged U7Ubs were applied to plate immobilized with USP7catC223A and the bound U7Ubs were detected with anti-His-HRP. As shown in FIG. 34, comparing to U7Ub25.2540, the first generation of affinity matured U7Ub25, all second generation U7Ub25 variants showed improved binding affinity. The strongest binder, U7Ub25.216 appeared to have ~100 folds affinity improvement in comparison to U7Ub25.2540.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

REFERENCES

1. Rizk, S. S. et al. Allosteric control of ligand-binding affinity using engineered conformation-specific effector proteins. *Nat Struct Mol Biol* (2011).doi:10.1038/nsmb.2002
2. Gao, J., Sidhu, S. S. & Wells, J. A. Two-state selection of conformation-specific antibodies. *Proc Nati Acad Sci USA* 106, 3071-3076 (2009).
3. Lange, O. F. et al. Recognition dynamics up to microseconds revealed from an RDC-derived ubiquitin ensemble in solution. *Science* 320, 1471-1475 (2008).
4. Clague, M. J. & Urbé, S. Ubiquitin: same molecule, different degradation pathways. *Cell* 143, 682-685 (2010).
5. Pickart, C. M. Mechanisms underlying ubiquitination. *Annu Rev Biochem* 70, 503-533 (2001).
6. Pickart, C. M. & Fushman, D. Polyubiquitin chains: polymeric protein signals. *Curr Opin Chem Biol* 8, 610-616 (2004).
7. Komander, D., Clague, M. J. & Urbé, S. Breaking the chains: structure and function of the deubiquitinases. *Nat Rev Mol Cell Biol* 10, 550-563 (2009).
8. Nicholson, B. & Suresh Kumar, K. G. The multifaceted roles of USP7: new therapeutic opportunities. *Cell Biochem Biophys* 60, 61-68 (2011).
9. Hussain, S., Zhang, Y. & Galardy, P. J. DUBs and cancer: the role of deubiquitinating enzymes as oncogenes, non-oncogenes and tumor suppressors. *Cell Cycle* 8, 1688-1697 (2009).
10. Faesen, A. C. et al. Mechanism of USP7/HAUSP Activation by Its C-Terminal Ubiquitin-like Domain and Allosteric Regulation by GMP-Synthetase. *Mol Cell* 44, 147-159 (2011).
11. Fernández-Montalván, A. et al. Biochemical characterization of USP7 reveals post-translational modification sites and structural requirements for substrate processing and subcellular localization. *FEBS J.* 274, 4256-4270 (2007).
12. Humphris, E. L. & Kortemme, T. Design of multi-specificity in protein interfaces. *PLoS Comput Biol* 3, e164 (2007).
13. Friedland, G. D., Lakomek, N.-A., Griesinger, C., Meiler, J. & Kortemme, T. A correspondence between solution-state dynamics of an individual protein and the sequence and conformational diversity of its family. *PLoS Comput Biol* 5, e1000393 (2009).
14. Li, M., Brooks, C. L., Kon, N. & Gu, W. A dynamic role of HAUSP in the p53-Mdm2 pathway. *Mol Cell* 13, 879-886 (2004).
15. Hu, M. et al. Crystal structure of a UBP-family deubiquitinating enzyme in isolation and in complex with ubiquitin aldehyde. *Cell* 111, 1041-1054 (2002).
16. Reyes-Turcu, F. E. et al. The ubiquitin binding domain ZnF UBP recognizes the C-terminal diglycine motif of unanchored ubiquitin. *Cell* 124, 1197-1208 (2006).
17. Yuan, J., Luo, K., Zhang, L., Cheville, J. C. & Lou, Z. USP10 regulates p53 localization and stability by deubiquitinating p53. *Cell* 140, 384-396 (2010).

18. Ganesan, R. et al. Unraveling the allosteric mechanism of serine protease inhibition by an antibody. *Structure* 17, 1614-1624 (2009).
19. *The Practice of Medicinal Chemistry, Second Edition.* 736 (Academic Press: 2003).
20. Hammes, G. G., Benkovic, S. J. & Hammes-Schiffer, S. Flexibility, diversity, and cooperativity: pillars of enzyme catalysis. *Biochemistry* 50, 10422-10430 (2011).
21. Boudreaux, D. A., Maiti, T. K., Davies, C. W. & Das, C. Ubiquitin vinyl methyl ester binding orients the misaligned active site of the ubiquitin hydrolase UCHL1 into productive conformation. *Proc Natl Acad Sci USA* 107, 9117-9122 (2010).
22. Larsen, C. N., Price, J. S. & Wilkinson, K. D. Substrate binding and catalysis by ubiquitin C-terminal hydrolases: identification of two active site residues. *Biochemistry* 35, 6735-6744 (1996).
23. Jeong, H., Mason, S. P., Barabasi, A. L. & Oltvai, Z. N. Lethality and centrality in protein networks. *Nature* 411, 41-42 (2001).
24. Komander, D. The emerging complexity of protein ubiquitination. *Biochem. Soc. Trans.* 37, 937-953 (2009).
25. Ciechanover, A. & Schwartz, A. L. The ubiquitin system: pathogenesis of human diseases and drug targeting. *Biochim. Biophys. Acta* 1695, 3-17 (2004).
26. Shi, D. & Grossman, S. R. Ubiquitin becomes ubiquitous in cancer: emerging roles of ubiquitin ligases and deubiquitinases in tumorigenesis and as therapeutic targets. *Cancer Biol. Ther.* 10, 737-747 (2010).
27. Komander, D., Clague, M. J. & Urbé, S. Breaking the chains: structure and function of the deubiquitinases. *Nat. Rev. Mol. Cell. Biol.* 10, 550-563 (2009).
28. Lange, O. F. et al. Recognition dynamics up to microseconds revealed from an RDC-derived ubiquitin ensemble in solution. *Science* 320, 1471-1475 (2008).
29. Wlodarski, T. & Zagrovic, B. Conformational selection and induced fit mechanism underlie specificity in noncovalent interactions with ubiquitin. *Proc. Natl. Acad. Sci. U.S.A.* 106, 19346-19351 (2009).
30. Long, D. & Brüschweiler, R. In silico elucidation of the recognition dynamics of ubiquitin. *PLoS Comput. Biol.* 7, e1002035 (2011).
31. Cohen, P. & Tcherpakov, M. Will the ubiquitin system furnish as many drug targets as protein kinases? *Cell* 143, 686-693 (2010).
32. Lee, B.-H. et al. Enhancement of proteasome activity by a small-molecule inhibitor of USP14. *Nature* 467, 179-184 (2010).
33. D'Arcy, P. et al. Inhibition of proteasome deubiquitinating activity as a new cancer therapy. *Nat. Med.* 17, 1636-1640 (2011).
34. Ovaa, H. Active-site directed probes to report enzymatic action in the ubiquitin proteasome system. *Nat Rev Cancer* 7, 613-620 (2007).
35. Luchansky, S. J., Lansbury, P. T. & Stein, R. L. Substrate Recognition and Catalysis by UCH-L1. *Biochemistry* 45, 14717-14725 (2006).
36. Renatus, M. et al. Structural Basis of Ubiquitin Recognition by the Deubiquitinating Protease USP2. *Structure* 14, 1293-1302 (2006).
37. Leaver-Fay, A. et al. *Methods in Enzymology.* 487, 545-574 (Elsevier: 2011).
38. Fleishman, S. J. et al. RosettaScripts: A Scripting Language Interface to the Rosetta Macromolecular Modeling Suite. *PLoS ONE* 6, e20161 (2011).
39. Havranek, J. J. & Harbury, P. B. Automated design of specificity in molecular recognition. *Nat. Struct. Biol.* 10, 45-52 (2003).
40. Hammes, G. G., Chang, Y.-C. & Oas, T. G. Conformational selection or induced fit: a flux description of reaction mechanism. *Proc. Natl. Acad. Sci. U.S.A.* 106, 13737-13741 (2009).
41. Shen, Y. et al. Consistent blind protein structure generation from NMR chemical shift data. *Proc. Natl. Acad. Sci. U.S.A.* 105, 4685-4690 (2008).
42. Palmer, A. G., Kroenke, C. D. & Loria, J. P. Nuclear magnetic resonance methods for quantifying microsecond-to-millisecond motions in biological macromolecules. *Meth. Enzymol.* 339, 204-238 (2001).
43. Hansen, D. F., Feng, H., Zhou, Z., Bai, Y. & Kay, L. E. Selective characterization of microsecond motions in proteins by NMR relaxation. *J. Am. Chem. Soc.* 131, 16257-16265 (2009).
44. Massi, F., Grey, M. J. & Palmer, A. G. Microsecond timescale backbone conformational dynamics in ubiquitin studied with NMR R1rho relaxation experiments. *Protein Sci.* 14, 735-742 (2005).
45. Dueber, E. C. et al. Antagonists induce a conformational change in cIAP1 that promotes autoubiquitination. *Science* 334, 376-380 (2011).
46. Tonikian, R., Zhang, Y., Boone, C. & Sidhu, S. S. Identifying specificity profiles for peptide recognition modules from phage-displayed peptide libraries. *Nat Protoc* 2, 1368-1386 (2007).
47. Cai, M. et al. An efficient and cost-effective isotope labeling protocol for proteins expressed in *Escherichia coli*. *J Biomol NMR* 11, 97-102 (1998).
48. Hansen, D. F. et al. An Exchange-Free Measure of 15N Transverse Relaxation: An NMR Spectroscopy Application to the Study of a Folding Intermediate with Pervasive Chemical Exchange. *J Am Chem Soc* 129, 11468-11479 (2007).
49. Bahrami, A., Assadi, A. H., Markley, J. L. & Eghbalnia, H. R. Probabilistic interaction network of evidence algorithm and its application to complete labeling of peak lists from protein NMR spectroscopy. *PLoS Comput Biol* 5, e1000307 (2009).
50. Findeisen, M., Brand, T. & Berger, S. A 1H-NMR thermometer suitable for cryoprobes. *Magn. Reson. Chem.* 45, 175-178 (2007).
51. Grzesiek, S. & Bax, A. The importance of not saturating water in protein NMR. Application to sensitivity enhancement and NOE measurements. *J Am Chem Soc* 115, 12593-12594 (1993).
52. Hansen, D. F., Feng, H., Zhou, Z., Bai, Y. & Kay, L. E. Selective characterization of microsecond motions in proteins by NMR relaxation. *J Am Chem Soc* 131, 16257-16265 (2009).
53. Delaglio, F. et al. NMRPipe: a multidimensional spectral processing system based on UNIX pipes. *J Biomol NMR* 6, 277-293 (1995).
54. Tollinger, M., Skrynnikov, N. R., Mulder, F. A., Forman-Kay, J. D. & Kay, L. E. Slow dynamics in folded and unfolded states of an SH3 domain. *J Am Chem Soc* 123, 11341-11352 (2001).
55. Mulder, F. A. A., Skrynnikov, N. R., Hon, B., Dahlquist, F. W. & Kay, L. E. Measurement of Slow (μs-ms) Time Scale Dynamics in Protein Side Chains by 15N Relaxation Dispersion NMR Spectroscopy: Application to Asn and Gln Residues in a Cavity Mutant of T4 Lysozyme. *J Am Chem Soc* 123, 967-975 (2001).
56. Wertz, I. E. et al. De-ubiquitination and ubiquitin ligase domains of A20 down-regulate NF-kappaB signalling. *Nature* 430, 694-699 (2004).
57. Newton, K. et al. Using linkage-specific monoclonal antibodies to analyze cellular ubiquitylation. *Methods Mol Biol* 832, 185-196 (2012).

58. Matsumoto, M. L. et al. Engineering and Structural Characterization of a Linear Polyubiquitin-Specific Antibody. *J Mol Biol* (2011).doi:10.1016/j.jmb.2011.12.053
59. Matsumoto, M. L. et al. K11-linked polyubiquitination in cell cycle control revealed by a K11 linkage-specific antibody. *Mol Cell* 39, 477-484 (2010).
60. Perkins, D. N., Pappin, D. J., Creasy, D. M. & Cottrell, J. S. Probability-based protein identification by searching sequence databases using mass spectrometry data. *Electrophoresis* 20, 3551-3567 (1999).

SEQUENCES

SEQ ID NO: 1--Wildtype Ubiquitin

MQIFVKTLTGKTITLEVEPSDTIENVKAKIQDKEGIPPDQQRLIFAGKQL

EDGRTLSDYNIQKESTLHLVLRLRGG

We claim:

1. A conformationally stabilized ubiquitin protein comprising the amino acid sequence of SEQ ID NO: 15, wherein Xaa at the position corresponding to amino acid 7 or 8 of SEQ ID NO: 15 is cysteine and Xaa at the position corresponding to amino acid 69 of SEQ ID NO: 15 is cysteine, wherein a β1/β2 loop region of the stabilized protein exhibits slower conformational dynamics in comparison to wild type ubiquitin protein as measured by NMR $R_2$ dispersion, and wherein said conformationally stabilized ubiquitin protein exhibits increased binding affinity to a deubiquitinase of the Ubiquitin Specific Protease (USP) family as compared to said wild type ubiquitin protein.

2. The conformationally stabilized ubiquitin protein of claim 1, wherein microsecond $R_{ex}$ values measured by said NMR $R_2$ dispersion in the region around said β1/β2 loop region are up to 40 fold greater in comparison to said wild type ubiquitin protein.

3. The conformationally stabilized ubiquitin protein of claim 1, wherein Xaa at the position corresponding to amino acid 13 of SEQ ID NO: 15 is N, R, G, K, Y, A, S, H, E, L, T, V, I, M or P; Xaa at the position corresponding to amino acid 34 of SEQ ID NO: 15 is I, F, L, V, S, M, or T; Xaa at the position corresponding to amino acid 36 of SEQ ID NO: 15 is Y, F, L, H, A, V, W, I, M or N; and Xaa at the position corresponding to amino acid 71 of SEQ ID NO: 15 is K, A, Q, W, H, I, R, or G.

4. A conformationally stabilized ubiquitin protein comprising the amino acid sequence of SEQ ID NO: 15, wherein Xaa at the position corresponding to amino acid 7 of SEQ ID NO: 15 is G, D, F, R, or S; Xaa at the position corresponding to amino acid 8 of SEQ ID NO: 15 is A, G, Q, R, or Y; Xaa at the position corresponding to amino acid 13 of SEQ ID NO: 15 is R, Y, E, or P; Xaa at the position corresponding to amino acid 34 of SEQ ID NO: 15 is I, L, or T; Xaa at the position corresponding to amino acid 36 of SEQ ID NO: 15 is L, Y, A, or N; Xaa at the position corresponding to amino acid 69 of SEQ ID NO: 15 is A, G, W, K, Y or I; and Xaa at the position corresponding to amino acid 71 of SEQ ID NO: 15 is A, Q, R, or G, wherein β1/β2 loop region of the stabilized protein exhibits slower conformational dynamics in comparison to wild type ubiquitin protein as measured by NMR $R_2$ dispersion, and wherein said conformationally stabilized ubiquitin protein exhibits increased binding affinity to a deubiquitinase of the Ubiquitin Specific Protease (USP) family as compared to said wild type ubiquitin protein.

5. The conformationally stabilized ubiquitin protein of claim 1, wherein said conformationally stabilized ubiquitin protein binds to said deubiquitinase with a $K_d$ in the nanomolar range.

6. The conformationally stabilized ubiquitin protein of claim 1, wherein said conformationally stabilized ubiquitin protein binds to said deubiquitinase with an affinity that is at least 1000 fold higher than that of said wild type ubiquitin protein.

7. The conformationally stabilized ubiquitin protein of claim 1, wherein said conformationally stabilized ubiquitin protein inhibits deubiquitinase activity.

8. The conformationally stabilized ubiquitin protein of claim 1, wherein said conformationally stabilized protein exhibits no binding or decreased binding to a deubiquitinase of the Ubiquitin C-terminal Hydrolase (UCH) family compared to said wild type ubiquitin protein.

9. A protein complex comprising the conformationally stabilized ubiquitin protein of claim 1 and a deubiquitinase of the USP family.

10. The conformationally stabilized ubiquitin protein of claim 4, wherein microsecond $R_{ex}$ values measured by said NMR $R_2$ dispersion in the region around said β1/β2 loop region are up to 40 fold greater in comparison to said wild type ubiquitin protein.

11. The conformationally stabilized ubiquitin protein of claim 4, wherein said conformationally stabilized ubiquitin protein binds to said deubiquitinase with a $K_d$ in the nanomolar range.

12. The conformationally stabilized ubiquitin protein of claim 4, wherein said conformationally stabilized ubiquitin protein binds to said deubiquitinase with an affinity that is at least 1000 fold higher than that of said wild type ubiquitin protein.

13. The conformationally stabilized ubiquitin protein of claim 4, wherein said conformationally stabilized ubiquitin protein inhibits deubiquitinase activity.

14. The conformationally stabilized ubiquitin protein of claim 4, wherein said conformationally stabilized protein exhibits no binding or decreased binding to a deubiquitinase of the Ubiquitin C-terminal Hydrolase (UCH) family compared to said wild type ubiquitin protein.

15. A protein complex comprising the conformationally stabilized ubiquitin protein of claim 4 and a deubiquitinase of the USP family.

* * * * *